(12) United States Patent
Wurzer et al.

(10) Patent No.: US 12,377,176 B2
(45) Date of Patent: *Aug. 5, 2025

(54) CANCER DIAGNOSTIC IMAGING AGENTS

(71) Applicants: Technische Universität München, Munich (DE); Technische Universität München—Klinikum Rechts der Isar, Munich (DE)

(72) Inventors: Alexander Josef Wurzer, Munich (DE); Hans-Jürgen Wester, Ilmmünster (DE); Matthias Johannes Eiber, Vaterstetten (DE)

(73) Assignees: Technische Universität München, Munich (DE); Technische Universität München—Klinikum Rechts der Isar, Munich (DE)

( * ) Notice: Subject to any disclaimer, the term of this patent is extended or adjusted under 35 U.S.C. 154(b) by 872 days.

This patent is subject to a terminal disclaimer.

(21) Appl. No.: 17/427,006

(22) PCT Filed: Jan. 30, 2020

(86) PCT No.: PCT/EP2020/052268
§ 371 (c)(1),
(2) Date: Jul. 29, 2021

(87) PCT Pub. No.: WO2020/157184
PCT Pub. Date: Aug. 6, 2020

(65) Prior Publication Data
US 2022/0118120 A1    Apr. 21, 2022

(30) Foreign Application Priority Data

Jan. 30, 2019    (EP) .................................... 19154495

(51) Int. Cl.
*A61K 51/04*    (2006.01)
*A61K 51/10*    (2006.01)
*C07B 59/00*    (2006.01)

(52) U.S. Cl.
CPC ...... *A61K 51/0497* (2013.01); *A61K 51/0482* (2013.01); *A61K 51/1027* (2013.01); *C07B 59/004* (2013.01)

(58) Field of Classification Search
None
See application file for complete search history.

(56) References Cited

U.S. PATENT DOCUMENTS 11,497,819 B2 *  11/2022  Wester ................. A61P 35/00
2020/0197545 A1    6/2020  Wurzer et al.

FOREIGN PATENT DOCUMENTS

| CN | 102626522 | | 8/2012 | |
| WO | 2016/062370 A1 | | 4/2016 | |
| WO | 2019/020831 A1 | | 1/2019 | |
| WO | WO-2019115547 A1 * | | 6/2019 | ......... A61K 51/0482 |

OTHER PUBLICATIONS

Banjeree (Preclinical Evaluation of 86Y-Labeled Inhibitors of Prostate Specific Membrane Antigen for Dosimetry Estimates, 2015, The Journal of Nuclear Medicine, 56:4) (Year: 2015).*
Litau (Next Generation of SiFAlin-Based TATE Derivatives for PET Imaging of SSTR-Positive Tumors: Influence of Molecular Design on In Vitro SSTR Binding and In Vivo Pharmacokinetics, 2015, Bioconjugate Chemistry, 26:2350-2359) (Year: 2015).*
Linder (Synthesis and in Vitro and in Vivo Evaluation of SiFA-Tagged Bombesin and RGD Peptides as Tumor Imaging Probes for Positron Emission Tomography, Mar. 25, 2014, Bioconjugate Chemistry, 25:738-749) (Year: 2014).*
U.S. Appl. No. 16/634,759, filed Jan. 28, 2020, 2020-0197545, Published.
U.S. Appl. No. 17/426,962, filed Jul. 29, 2021, Pending.
Bailey et al., Silicon/Fluorine-18/PSMA: A winning team for PET imaging of prostate cancer. 22nd International Symposium on Radiopharmaceutical Sciences. J Label Compd Radiopharm. 2017;60(Suppl 1):S353, Poster p. 190.
Banerjee et al., Sequential SPECT and optical imaging of experimental models of prostate cancer with a dual modality inhibitor of the prostate-specific membrane antigen. Angew Chem Int Ed Engl. Sep. 19, 2011;50(39):9167-70.
Bernard-Gauthier et al., From Unorthodox to Established: The Current Status of (18)F-Trifluoroborate- and (18) F-SiFA-Based Radiopharmaceuticals in PET Nuclear Imaging. Bioconjug Chem. Feb. 17, 2016;27(2):267-79.
Carroll et al., Orthogonal 18F and 64Cu labelling of functionalised bis(thiosemicarbazonato) complexes. Chem Commun (Camb). Jun. 21, 2010;46(23):4052-4.
Hueting et al., A dual radiolabelling approach for tracking metal complexes: investigating the speciation of copper bis (thiosemicarbazonates) in vitro and in vivo. Metallomics. May 2015;7(5):795-804.

(Continued)

*Primary Examiner* — Michael G. Hartley
*Assistant Examiner* — Kaila A Craig
(74) *Attorney, Agent, or Firm* — Min Yang

(57) ABSTRACT

The present invention relates to a ligand-SIFA-chelator conjugate, comprising, within a single molecule three separate moieties: (a) one or more ligands which are capable of binding to PSMA, (b) a silicon-fluoride acceptor (SIFA) moiety which comprises a covalent bond between a silicon atom and a fluorine atom, and (c) one or more chelating groups, containing a chelated nonradioactive cation.

6 Claims, 30 Drawing Sheets

(56) References Cited

OTHER PUBLICATIONS

Figure 1:
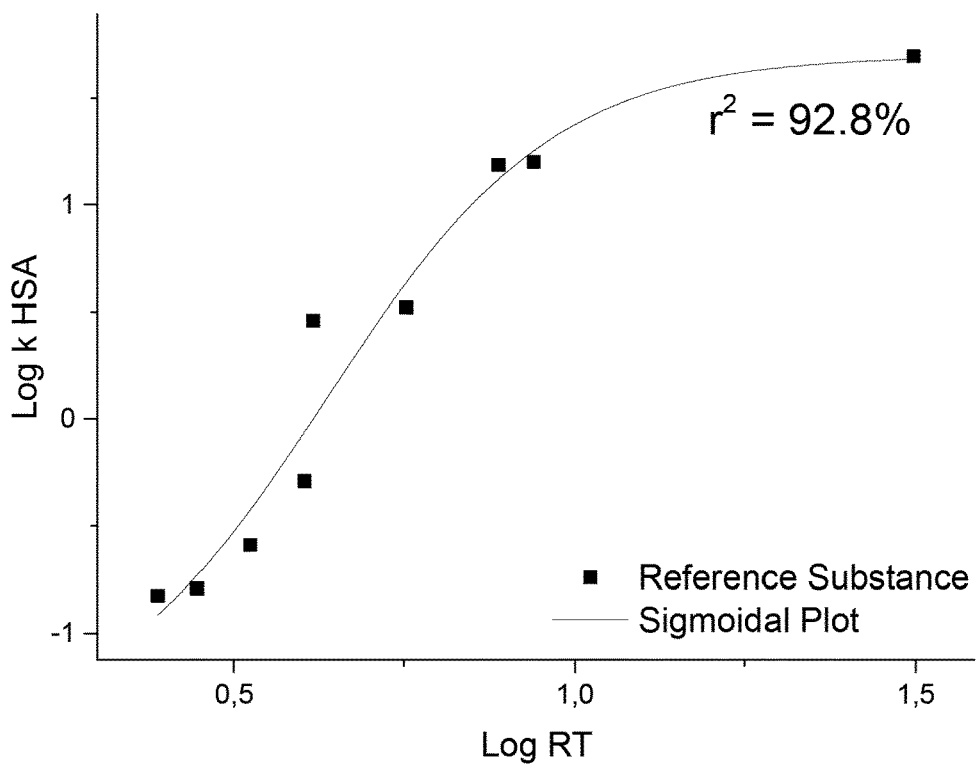

Lindner et al., Synthesis and in vitro and in vivo evaluation of SiFA-tagged bombesin and RGD peptides as tumor imaging probes for positron emission tomography. Bioconjug Chem. Apr. 16, 2014;25(4):738-49.
Litau et al., Next Generation of SiFAlin-Based TATE Derivatives for PET Imaging of SSTR-Positive Tumors: Influence of Molecular Design on In Vitro SSTR Binding and In Vivo Pharmacokinetics. Bioconjug Chem. Dec. 16, 2015;26(12):2350-9.
Lutje et al., PSMA Ligands for Radionuclide Imaging and Therapy of Prostate Cancer: Clinical Status. Theranostics. Oct. 18, 2015;5(12):1388-401.
Westelrund et al., Increasing the Net Negative Charge by Replacement of DOTA Chelator with DOTAGA Improves the Biodistribution of Radiolabeled Second-Generation Synthetic Affibody Molecules. Mol Pharm. May 2, 2016;13(5):1668-78.
International Search Report and Written Opinion for Application No. PCT/EP2020/052268, dated Apr. 6, 2020, 9 pages.

* cited by examiner

Integration TLC

| Substance | RF | %Total % | Typ | Area Counts | %Area % | Instrument | Ret mm | S/N ratio |
|---|---|---|---|---|---|---|---|---|
| [18F]Fluoride | 0,013 | 1,50 | DD( | 1614,00 | 1,74 | TLC | 10,52 | 6,3 |
| [18F]F-PSMA | 0,888 | 84,68 | DD( | 91023,00 | 98,26 | TLC | 54,27 | 167,5 |
| Total in ROI (region of interest) | | | | 92637,00 | 100,00 | | | |
| Total Area | | | | 107492,00 | | | | |
| Area (Total) RF | | | | 99480,00 | | | | |

CANCER DIAGNOSTIC IMAGING AGENTS

RELATED APPLICATIONS

This application is a 35 U.S.C. § 371 national stage filing of International Application No. PCT/EP2020/052268, filed Jan. 30, 2020, which claims the benefit of priority to European Patent Application No. 19154495.6, filed Jan. 30, 2019.

The present invention relates to a ligand-SIFA-chelator conjugate, comprising, within a single molecule: (a) one or more ligands which are capable of binding to PSMA, (b) a silicon-fluoride acceptor (SIFA) moiety which comprises a covalent bond between a silicon and a fluorine atom and which is labeled with $^{18}F$, and (c) one or more chelating groups, containing a chelated nonradioactive cation.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Prostate Cancer

Prostate Cancer (PCa) remained over the last decades the most common malignant disease in men with high incidence for poor survival rates. Due to its overexpression in prostate cancer, prostate-specific membrane antigen (PSMA) or glutamate carboxypeptidase II (GCP II) proved its eligibility as excellent target for the development of highly sensitive radiolabelled agents for endoradiotherapy and imaging of PCa. Prostate-specific membrane antigen is an extracellular hydrolase whose catalytic center comprises two zinc(II) ions with a bridging hydroxido ligand. It is highly upregulated in metastatic and hormone-refractory prostate carcinomas, but its physiologic expression has also been reported in kidneys, salivary glands, small intestine, brain and, to a low extent, also in healthy prostate tissue. In the intestine, PSMA facilitates absorption of folate by conversion of pteroylpoly-γ-glutamate to pteroylglutamate (folate). In the brain, it hydrolyses N-acetyl-L-aspartyl-L-glutamate (NAAG) to N-acetyl-L-aspartate and glutamate.

Prostate-Specific Membrane Antigen (PSMA)

Prostate-specific membrane antigen (PSMA) is a type II transmembrane glycoprotein that is highly overexpressed on prostate cancer epithelial cells. Despite its name, PSMA is also expressed, to varying degrees, in the neovasculature of a wide variety of nonprostate cancers. Among the most common nonprostate cancers to demonstrate PSMA expression include breast, lung, colorectal, and renal cell carcinoma.

The general necessary structures of PSMA targeting molecules comprise a binding unit that encompasses a zinc-binding group (such as urea, phosphinate or phosphoramidate) connected to a P1' glutamate moiety, which warrants high affinity and specificity to PSMA and is typically further connected to an effector functionality. The effector part is more flexible and to some extent tolerant towards structural modifications. The entrance tunnel accommodates two other prominent structural features, which are important for ligand binding. The first one is an arginine patch, a positively charged area at the wall of the entrance funnel and the mechanistic explanation for the preference of negatively charged functionalities at the P1 position of PSMA. This appears to be the reason for the preferable incorporation of negative charged residues within the ligand-scaffold. An in-depth analysis about the effect of positive charges on PSMA ligands has been, to our knowledge, so far not conducted. Upon binding, the concerted repositioning of the arginine side chains can lead to the opening of an S1 hydrophobic accessory pocket, the second important structure that has been shown to accommodate an iodo-benzyl group of several urea based inhibitors, thus contributing to their high affinity for PSMA.

Zhang et al. discovered a remote binding site of PSMA, which can be employed for bidentate binding mode (Zhang et al., Journal of the American Chemical Society 132, 12711-12716 (2010)). The so called arene-binding site is a simple structural motif shaped by the side chains of Arg463, Arg511 and Trp541, and is part of the GCPII entrance lid. The engagement of the arene binding site by a distal inhibitor moiety can result in a substantial increase in the inhibitor affinity for PSMA due to avidity effects. PSMA I&T was developed with the intention to interact this way with PSMA, albeit no crystal structure analysis of binding mode is available. A necessary feature according to Zhang et al. is a linker unit (Suberic acid in the case of PSMA I&T) which facilitates an open conformation of the entrance lid of GCPII and thereby enabling the accessibility of the arene-binding site. It was further shown that the structural composition of the linker has a significant impact on the tumor-targeting and biologic activity as well as on imaging contrast and pharmacokinetics, properties which are crucial for both high imaging quality and efficient targeted endoradiotherapy.

Two categories of PSMA targeting inhibitors are currently used in clinical settings. On the one side there are tracers with chelating units for radionuclide complexation such as PSMA I&T or related compounds. On the other side there are small molecules, comprising a targeting unit and effector molecules.

$^{18}F$ Labelling

Recently, several groups have focused on the development of novel $^{18}F$-labelled urea-based inhibitors for PCa diagnosis. The $^{18}F$-labelled urea-based PSMA inhibitor $^{18}F$-DCFPyl demonstrated promising results in the detection of primary and metastatic. Based on the structure of PSMA-617, the $^{18}F$-labelled analogue PSMA-1007 was recently developed, which showed comparable tumor-to-organ ratios.

An attractive approach for introducing $^{18}F$ labels is the use of silicon fluoride acceptors (SIFA). Silicon fluoride acceptors are described, for example, in Lindner et al., Bioconjugate Chemistry 25, 738-749 (2014). In order to preserve the silicon-fluoride bond, the use of silicon fluoride acceptors introduces the necessity of sterically demanding groups around the silicone atom. This in turn renders silicon fluoride acceptors highly hydrophobic. In terms of binding to the target molecule, in particular to the target molecule which is PSMA, the hydrophobic moiety provided by the silicone fluoride acceptor may be exploited for the purpose of establishing interactions of the radio-diagnostic or -therapeutic compound with the hydrophobic pocket described in Zhang et al., Journal of the American Chemical Society 132, 12711-12716 (2010). Yet, prior to binding, the higher degree of lipophilicity introduced into the molecule poses a severe problem with respect to the development of radiopharmaceuticals with suitable in vivo biodistribution, i.e. low unspecific binding in non-target tissue.

Failure to Solve the Hydrophobicity Problem

Despite many attempts, the hydrophobicity problem caused by silicon fluoride acceptors has not been satisfactorily solved in the prior art.

To explain further, Schirrmacher E. et al. (Bioconjugate Chem. 2007, 18, 2085-2089) synthesized different $^{18}$F-labelled peptides using the highly effective labelling synthon p-(di-tert-butylfluorosilyl) benzaldehyde ([$^{18}$F]SIFA-A), which is one example of a silicon fluoride acceptor. The SIFA technique resulted in an unexpectedly efficient isotopic $^{19}$F—$^{18}$F exchange and yielded the $^{18}$F-synthon in almost quantitative yields in high specific activities between 225 and 680 GBq/μmol (6081-18 378 Ci/mmol) without applying HPLC purification. [$^{18}$F]SIFA-benzaldehyde was finally used to label the N-terminal amino-oxy (N-AO) derivatized peptides AO-Tyr3-octreotate (AO-TATE), cyclo(fK(AO-N)RGD) and N-AO-PEG$_2$-[D-Tyr-Gln-Trp-Ala-Val-Ala-His-Thi-Nle-NH$_2$] (AO-BZH3, a bombesin derivative) in high radiochemical yields. Nevertheless, the labelled peptides are highly lipophilic (as can be taken from the HPLC retention times using the conditions described in this paper) and thus are unsuitable for further evaluation in animal models or humans.

In Wängler C. et al. (Bioconjugate Chem., 2009, 20 (2), pp 317-321), the first SIFA-based Kit-like radio-fluorination of a protein (rat serum albumin, RSA) has been described. As a labelling agent, 4-(di-tert-butyl[$^{18}$F]fluorosilyl)benzenethiol (Si[$^{18}$F]FA-SH) was produced by simple isotopic exchange in 40-60% radiochemical yield (RCY) and coupled the product directly to maleimide derivatized serum albumin in an overall RCY of 12% within 20-30 min. The technically simple labelling procedure does not require any elaborated purification procedures and is a straightforward example of a successful application of Si-18F chemistry for in vivo imaging with PET. The time-activity cureves and μPET images of mice showed that most of the activity was localized in the liver, thus demonstrating that the labelling agent is too lipophilic and directs the in vivo probe to hepatobiliary excretion and extensive hepatic metabolism.

Wängler C. et al. (see Bioconjug Chem. 2010 Dec. 15; 21(12):2289-96) subsequently tried to overcome the major drawback of the SIFA technology, the high lipophilicity of the resulting radiopharmaceuticals, by synthesizing and evaluating new SIFA-octreotate analogues (SIFA-Tyr3-octreotate, SIFA-Asn(AcNH-β-Glc)-Tyr3-octreotate and SIFA-Asn(AcNH-β-Glc)-PEG-Tyr3-octreotate). In these compounds, hydrophilic linkers and pharmacokinetic modifiers were introduced between the peptide and the SIFA-moiety, i.e. a carbohydrate and a PEG linker plus a carbohydrate. As a measure of lipophilicity of the conjugates, the log P(ow) was determined and found to be 0.96 for SIFA-Asn(AcNH-β-Glc)-PEG-Tyr$^3$-octreotate and 1.23 for SIFA-Asn(AcNH-β-Glc)-Tyr$^3$-octreotate. These results show that the high lipophilicity of the SIFA moiety can only be marginally compensated by applying hydrophilic moieties. A first imaging study demonstrated excessive hepatic clearance/liver uptake and thus has never been transferred into a first human study.

Bernard-Gauthier et al. (Biomed Res Int. 2014; 2014: 454503) reviews a great plethora of different SIFA species that have been reported in the literature ranging from small prosthetic groups and other compounds of low molecular weight to labelled peptides and most recently affibody molecules. Based on these data the problem of lipophilicity of SIFA-based prosthetric groups has not been solved sofar; i.e. a methodology that reduces the overall lipophilicity of a SIFA conjugated peptide to a log D lower than approx −2.0 has not been described.

In Lindner S. et al. (Bioconjug Chem. 2014 Apr. 16; 25(4):738-49) it is described that PEGylated bombesin (PESIN) derivatives as specific GRP receptor ligands and RGD (one-letter codes for arginine-glycine-aspartic acid) peptides as specific αvβ3 binders were synthesized and tagged with a silicon-fluorine-acceptor (SIFA) moiety. To compensate the high lipophilicity of the SIFA moiety various hydrophilic structure modifications were introduced leading to reduced logD values. SIFA-Asn(AcNH-β-Glc)-PESIN, SIFA-Ser(β-Lac)-PESIN, SIFA-Cya-PESIN, SIFA-LysMe3-PESIN, SIFA-γ-carboxy-d-Glu-PESIN, SIFA-Cya2-PESIN, SIFA-LysMe3-γ-carboxy-d-Glu-PESI N, SIFA-(γ-carboxy-d-Glu)2-PESIN, SIFA-RGD, SIFA-γ-carboxy-d-Glu-RGD, SIFA-(γ-carboxy-d-Glu)2-RGD, SIFA-LysMe3-γ-carboxy-d-Glu-RGD. All of these peptides—already improved and derivatized with the aim to reduce the lipophilicity—showed a logD value in the range between +2 and −1.22.

In view of the above, the technical problem underlying the present invention can be seen in providing radio-diagnostics which contain a silicone fluoride acceptor and which are, at the same time, characterized by favourable in-vivo properties.

As will be become apparent in the following, the present invention established a proof-of-principle using specific conjugates which bind with high affinity to prostate-specific antigen (PSMA) as target. Accordingly, a further technical problem underlying the present invention can be seen in providing improved diagnostics for the medical indication which is cancer, preferably prostate cancer.

These technical problems are solved by the subject-matter of the claims. Accordingly, in the first aspect, the present invention relates to a ligand-SIFA-chelator conjugate, comprising, within a single molecule: (a) one or more ligands which are capable of binding to PSMA, (b) a silicon-fluoride acceptor (SIFA) moiety which comprises a covalent bond between a silicon and a fluorine atom and which is labeled with $^{18}$F, and (c) one or more chelating groups, containing a chelated nonradioactive cation.

The ligand-SIFA-chelator conjugate comprises three separate moieties. The three separate moieties are a) one or more ligands which are capable of binding to PSMA, (b) a silicon-fluoride acceptor (SIFA) moiety which comprises a covalent bond between a silicon and a fluorine atom, and (c) one or more chelating groups, containing a chelated nonradioactive cation.

For diagnostic imaging, the fluorine atom on the SIFA moiety is $^{18}$F. The $^{18}$F can be introduced by isotopic exchange with $^{19}$F.

Whilst certain ligands which are capable of binding to a disease-relevant target molecule may be cyclic peptides, such cyclic peptides are not chelating groups as envisaged herein, as the problem of the hydrophobic SIFA moiety is not solved in the absence of a further chelating moiety. Thus compounds of the invention require a hydrophilic chelating group in addition to the ligands which are capable of binding to PSMA. The hydrophilic chelating group is required to reduce the hydrophobic nature of the compounds caused by the presence of the SIFA moiety.

The ligand in relation to the first aspect of the invention is defined in functional terms. This is the case because the present invention does not depend on the specific nature of the ligand in structural terms. Rather, a key aspect of the invention is the combination, within a single molecule, of a silicon fluoride acceptor and a chelator or a chelate. These two structural elements, SIFA and the chelator, exhibit a spatial proximity. Preferably, the shortest distance between two atoms of the two elements is less or equal 25 Å, more preferably less than 20 Å and even more preferably less than 15 Å. Alternatively or in addition, it is preferred that not more than 25 covalent bonds separate an atom of the SIFA moiety and an atom the chelator, preferably not more than 20 chemical bonds and even more preferably not more than 15 chemical bonds.

The cation in accordance with item (c) of the first aspect is a non-radioactive cation. It is preferably a non-radioactive metal cation. Examples are given further below.

As a consequence, conjugates fall under the terms of the first aspect which are radioactively labelled at the SIFA moiety, as well as molecules which are not radiolabelled at all. In the latter case, the chelating group may be either a complex of a cold (non-radioactive) ion or may be devoid of any ion.

The present inventors surprisingly discovered that placement of the silicone fluoride acceptor in the neighbourhood of a hydrophilic chelator such as, but not limited to, DOTAGA or DOTA, shields or compensates efficiently the lipophilicity of the SIFA moiety to an extent which shifts the overall hydrophobicity of compound in a range which renders the compound suitable for in-vivo administration.

A further advantage of the compounds, especially of PSMA targeted compounds of the present invention is their surprisingly low accumulation in the kidneys of mice when compared to other PSMA targeted radiopharmaceuticals, such as PSMA I&T. Without wishing to be bound by a particular theory, it seems to be the combination of the structural element SIFA with a chelator which provides for the unexpected reduction of accumulation in the kidneys.

In terms of lipophilicity/hydrophilicity, the logP value (sometimes also referred to as logD value) is an art-established measure.

The term "lipophilicity" relates to the strength of being dissolved in, or be absorbed in lipid solutions, or being adsorbed at a lipid-like surface or matrix. It denotes a preference for lipids (literal meaning) or for organic or apolar liquids or for liquids, solutions or surfaces with a small dipole moment as compared to water. The term "hydrophobicity" is used with equivalent meaning herein. The adjectives lipophilic and hydrophobic are used with corresponding meaning to the substantives described above.

The mass flux of a molecule at the interface of two immiscible or substantially immiscible solvents is governed by its lipophilicity. The more lipophilic a molecule is, the more soluble it is in the lipophilic organic phase. The partition coefficient of a molecule that is observed between water and n-octanol has been adopted as the standard measure of lipophilicity. The partition coefficient P of a species A is defined as the ratio $P=[A]_{n\text{-}octanol}/[A]_{water}$. A figure commonly reported is the logP value, which is the logarithm of the partition coefficient. In case a molecule is ionizable, a plurality of distinct microspecies (ionized and not ionized forms of the molecule) will in principle be present in both phases. The quantity describing the overall lipophilicity of an ionizable species is the distribution coefficient D, defined as the ratio $D=[\text{sum of the concentrations of all microspecies}]_{n\text{-}octanol}/[\text{sum of the concentrations of all microspecies}]_{water}$. Analogous to logP, frequently the logarithm of the distribution coefficient, logD, is reported. Often, a buffer system, such as phosphate buffered saline is used as alternative to water in the above described determination of logP.

If the lipophilic character of a substituent on a first molecule is to be assessed and/or to be determined quantitatively, one may assess a second molecule corresponding to that substituent, wherein said second molecule is obtained, for example, by breaking the bond connecting said substituent to the remainder of the first molecule and connecting (the) free valence(s) obtained thereby to hydrogen(s).

Alternatively, the contribution of the substituent to the logP of a molecule may be determined. The contribution $\pi_{X\,x}$ of a substituent X to the logP of a molecule R—X is defined as $\pi_{X\,x}=\log P_{R-X}-\log P_{R-H}$, wherein R—H is the unsubstituted parent compound.

Values of P and D greater than one as well as logP, logD and $\pi_{X\,x}$ values greater than zero indicate lipophilic/hydrophobic character, whereas values of P and D smaller than one as well as logP, logD and $\pi_{X\,x}$ values smaller than zero indicate hydrophilic character of the respective molecules or substituents.

The above described parameters characterizing the lipophilicity of the lipophilic group or the entire molecule according to the invention can be determined by experimental means and/or predicted by computational methods known in the art (see for example Sangster, Octanol-water Partition Coefficients: fundamentals and physical chemistry, John Wiley & Sons, Chichester. (1997)).

In a preferred embodiment, the logP value of the compounds of the invention is between −5 and −1.5. It is particularly preferred that the logP value is between −3.5 and −2.0.

In a preferred embodiment, a ligand in accordance with the invention comprises or consists of a peptide, a peptidomimetic or a substituted urea, substituents including amino acids. It is understood that a ligand which comprises a peptide or peptidomimetic also comprises a non-peptidic and non-peptidomimetic part. In terms of molecular weight, preference is given to molecular weights below 15 kDa, below 10 kDa or below 5 kDa. Accordingly, small proteins are also embraced by the term "ligand". Target molecules are not particularly limited and include enzymes, receptors, epitopes, transporters, cell surface molecules and proteins of the extracellular matrix. Preferred are targets which are disease relevant. Particularly preferred are targets which are causally involved in a given disease, or which are highly overexpressed in a given disease and/or the inhibition of which can cause a beneficial effect in a patient suffering from a given disease. The ligands are preferably high affinity ligands with preferable affinity, expressed as $IC_{50}$, being below 50 nM, below 20 nM or below 5 nM.

Especially preferred are those ligands which bind with high affinity to prostate-specific membrane antigen (PSMA).

Preferably, the silicon-fluoride acceptor (SIFA) moiety has the structure represented by formula (I):

(I)

Wherein F is understood to encompass both $^{19}F$ and $^{18}F$, $R^{1S}$ and $R^{2S}$ are independently a linear or branched C3 to C10 alkyl group, preferably $R^{1S}$ and $R^{2S}$ are selected from isopropyl and tert-butyl, and are more preferably $R^{1S}$ and $R^{2S}$ are tert-butyl; $R^{3S}$ is a C1 to C20 hydrocarbon group which may comprise one or more aromatic and one or more aliphatic units and/or up to 3 heteroatoms selected from O and S, preferably $R^{3S}$ is a C6 to C10 hydrocarbon group which comprises an aromatic ring and which may comprise one or more aliphatic units; more preferably $R^{3S}$ is a phenyl ring, and most preferably, $R^{3S}$ is a phenyl ring wherein the Si-containing substituent and the bond marked by ⌇⌇⌇⌇ are in a para-position, and wherein the SIFA moiety is attached to the remainder of the conjugate via the bond marked by ⌇⌇⌇⌇.

More preferably, the silicon-fluoride acceptor (SIFA) moiety has the structure represented by formula (Ia):

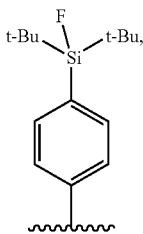

(Ia)

wherein t-Bu indicates a tert-butyl group;

and F is understood to encompass both $^{19}F$ and $^{18}F$

A preferred chelating group comprises at least one of the following (i), (ii) or (iii).

(i) A macrocyclic ring structure with 8 to 20 ring atoms of which 2 or more, more preferably 3 or more, are selected from oxygen atoms or nitrogen atoms. Preferably, 6 or less ring atoms are selected from oxygen atoms or nitrogen atoms. Especially preferred is that 3 or 4 ring atoms are nitrogen atoms or oxygen atoms. Among the oxygen and nitrogen atoms, preference is given to the nitrogen atoms. In combination with the macrocyclic ring structure, the preferred chelating group may comprise 2 or more, such as 2 to 6, preferably 2 to 4, carboxyl groups and/or hydroxyl groups. Among the carboxyl groups and the hydroxyl groups, preference is given to the carboxyl groups.

(ii) An acyclic, open chain chelating structure with 8 to 20 main chain (back bone) atoms of which 2 or more, more preferably 3 or more are heteroatoms selected from oxygen atoms or nitrogen atoms. Preferably, 6 or less back bone atoms are selected from oxygen atoms or nitrogen atoms. Among the oxygen and nitrogen atoms, preference is given to the nitrogen atoms. More preferably, the open chain chelating structure is a structure which comprises a combination of 2 or more, more preferably 3 or more heteroatoms selected from oxygen atoms or nitrogen atoms, and 2 or more, such as 2 to 6, preferably 2 to 4, carboxyl groups and/or hydroxyl groups. Among the carboxyl groups and the hydroxyl groups, preference is given to the carboxyl groups.

(iii) A branched chelating structure containing a quaternary carbon atom. Preferably the quaternary carbon atom is substituted with 3 identical chelating groups in addition to the SIFA/ligand moiety. The substituted chelating groups can comprise an amide. The substituted chelating groups can comprise an aromatic group. The substituted chelating groups can comprise a hydroxypyridinone.

In preferred specific examples, the chelating group is a residue of a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecan (DO2A) 1,4,7,10-tetracyclododecan-N,N',N'',N'''-tetraacetic acid (DOTA), α-(2-carboxyethyl)-1,4,7,10-tetraazacyclododecane-1,4,7,10-tetraacetic acid (DOTAGA), 1,4,7,10 tetraazacyclododecane N,N',N'',N''' 1,4,7,10-tetra(methylene) phosphonic acid (DOTMP), N,N'-dipyridoxylethylendiamine-N,N'-diacetate-5,5'-bis(phosphat) (DPDP), diethylene triamine N,N',N'' penta(methylene) phosphonic acid (DTMP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), tetra 3-hydroxy-N-methyl-2-pyridinone chelators (4-((4-(3-(bis(2-(3-hydroxy-1-methyl-2-oxo-1,2-dihydropyridine-4-carboxamido)ethyl)amino)-2-((bis(2-(3-hydroxy-1-methyl-2-oxo-1,2-dihydropyridine-4-carboxamido)ethyl)amino)methyl)propyl)phenyl)amino)-4-oxobutanoic acid), abbreviated as Me-3,2-HOPO, 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis (carboxymethyl)-1,4,8,11-tetraazabicyclo[6.6.2]hexadecane (TE2A), 1,4,8,11-tetraazacyclododecane-1,4,8,11-tetraacetic acid (TETA), tris(hydroxypyridinone) (THP), terpyridin-bis(methyleneamintetraacetic acid (TMT), 1,4,7-triazacyclononane-1,4,7-tris[methylene(2-carboxyethyl) phosphinic acid] (TRAP), 1,4,7,10-tetraazacyclotridecan-N,N',N'',N'''-tetraacetic acid (TRITA), 3-[[4,7-bis[[2-carboxyethyl(hydroxy)phosphoryl]methyl]-1,4,7-triazonan-1-yl]methyl-hydroxy-phosphoryl]propanoic acid, and triethylenetetraaminehexaacetic acid (TTHA), which residue is provided by covalently binding a carboxyl group contained in the chelating agent to the remainder of the conjugate via an ester or an amide bond.

Particular chelators are shown below:

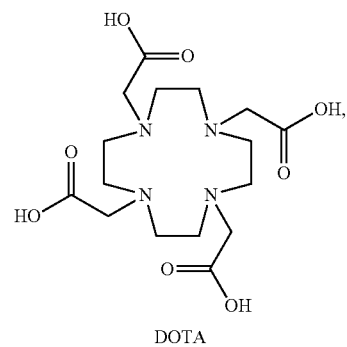

DOTA

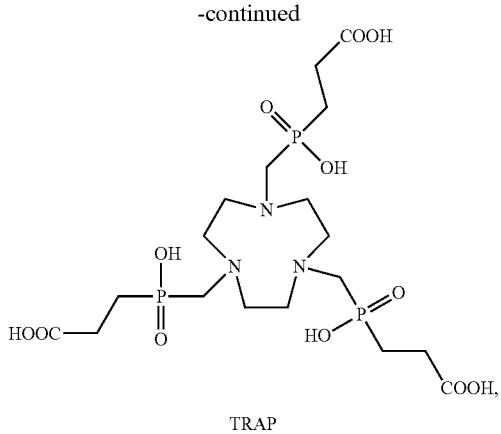

TRAP

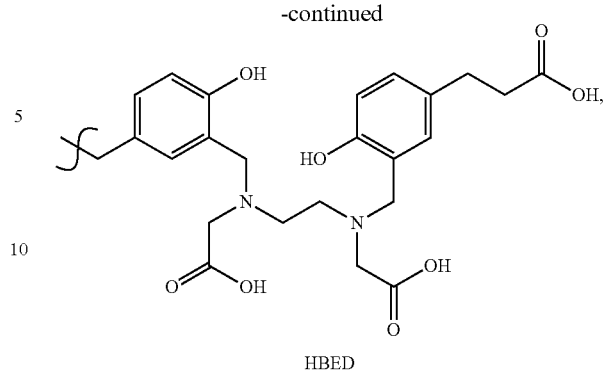

HBED

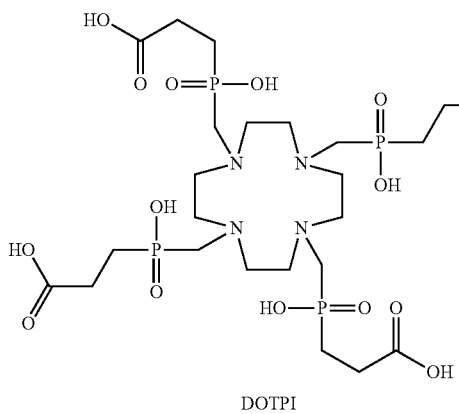

DOTPI

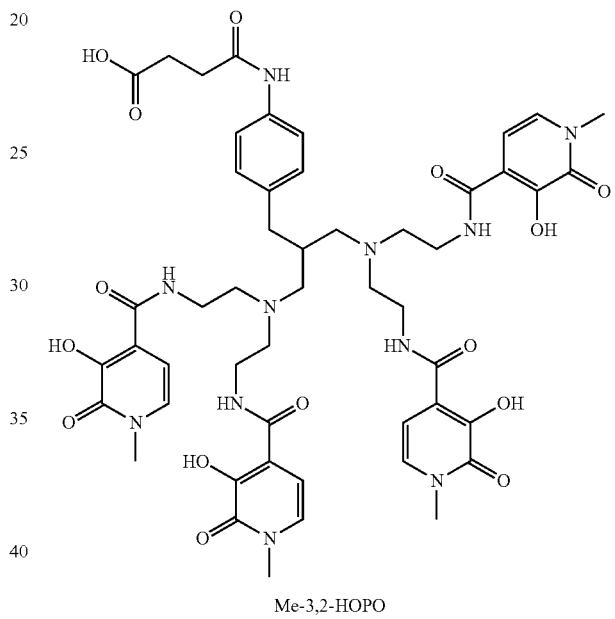

Me-3,2-HOPO

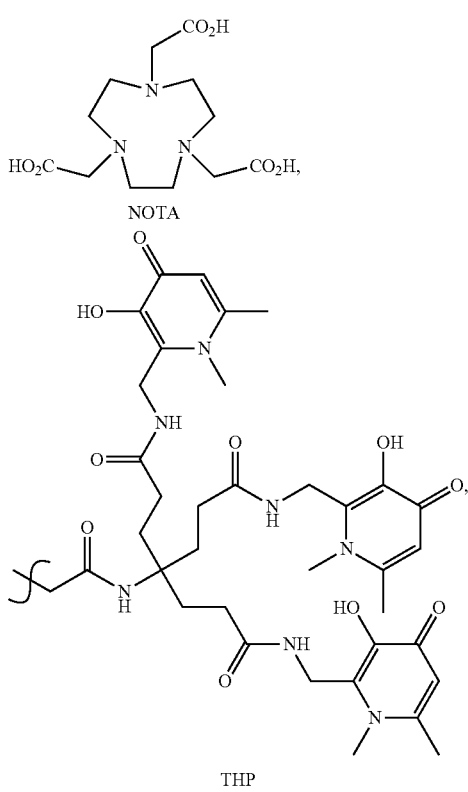

NOTA

THP

Among the above exemplary chelating agents, particular preference is given to a chelating agent selected from TRAP, DOTA and DOTAGA.

Metal- or cation-chelating macrocyclic and acyclic compounds are well-known in the art and available from a number of manufacturers. While the chelating moiety in accordance with the present invention is not particularly limited, it is understood that numerous moieties can be used in an off-the-shelf manner by a skilled person without further ado.

The chelating group may comprise a chelated cation which is non-radioactive.

Preferred examples of cations that may be chelated by the chelating group are the non-radioactive cations of Sc, Cr, Mn, Co, Fe, Ni, Cu, Ga, Zr, Y, Tc, Ru, Rh, Pd, Ag, In, Sn, te, Pr, Pm, Tb, Sm, Gd, Tb, Ho, Dy, Er, Yb, Tm, Lu, Re, Pt, Hg, Au, Pb At, Bi, Ra, Ac, Th; more preferably the cations of Sc, Cu, Ga, Y, In, Tb, Ho, Lu, Re, Pb, Bi, Ac, Th and Er. The cation may be Ga. The cation may be Lu.

Accordingly, the ligand is preferably capable of binding to prostate-specific membrane antigen (PSMA).

More preferably, the ligand has the structure represented by formula (II):

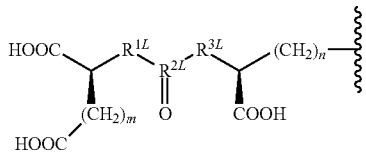
(II)

wherein m is an integer of 2 to 6, preferably 2 to 4, more preferably 2; n is an integer of 2 to 6, preferably 2 to 4, more preferably 2 or 3; $R^{1L}$ is $CH_2$, NH or O, preferably NH; $R^{3L}$ is $CH_2$, NH or O, preferably NH; $R^{2L}$ is C or P(OH), preferably C; and wherein the ligand is attached to the remainder of the conjugate via the bond marked by ⁓⁓⁓.

The ligand can have the structure represented by formula (IIa):

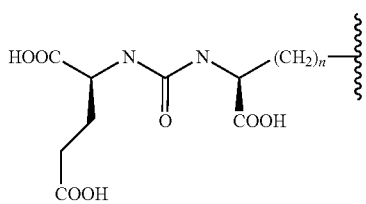
(IIa)

wherein n is an integer of 2 to 6; and wherein the ligand is attached to the remainder of the conjugate via the bond marked by ⁓⁓⁓.

A number of PSMA binders are known in the art which are all suitable in accordance with the invention. The above preferred embodiment is a structural definition of a preferred group of PSMA binders.

It is particularly preferred that the conjugate of the first aspect is a compound of formula (III):

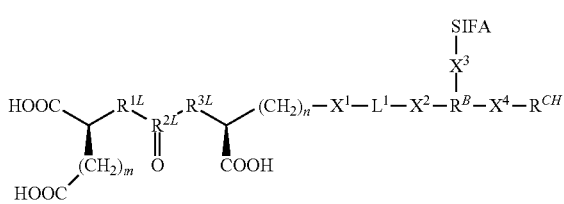
(III)

or a pharmaceutically acceptable salt thereof, wherein:

SIFA is a silicon-fluoride acceptor (SIFA) moiety which comprises a covalent bond between a silicon and a fluorine atom and which is labeled with $^{18}F$; preferably SIFA is the SIFA moiety of formula (I) and more preferably of formula (Ia) defined above;

m is an integer of 2 to 6, preferably 2 or 3, more preferably 2;

n is an integer of 2 to 6, preferably 2 or 3, more preferably 2 or 4;

$R^{1L}$ is $CH_2$, NH or O, preferably NH;

$R^{3L}$ is $CH_2$, NH or O, preferably NH;

$R^{2L}$ is C or P(OH), preferably C;

$X^1$ is selected from an amide bond, an ether bond, a thioether bond, an ester bond, a thioester bond, an urea bridge, and an amine bond, preferably an amide bond;

$X^2$ is selected from an amide bond, an ether bond, a thioether bond, an ester bond, a thioester bond, an urea bridge, and an amine bond, preferably an amide bond;

$L^1$ is a divalent linking group with a structure selected from an oligoamide, an oligoether, an oligothioether, an oligoester, an oligothioester, an oligourea, an oligo(ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo ether-urea), an oligo(thioether-ester), an oligo(thio-ether-thioester), an oligo(thioether-urea), an oligo(ester-thioester), an oligo(ester-urea), and an oligo(thioester-urea), preferably with a structure selected from an oligoamide and an oligo(ester-amide).

$L^1$ can be optionally substituted with one or more substituents independently selected from —OH, —$OCH_3$, —COOH, —$COOCH_3$, —$NH_2$, and —$NHC(NH)NH_2$.

$X^3$ is selected from an amide bond, and ester bond, an ether, an amine, and a linking group of the formula:

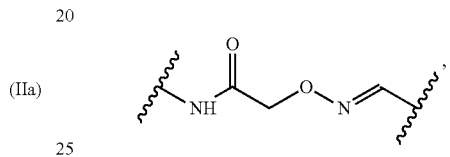

wherein the bond marked by ⁓⁓⁓ at the NH group is bound to $R^B$ and the other bond marked by ⁓⁓⁓ is bound to SIFA; preferably $X^3$ is an amide bond; $R^B$ is a trivalent coupling group.

$X^4$ is selected from an amide bond, an ether bond, a thioether bond, and ester bond, a thioester bond, a urea bridge, an amine bond, a linking group of the formula:

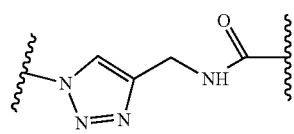 [SMILES: *C(=O)NCc1cn(*)nn1]

wherein the amide bond marked by ⁓⁓⁓ is formed with the chelating group, and the other bond marked by ⁓⁓⁓ is bound to $R^B$; and a linking group of the formula:

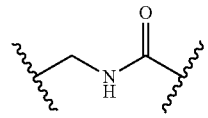 [SMILES: *CNC(*)=O]

wherein the bond marked by ⁓⁓⁓ at the carbonyl end is formed with the chelating group, and the other bond marked by ⁓⁓⁓ is bound to $R^B$; preferably $X^4$ is an amide bond.

$R^{CH}$ is chelating group containing a chelated nonradioactive cation, preferably a nonradioactive metal cation, wherein preferred embodiments of said chelating group and of the optional chelated cation are as defined above.

The term "oligo" as used in oligoamide, oligoether, oligothioether, oligoester, oligothioester, oligourea, oligo (ether-amide), oligo(thioether-amide), oligo(ester-amide), oligo(thioester-amide), oligo(urea-amide), oligo(ether-thioether), oligo(ether-ester), oligo(ether-thioester), oligo (ether-urea), oligo(thioether-ester), oligo(thioether-thioester), oligo (thioether-urea), oligo(ester-thioester), oligo(ester-urea), and oligo(thioester-urea) is preferably to be understood as referring to a group wherein 2 to 20, more preferably wherein 2 to 10 subunits are linked by the type of bonds specified in the same terms. As will be understood by the skilled reader, where two different types of bonds are indicated in brackets, both types of bonds are contained in the concerned group (e.g. in "oligo (ester-amide)", ester bonds and amide bonds are contained).

It is preferred that $L^1$ comprises a total of 1 to 5, more preferably a total of 1 to 3, and most preferably a total of 1 or 2 amide and/or ester bonds, preferably amide bonds, within its backbone.

The term oligoamide therefore describes a moiety having a chain of $CH_2$ or CHR groups interspersed with groups selected from NHCO or CONH. Each occurrence of the R moiety is an optional substituent selected from —OH, —OCH$_3$, —COOH, —COOCH$_3$, —NH$_2$, and —NHC(NH)NH$_2$.

It is also preferred that —$X^1$-$L^1$-$X^2$— represents one of the following structures (L-1) and (L-2):

—NH—C(O)—R$^6$—C(O)—NH—R$^7$—NH—C(O)— (L-1)

—C(O)—NH—R$^8$—NH—C(O)—R$^9$—C(O)—NH—R$^{10}$—NH—C(O)— (L-2)

wherein $R^6$ to $R^{10}$ are independently selected from C2 to C10 alkylene, preferably linear C2 to C10 alkylene, which alkylene groups may each be substituted by one or more substitutents independently selected from —OH, —OCH$_3$, —COOH, —COOCH$_3$, —NH$_2$, and —NHC(NH)NH$_2$.

Especially preferred is that the total number of carbon atoms in $R^6$ and $R^7$ is 4 to 20, more preferably 4 to 16, without carbon atoms contained in optional substituents. Especially preferred is that the total number of carbon atoms in $R^8$ to $R^{10}$, is 6 to 20, more preferably 6 to 16, without carbon atoms contained in optional substituents.

It is particularly preferred that —$X^1$-$L^1$-$X^2$— represents one of the following structures (L-3) and (L-4):

—NH—C(O)—R$^{11}$—C(O)—NH—R$^{12}$—CH(COOH)—NH—C(O)— (L-3)

—C(O)—NH—CH(COOH)—R$^{13}$—NH—C(O)—R$^{14}$—C(O)—NH—R$^{15}$—CH(COOH)—NH—C(O)— (L-4)

wherein $R^{11}$ to $R^{15}$ are independently selected from C2 to C8 alkylene, preferably linear C2 to C8 alkylene.

Especially preferred is that the total number of carbon atoms in $R^{11}$ and $R^{12}$ or $R^{13}$ to $R^{15}$, respectively, is 8 to 18, more preferably 8 to 12, yet more preferably 9 or 10.

Preferably, $R^B$ has the structure represented by formula (IV):

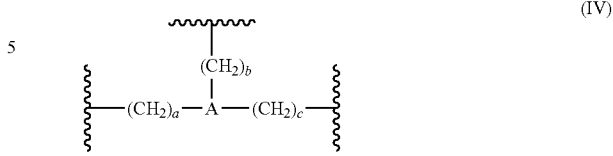

(IV)

wherein: A is selected from N, CR$^{16}$, wherein R$^{16}$ is H or C1-C6 alkyl, and a 5 to 7 membered carbocyclic or heterocyclic group; preferably A is selected from N and CH, and more preferably A is CH; the bond marked by ⌇⌇⌇ at $(CH_2)_a$ is formed with $X^2$, and a is an integer of 0 to 4, preferably 0 or 1, and most preferably 0; the bond marked by ⌇⌇⌇ at $(CH_2)_b$ is formed with $X^3$, and b is an integer of 0 to 4, preferably of 0 to 2, and more preferably 0 or 1; and the bond marked by ⌇⌇⌇ at $(CH_2)_c$ is formed with $X^4$, and c is an integer of 0 to 4, preferably of 0 to 2, and more preferably 0 or 1.

Even more preferred as a conjugate in accordance with the invention is a compound of formula (IIIa):

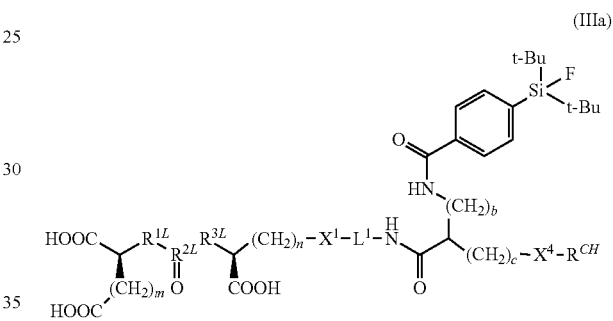

(IIIa)

or a pharmaceutically acceptable salt thereof, wherein m, n, $R^{1L}$, $R^{2L}$, $R^{3L}$, $X^1$, $L^1$, b, c, $X^4$ and $R^{CH}$ are as defined above, including all preferred embodiments thereof.

It is preferred for the compound of formula (IIIa) that b+c≥1.

It is also preferred for the compound of formula (IIIa) that b+c≤3.

It is more preferred for the compound of formula (IIIa) that b is 1 and c is 0.

It is also preferred for the compound of formula (III) that —$X^4$—$R^{CH}$ represents a residue of a chelating agent selected from DOTA and DOTAGA bound with one of its carboxylic groups via an amide bond to the remainder of the conjugate.

In a preferred embodiment of the compound of formula (III), said compound is a compound of formula (IIIb):

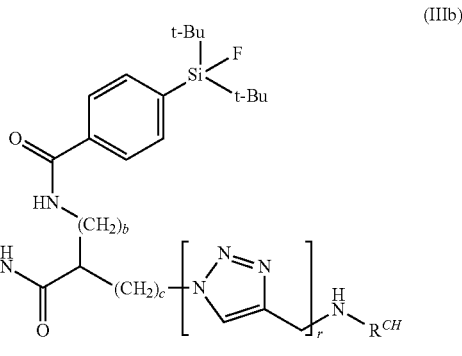

(IIIb)

or a pharmaceutically acceptable salt thereof, wherein m, n, $R^{1L}$, $R^{2L}$, $R^{3L}$, $X^1$, $L^1$, b, c, $X^4$ and $R^{CH}$ are as defined above; and r is 0 or 1.

Especially preferred is that —N(H)—$R^{CH}$ represents a residue of a chelating agent selected from DOTA and DOTAGA bound with one of its carboxylic groups via an amide bond to the remainder of the conjugate.

In order to be used in PET imaging, the compounds require a positron emitting atom. The compounds include $^{18}$F for medical use. Most preferred compounds of the invention are wherein F includes $^{18}$F and $M^{3+}$ refers to a nonradioactive metal cation.

In the compounds herein, the nonradioactive metal cation M may be chelated to one or more COO$^-$ groups. M may be chelated to one or more N atoms. M may be chelated to one or more N atoms or one or more COO$^-$ groups. M may be chelated to one or more N atoms and one or more COO$^-$ groups. Where the chelated nonradioactive metal cation M is shown, the acid groups to which it is chelated are merely representatively shown as COO$^-$, the equivalent fourth acid may also be partly chelated and hence may not literally be COOH.

PSMA-SIFA1 (5)

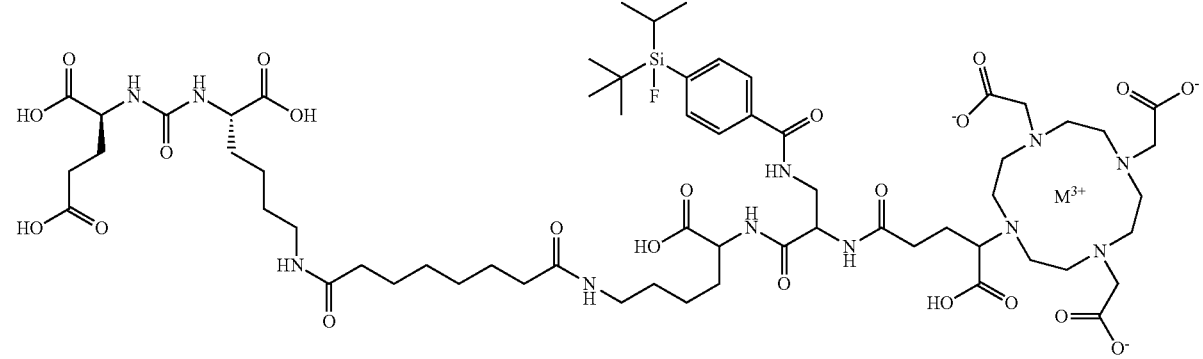

and isomers thereof:

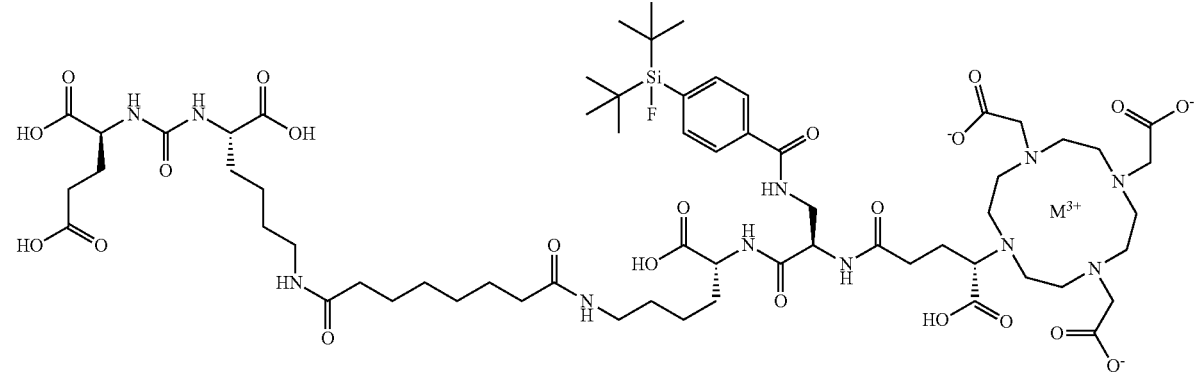

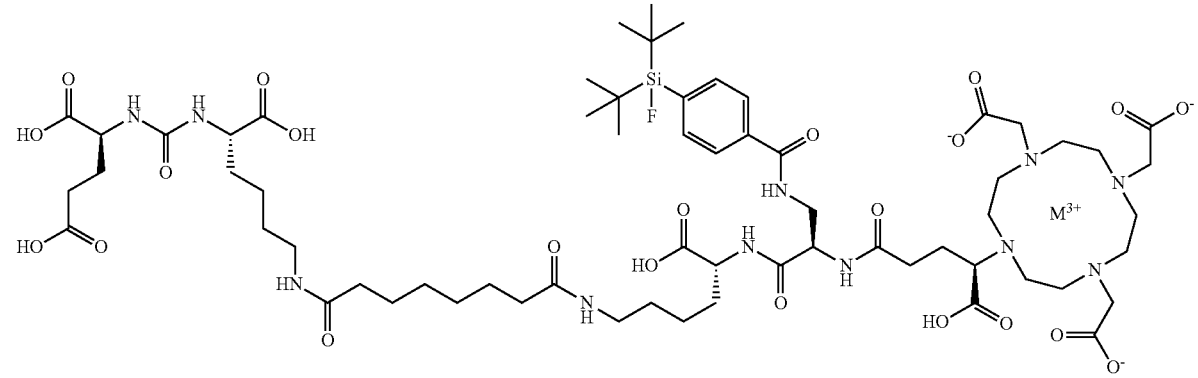

-continued
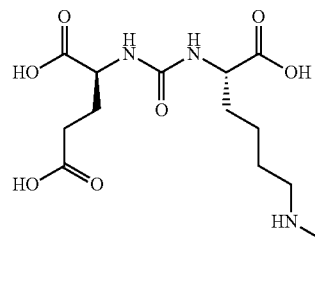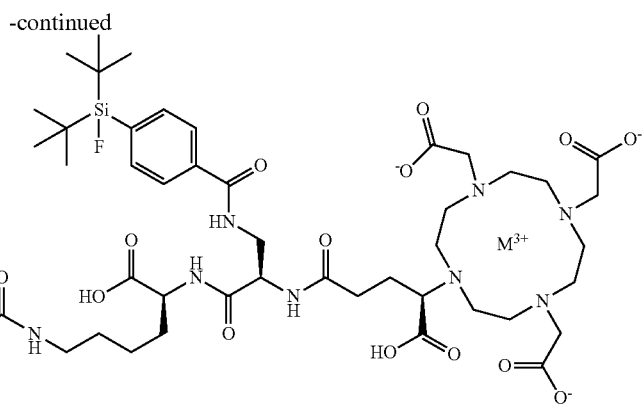
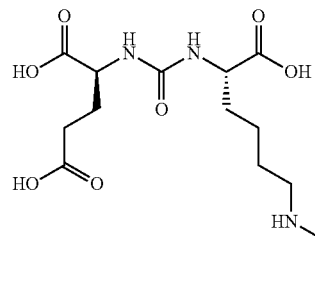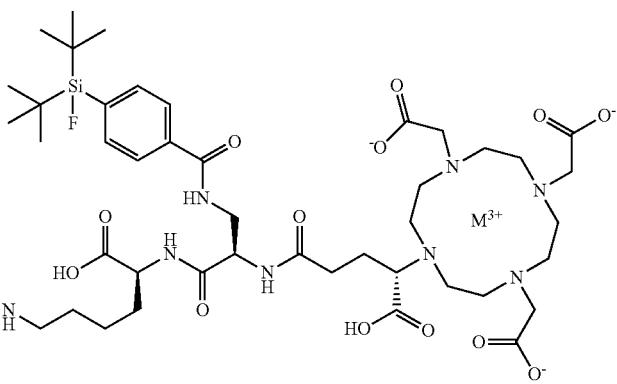
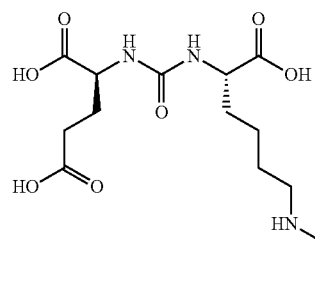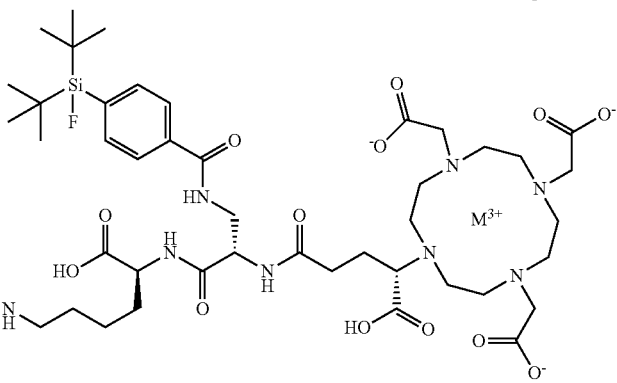
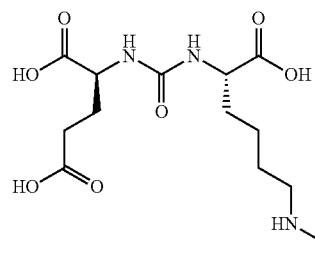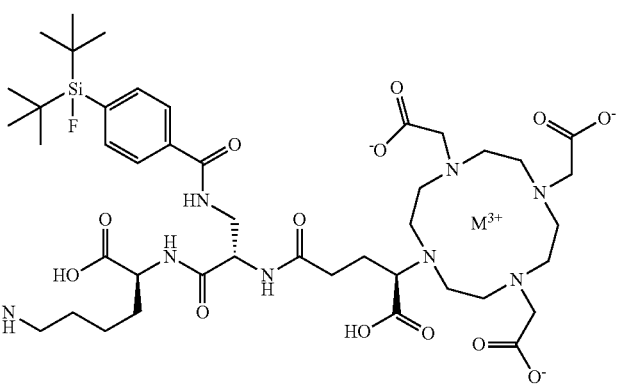

-continued
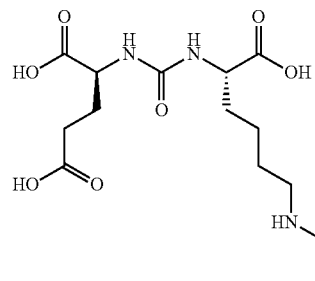
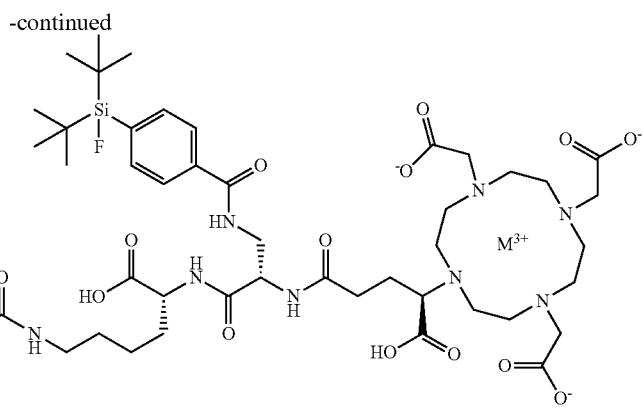
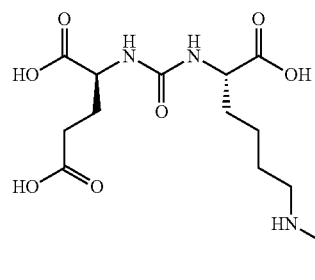
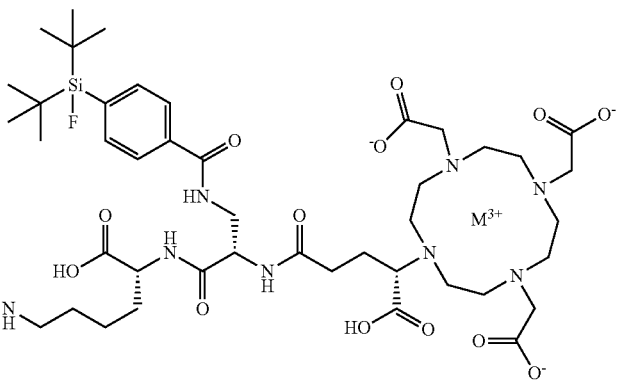
PSMA-SIFA2 (6)
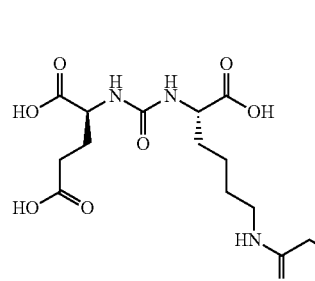
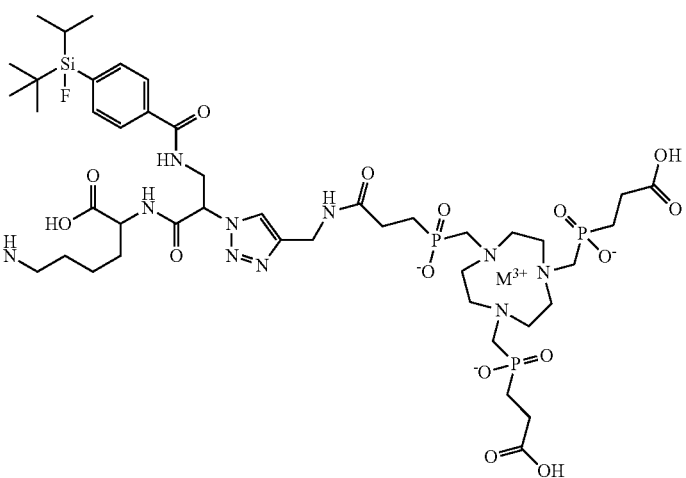

and isomers thereof
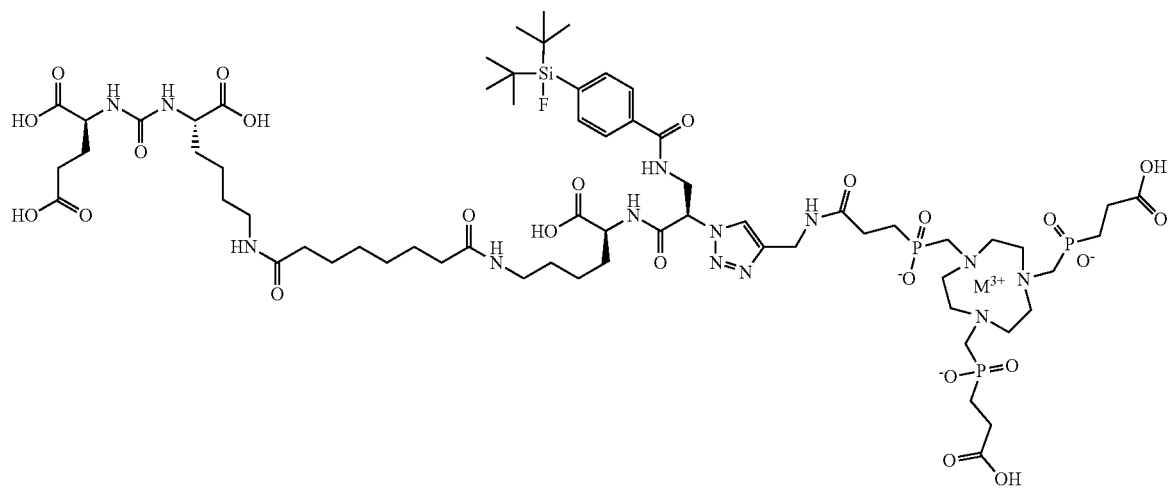
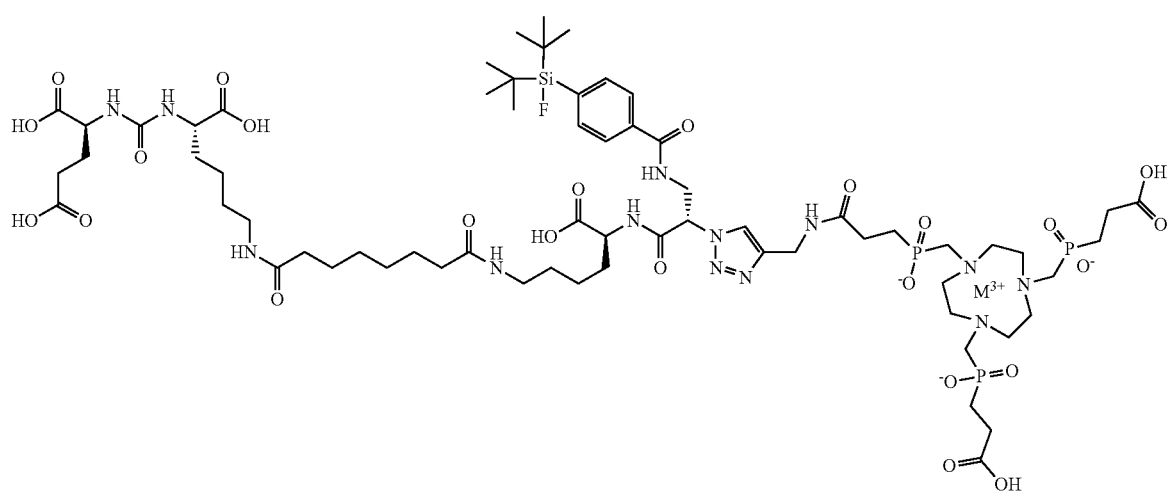
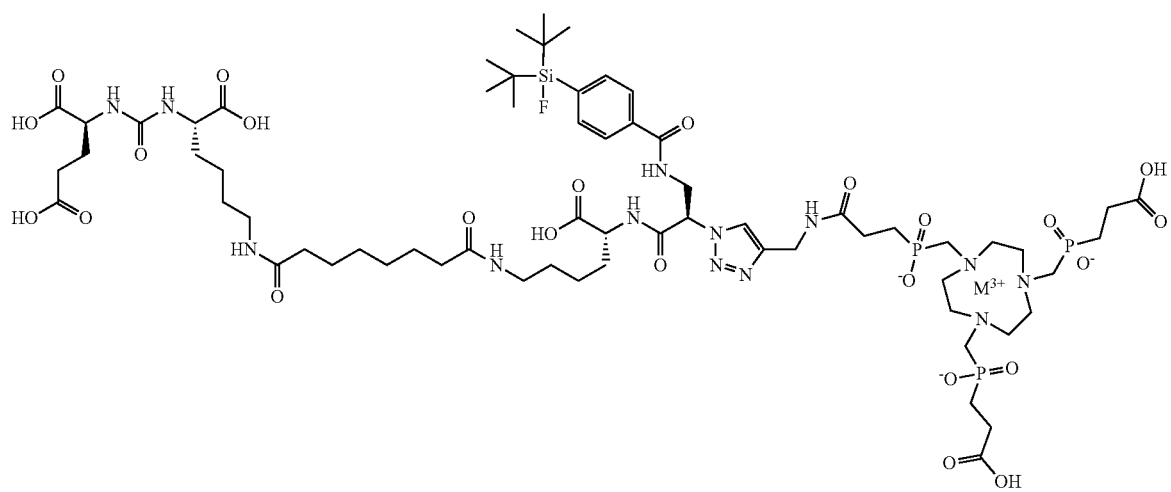

-continued
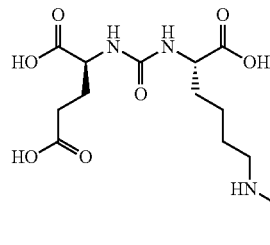
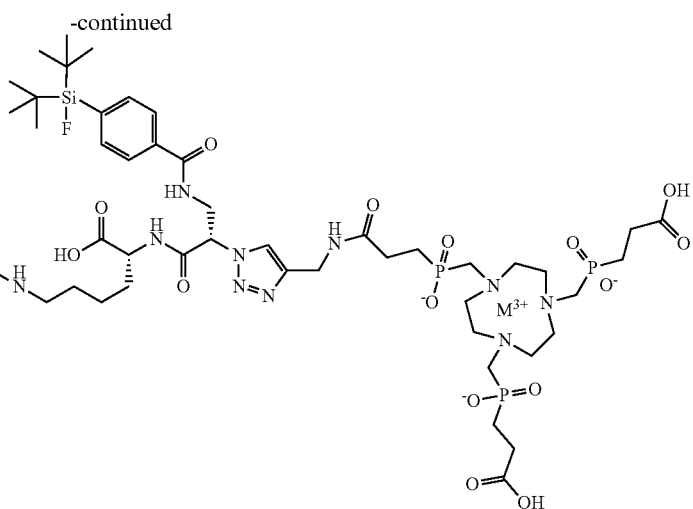
PSMA-SIFA3 (7)
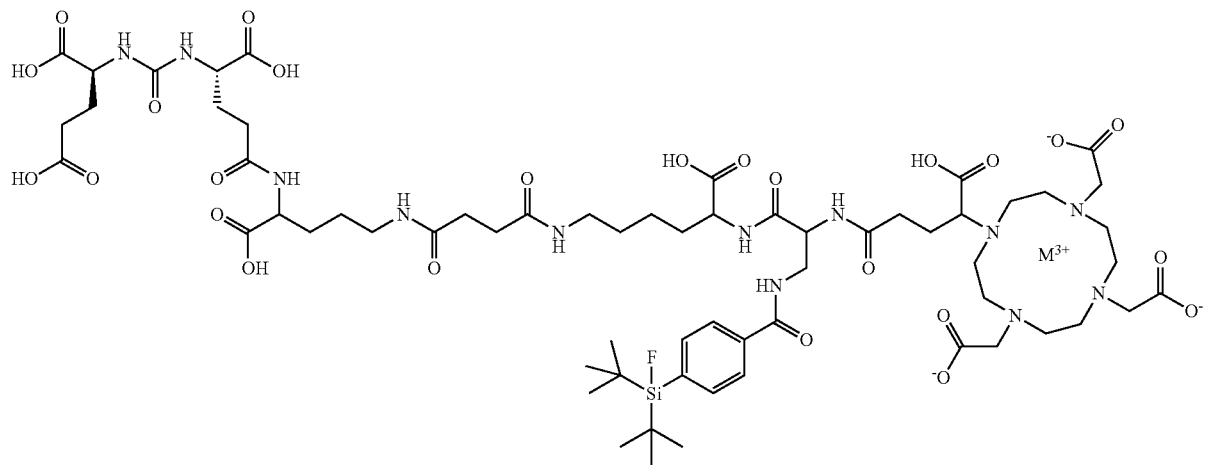
and isomers thereof
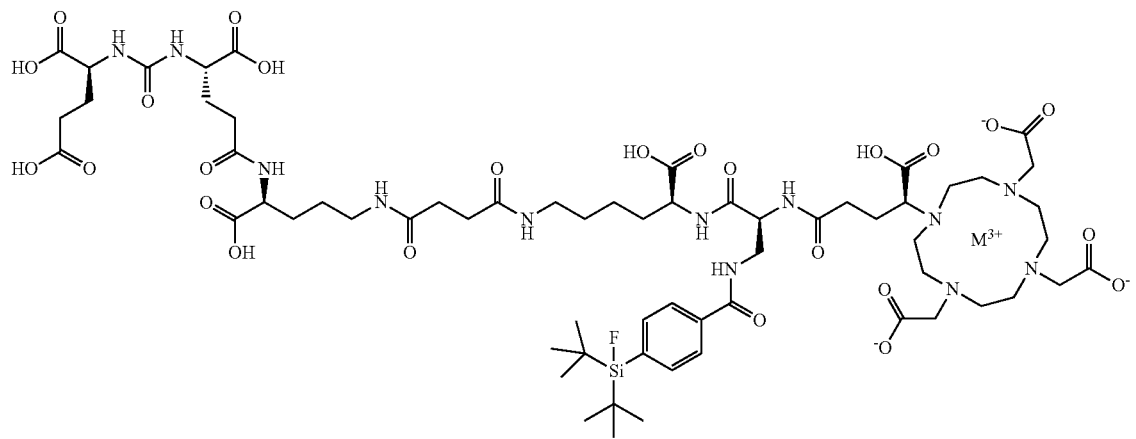

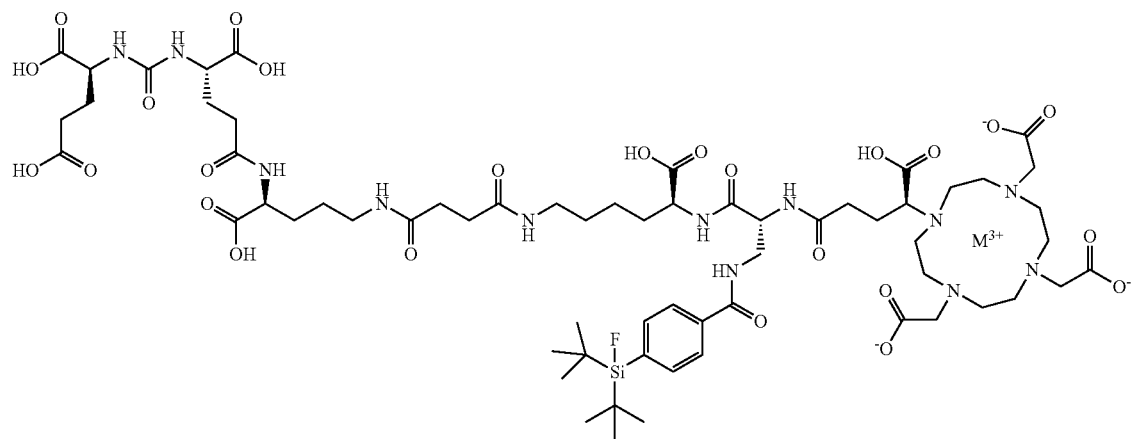
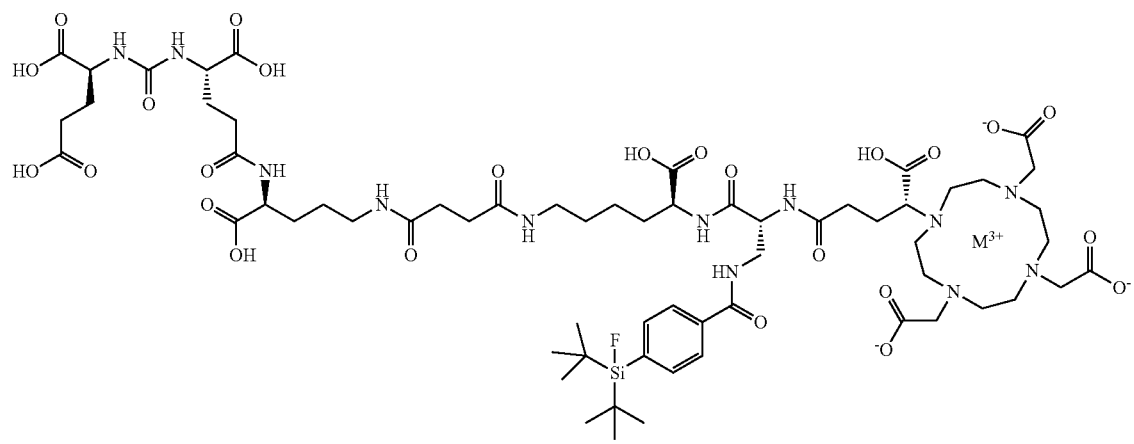
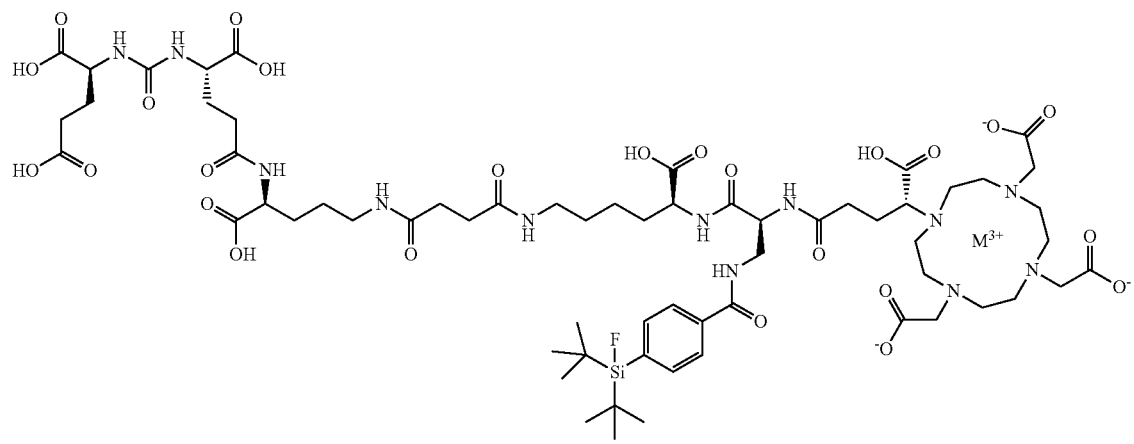

-continued
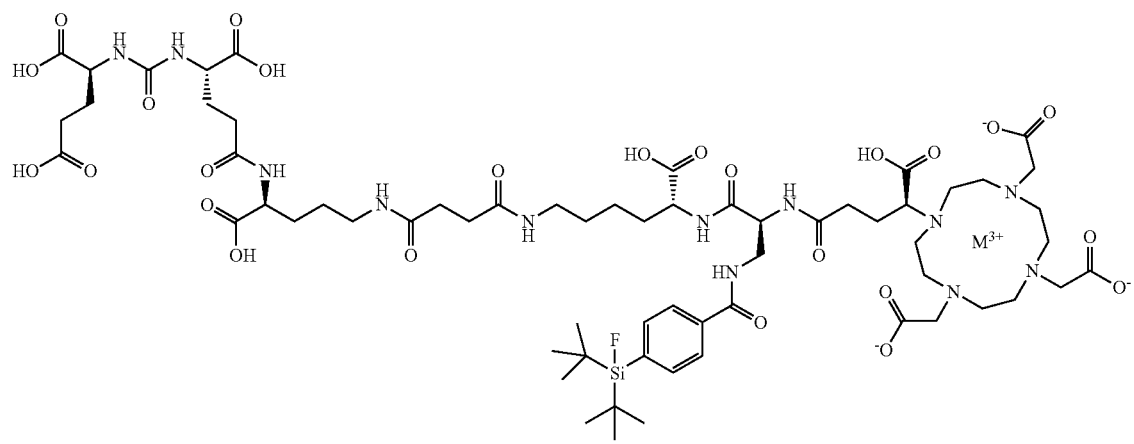
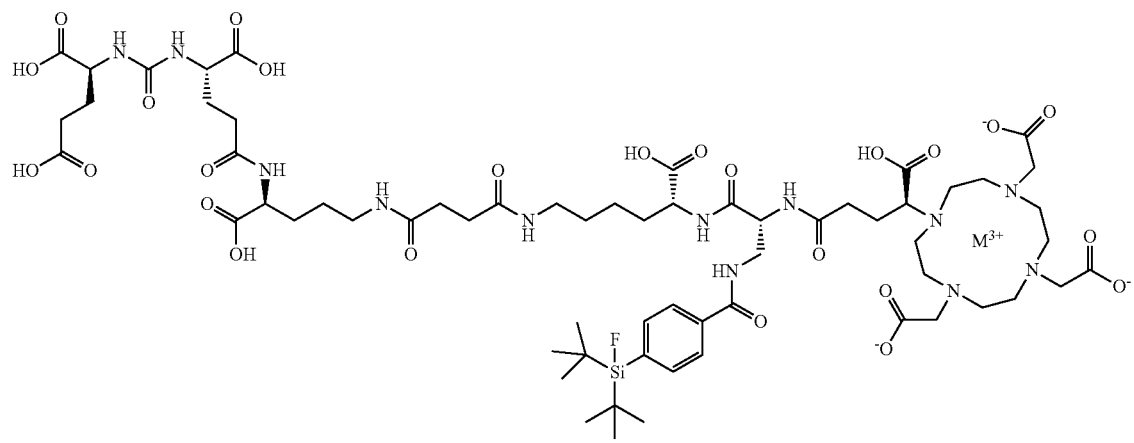
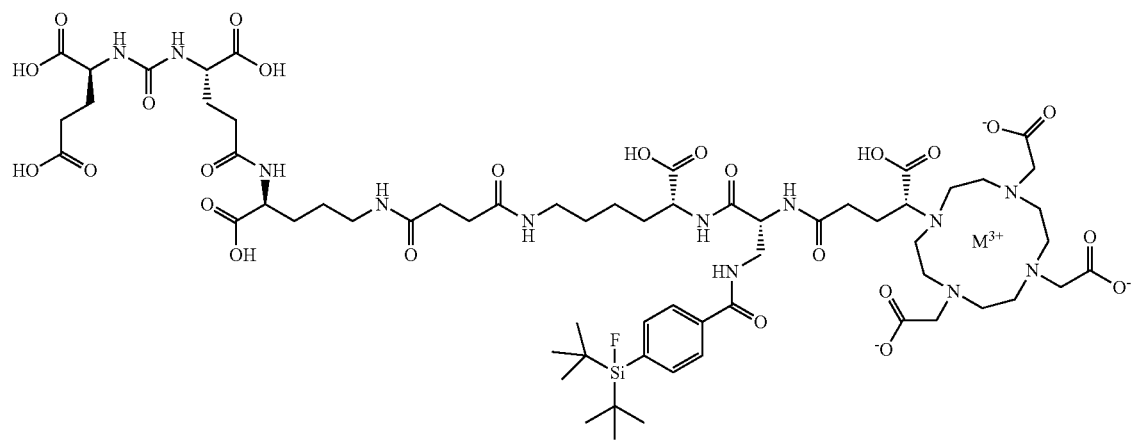

-continued
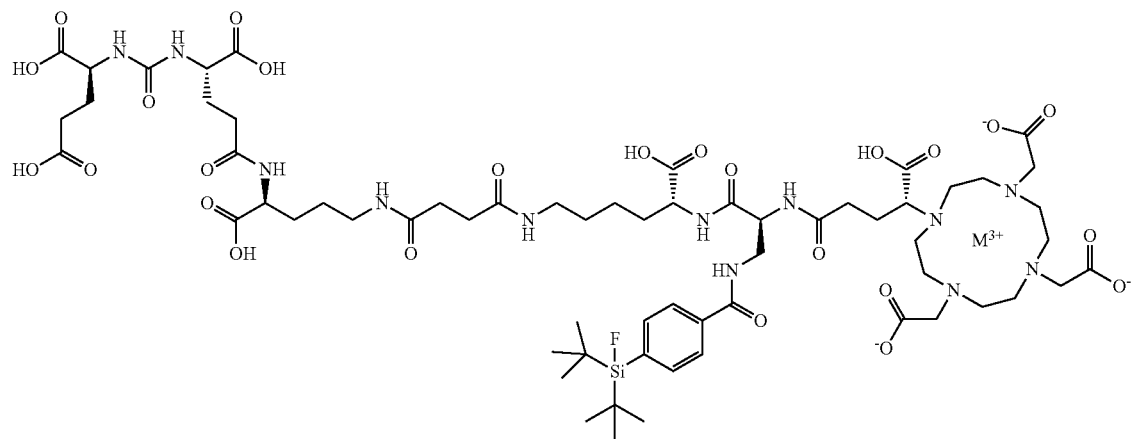
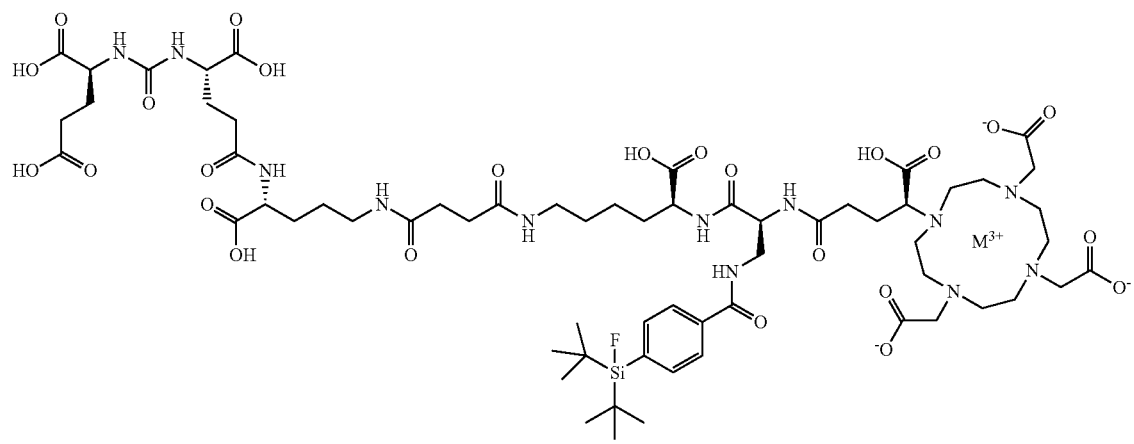
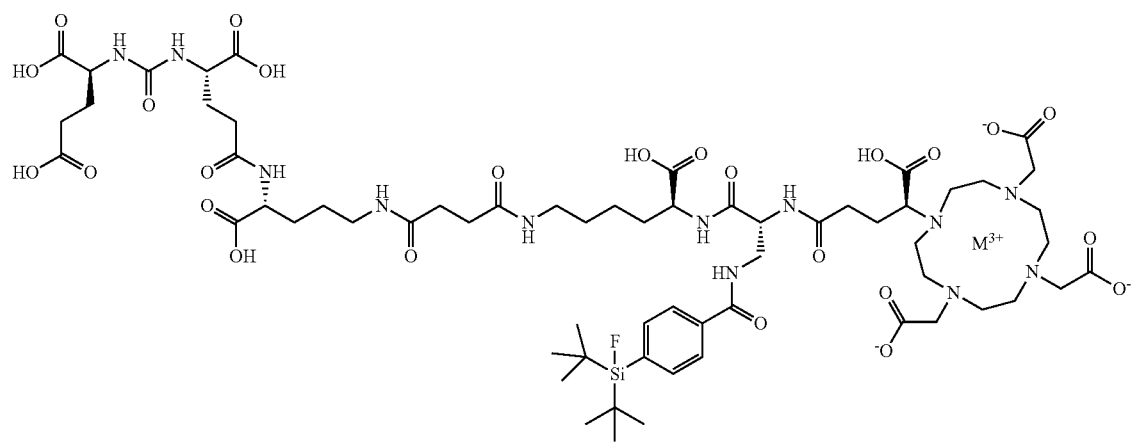

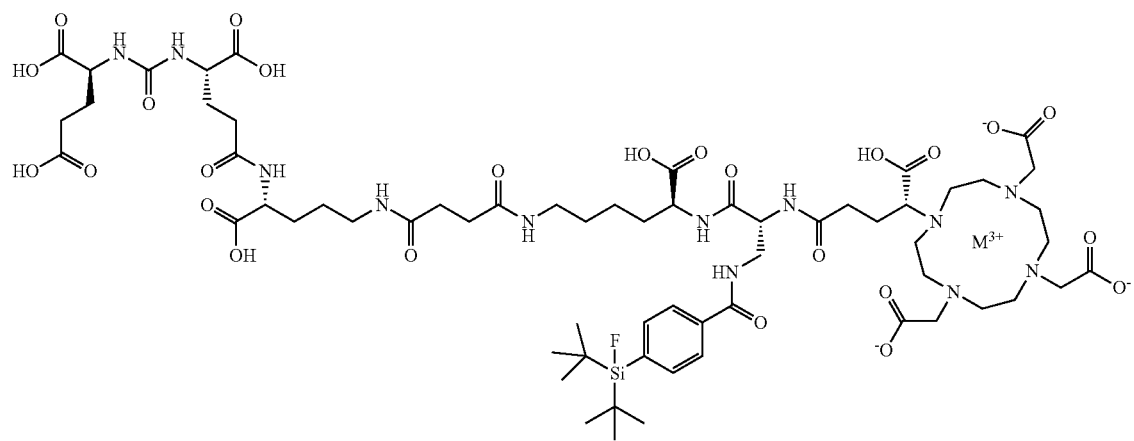
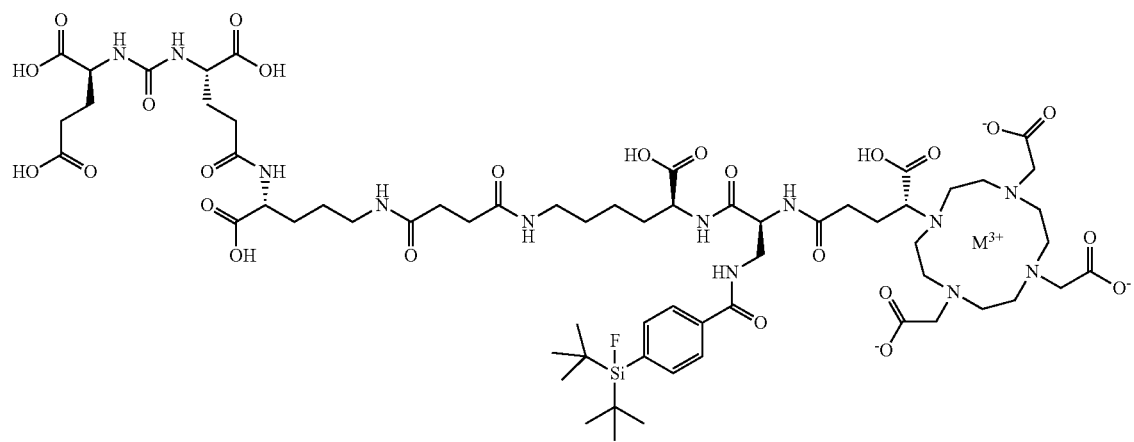
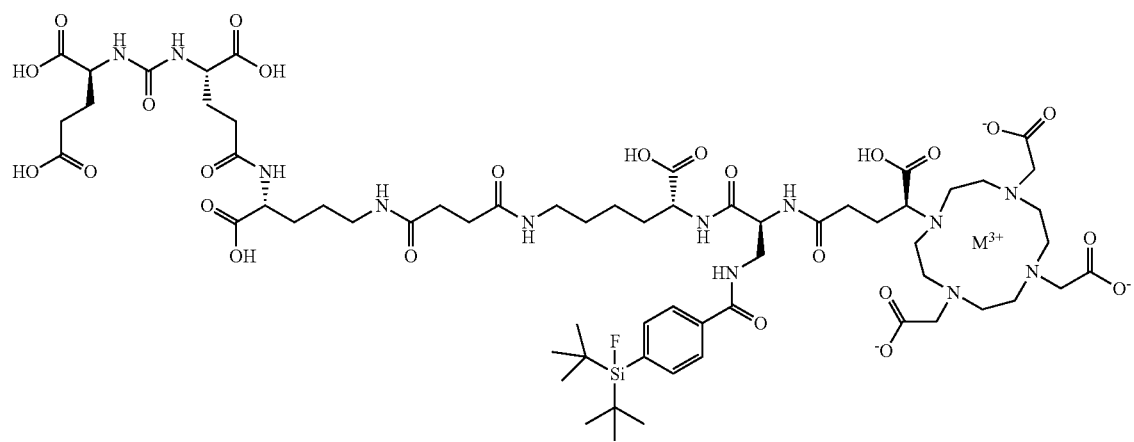

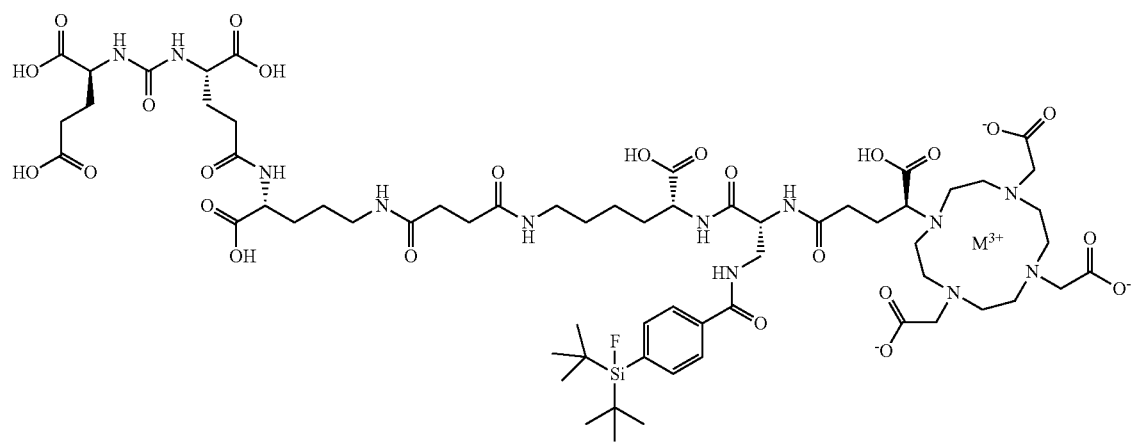
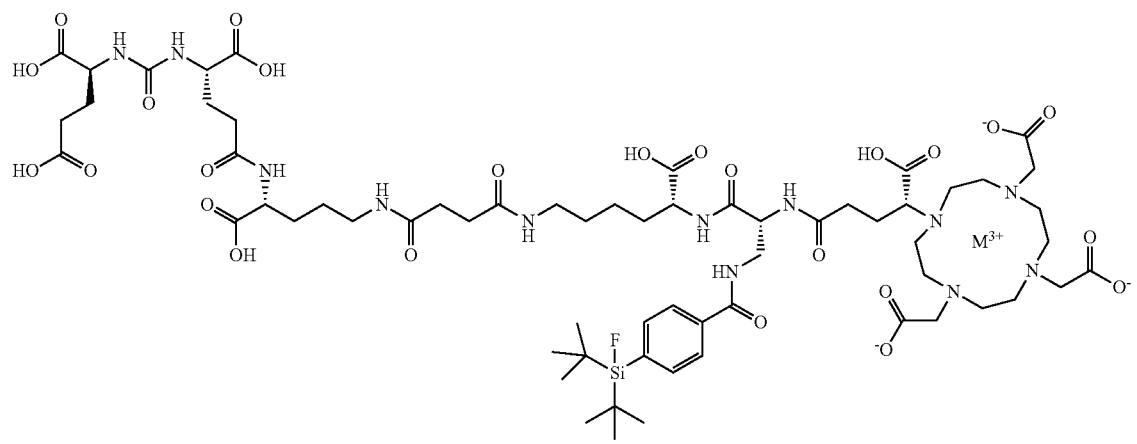
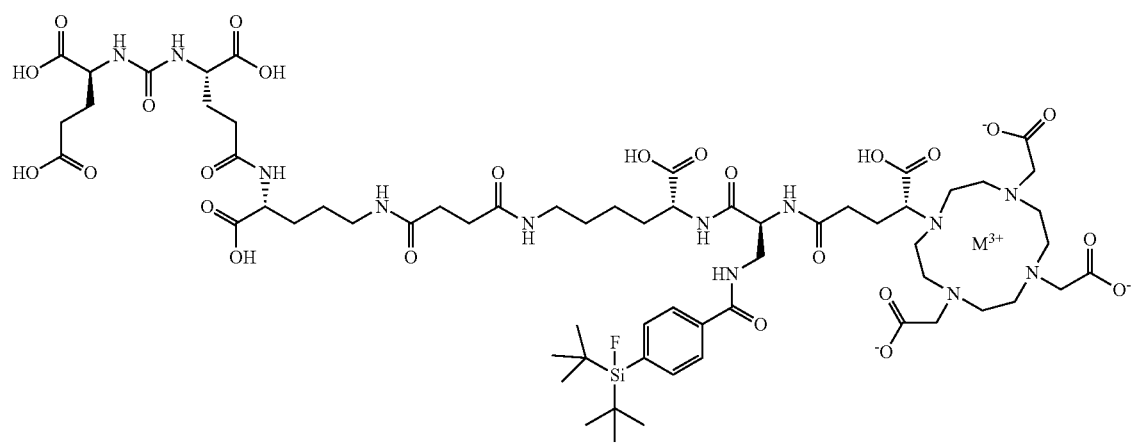

PSMA-SIFA4 (8)
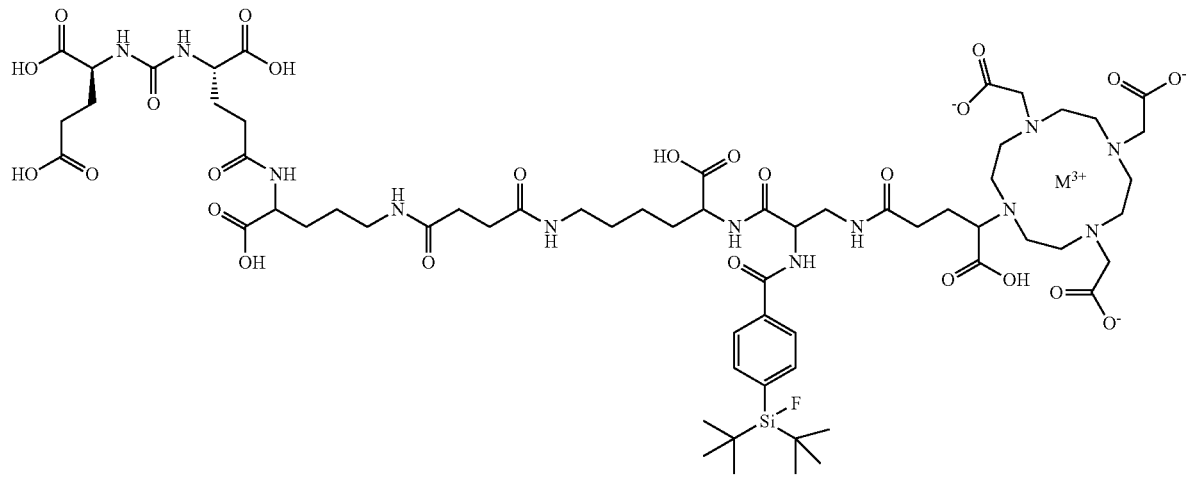
and isomers thereof
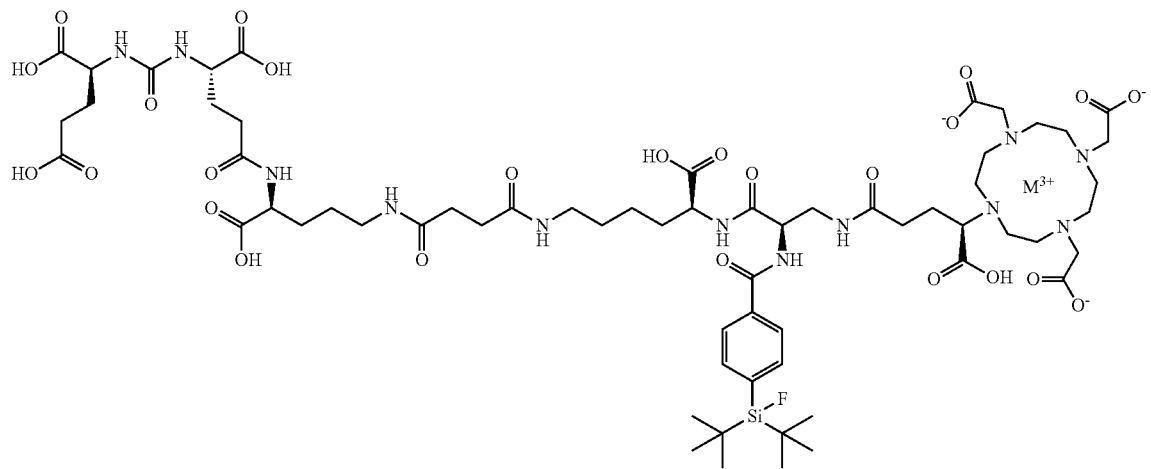
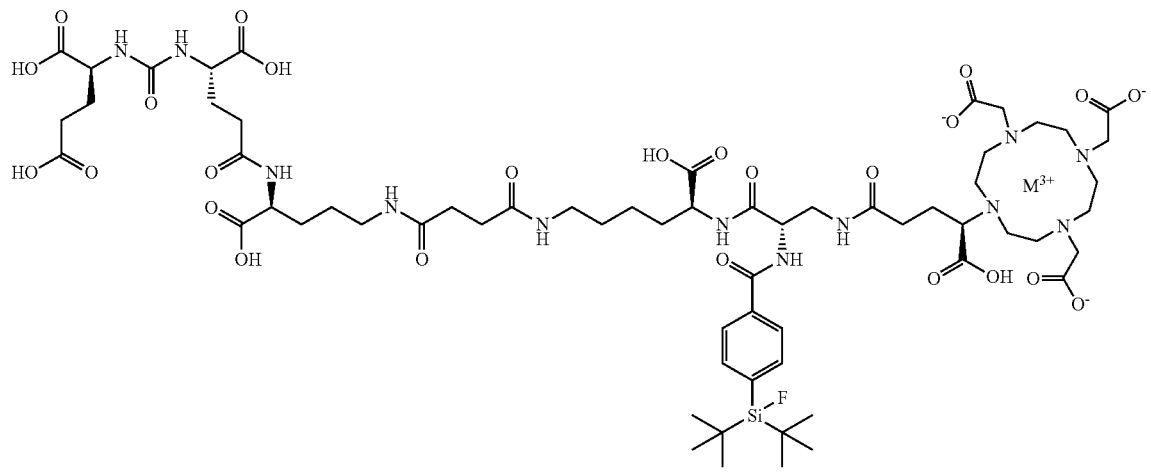

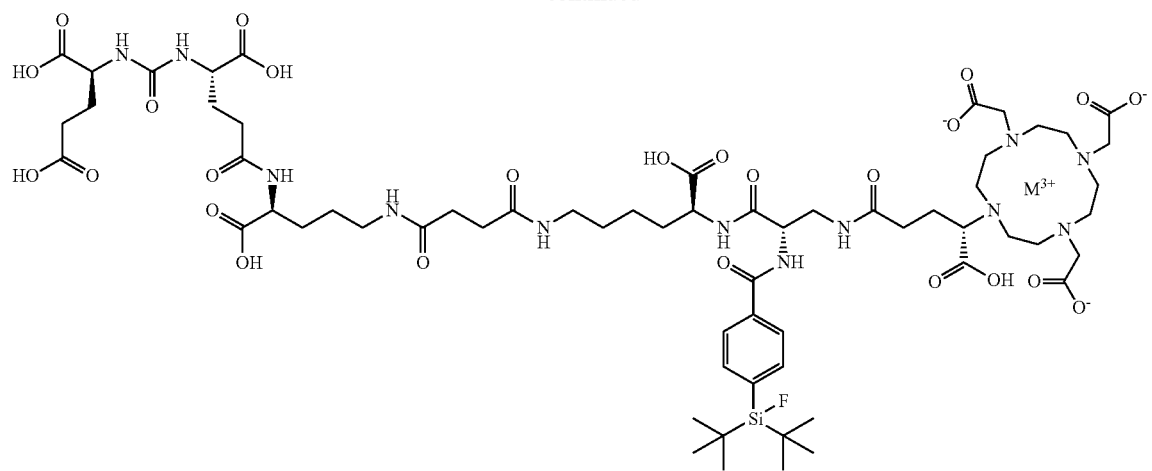
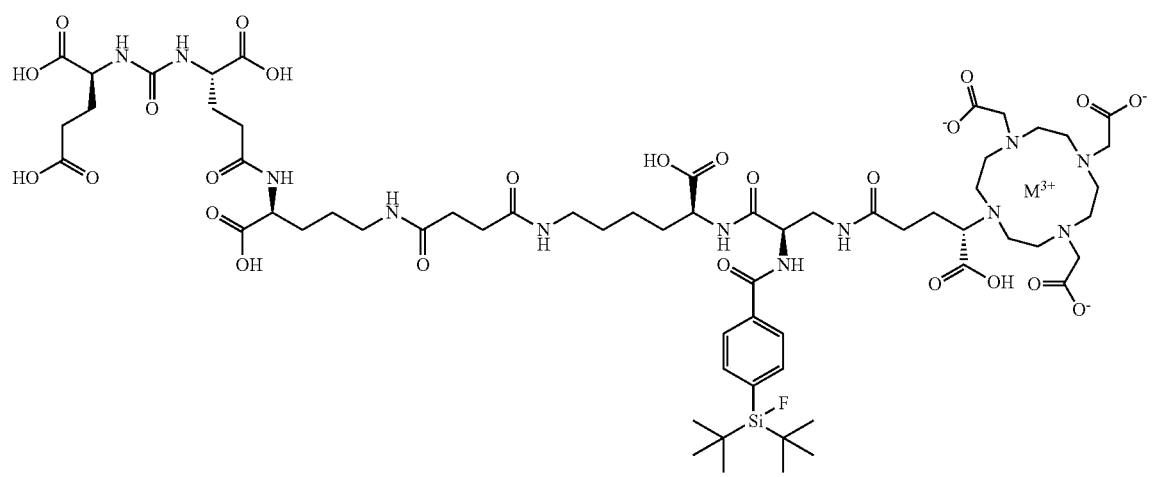
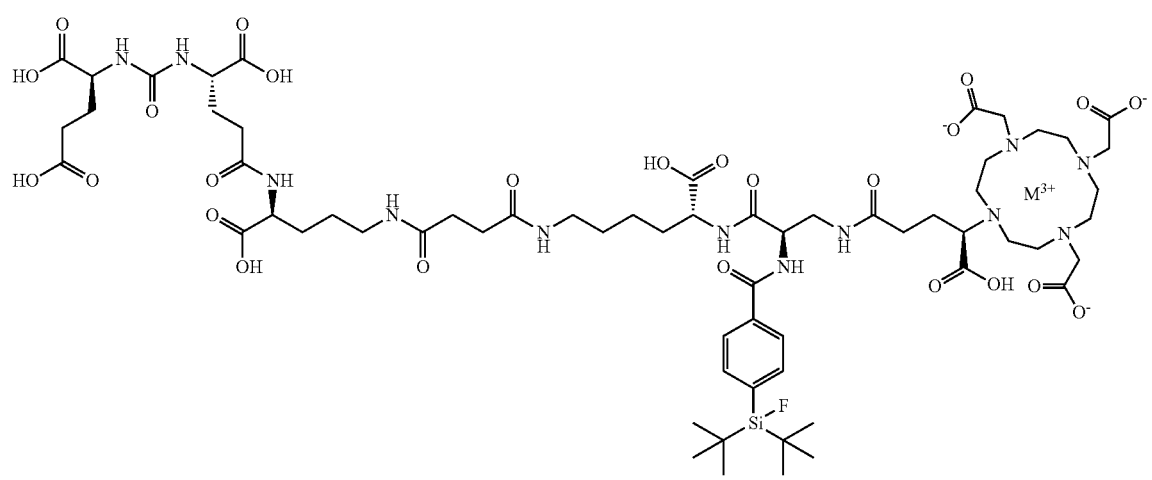

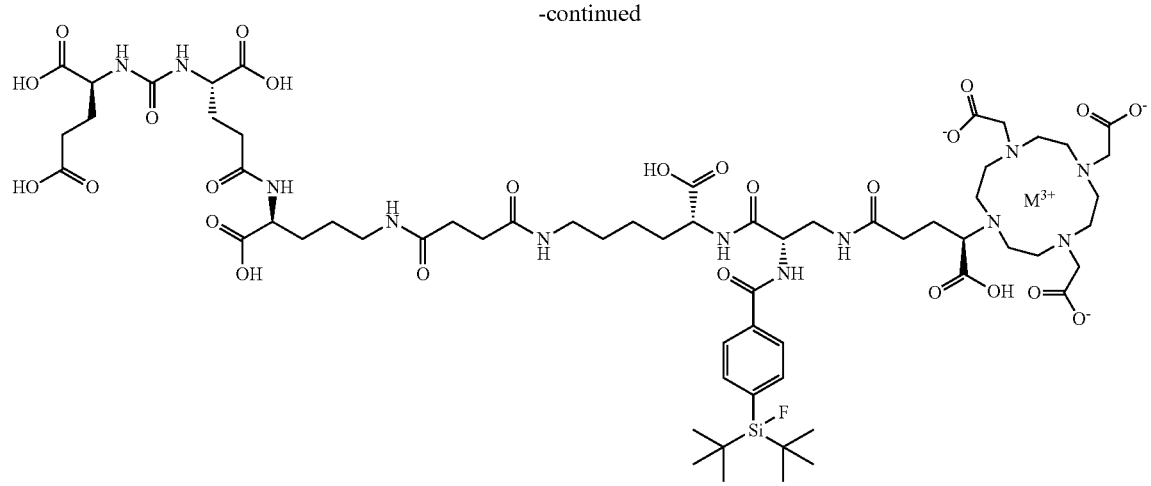
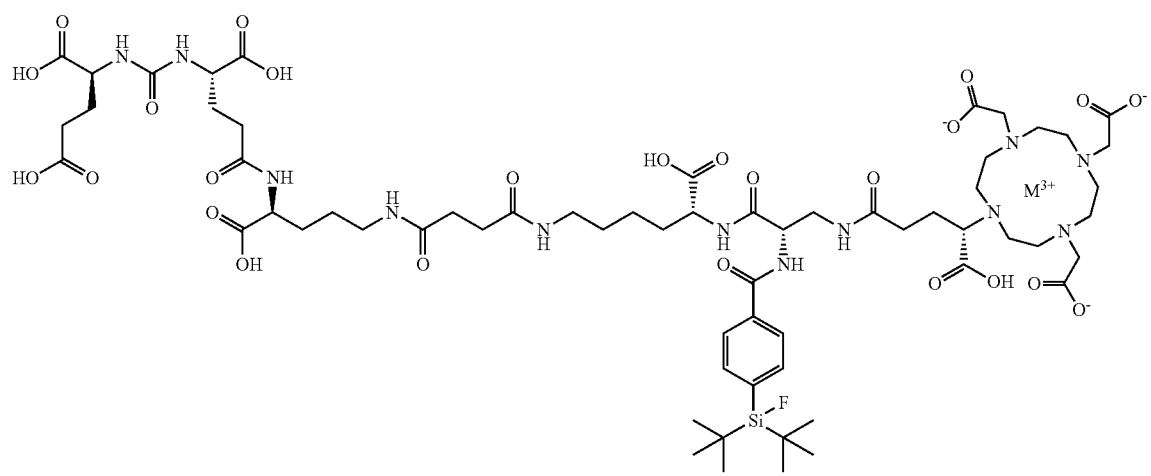
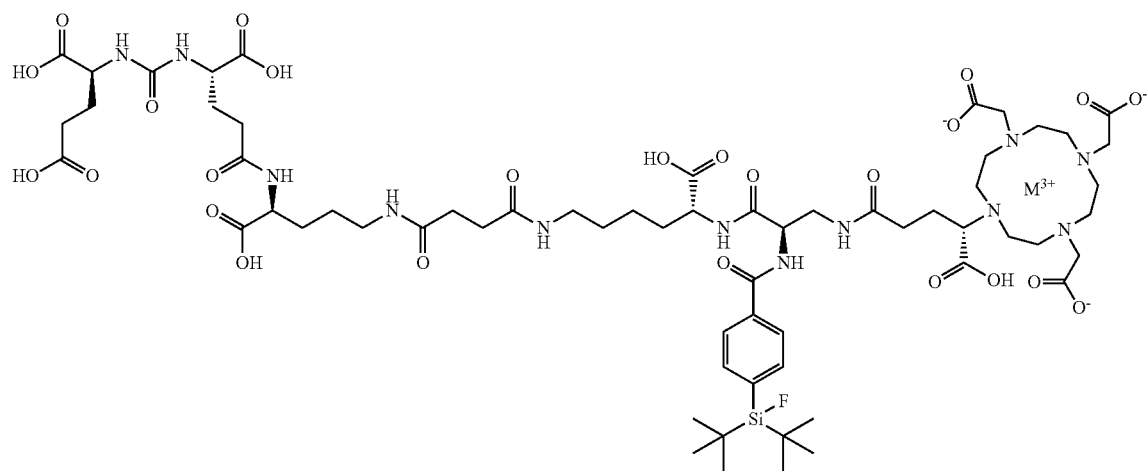

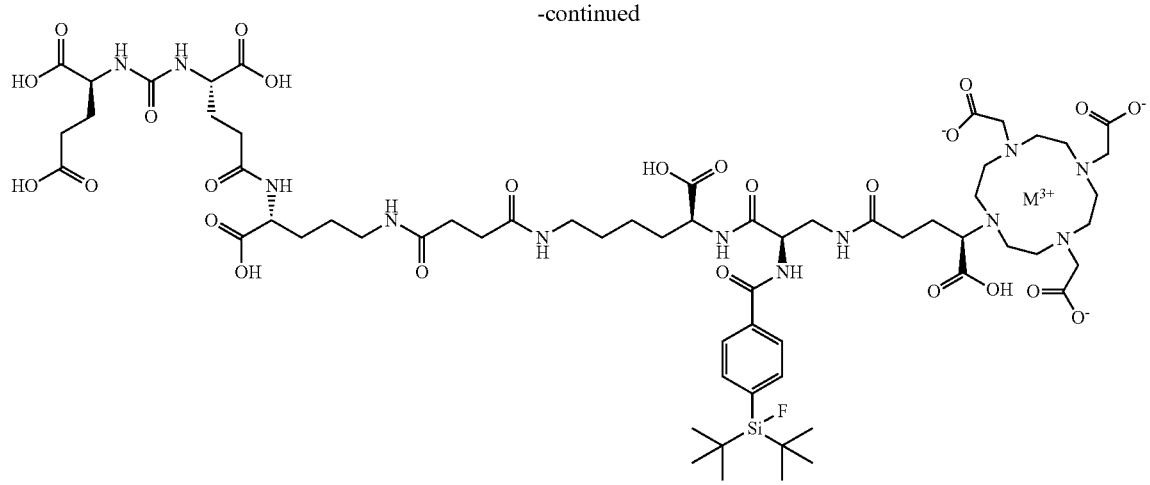
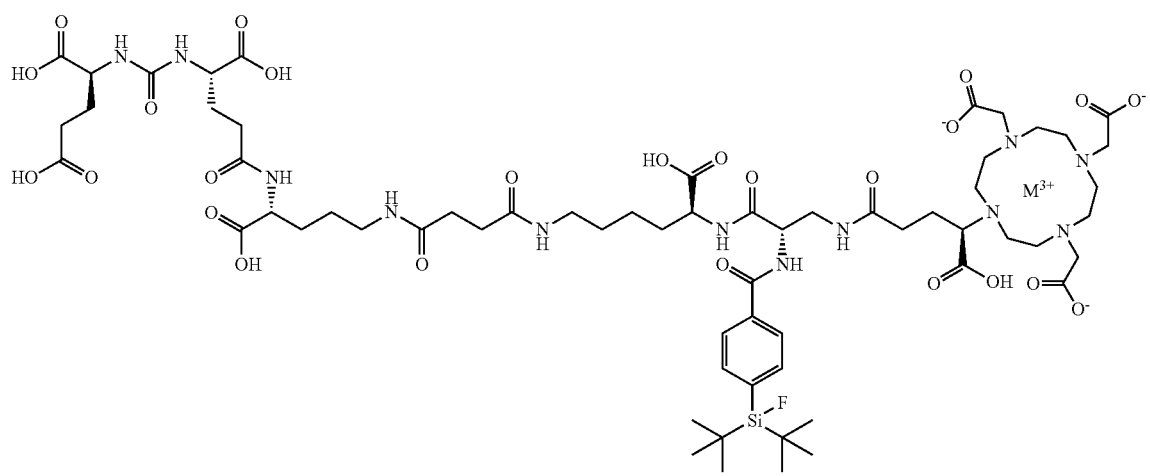
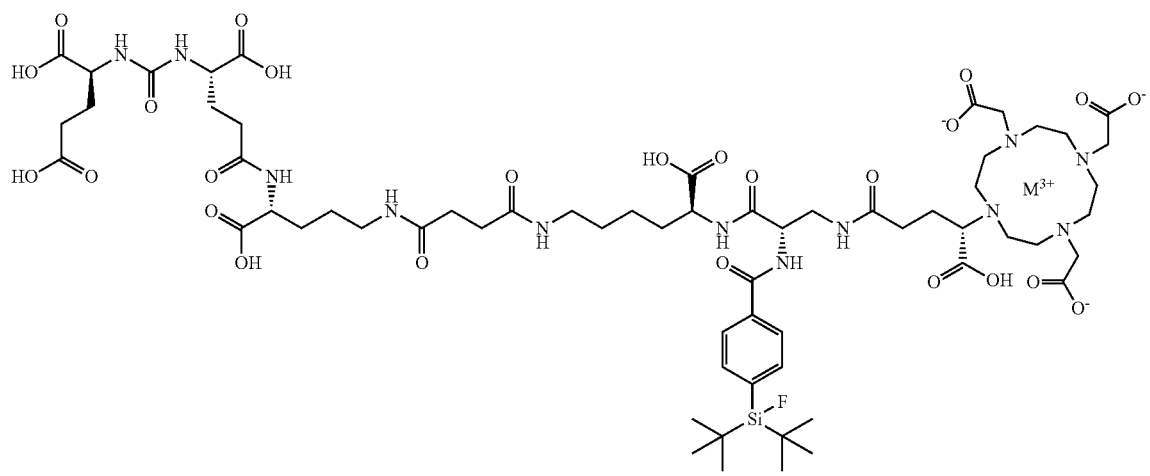

-continued
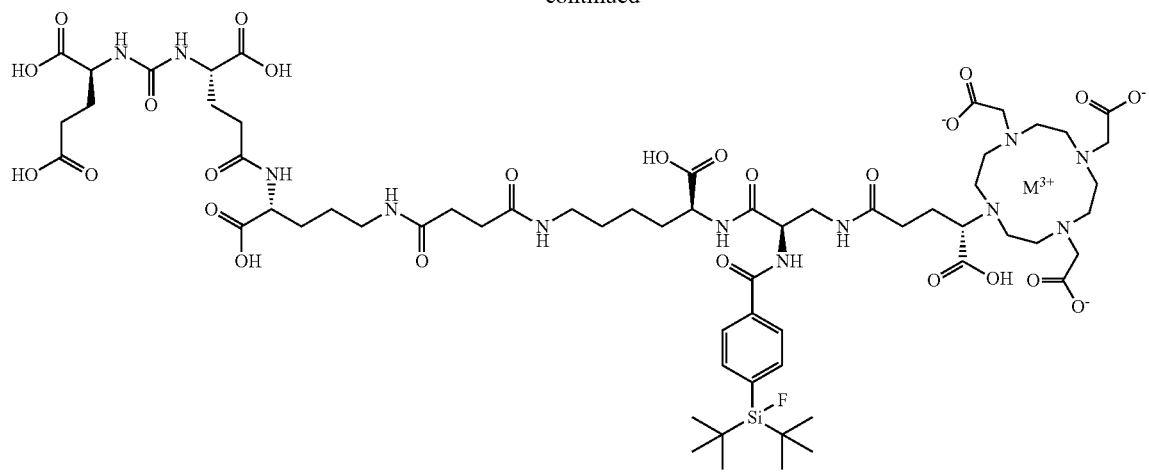
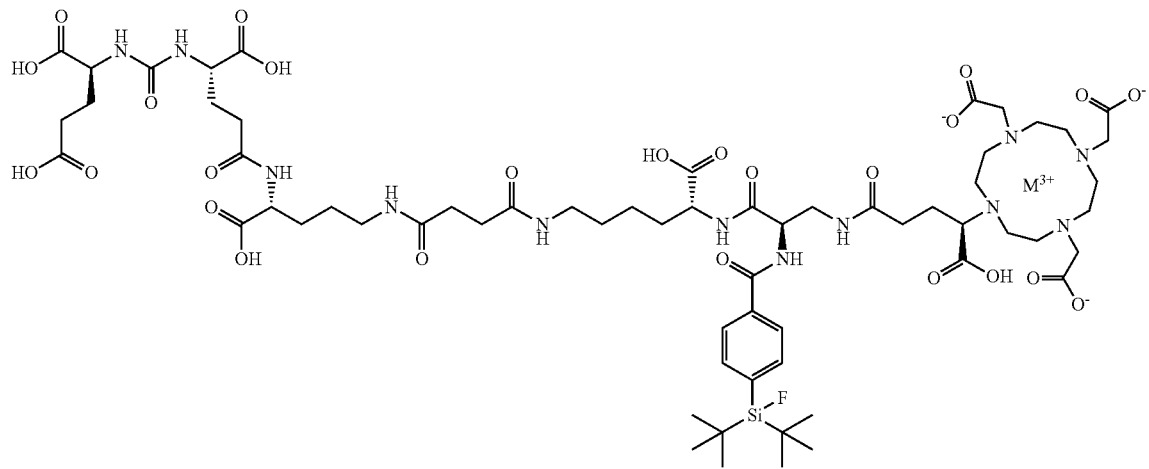
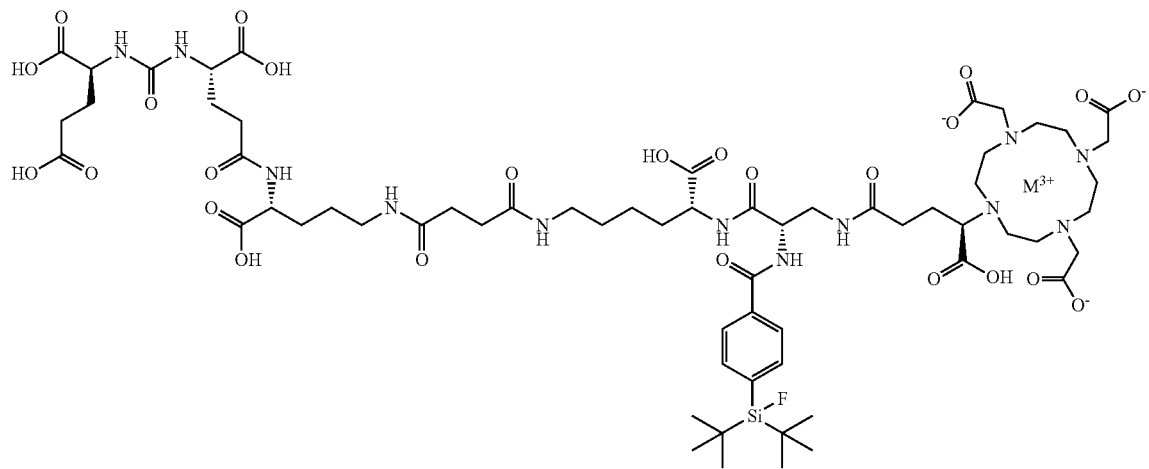

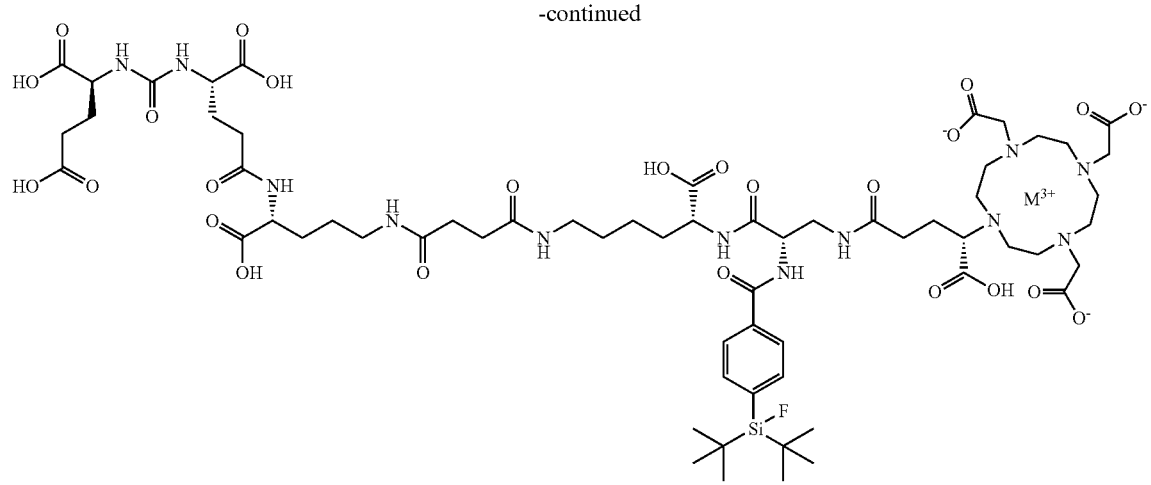
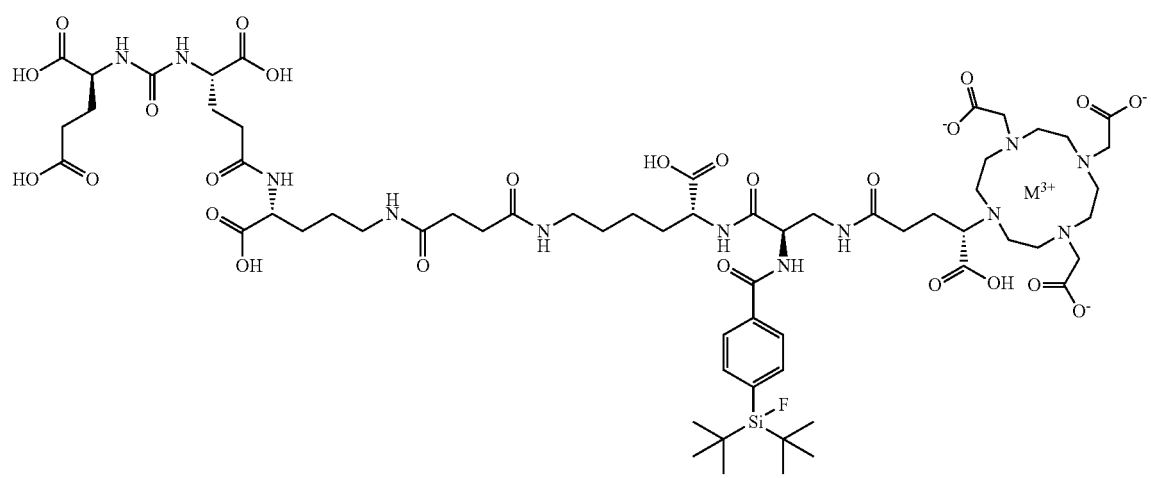
PSMA-SIFA5 (9)
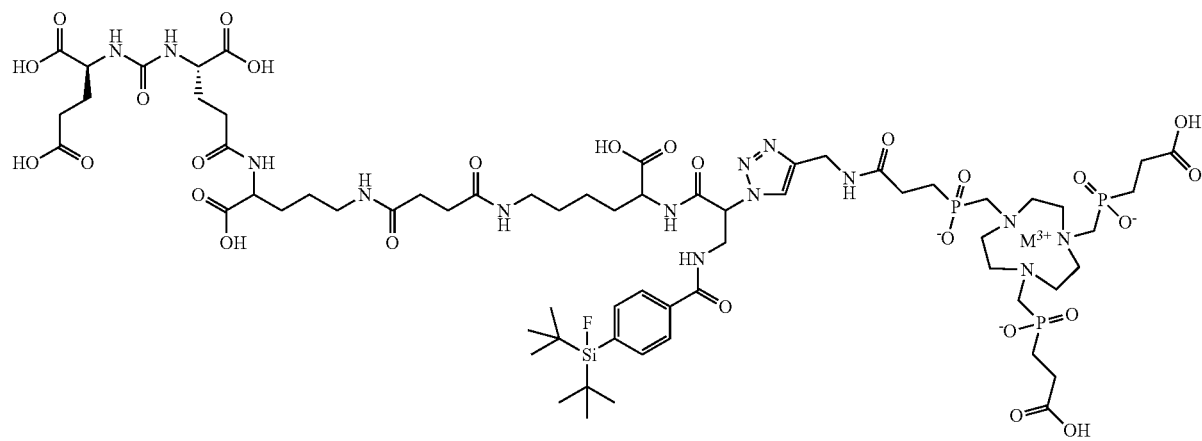

and isomers thereof
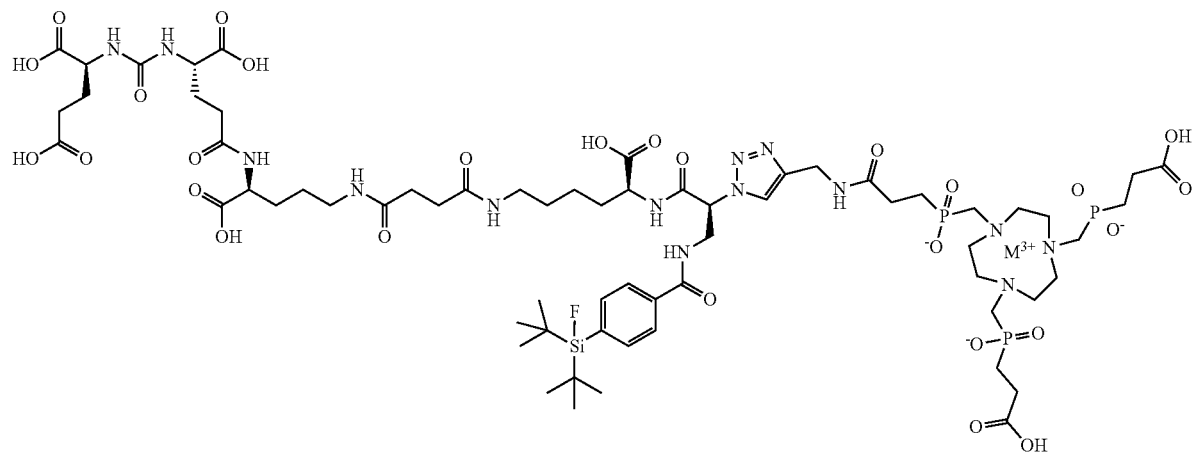
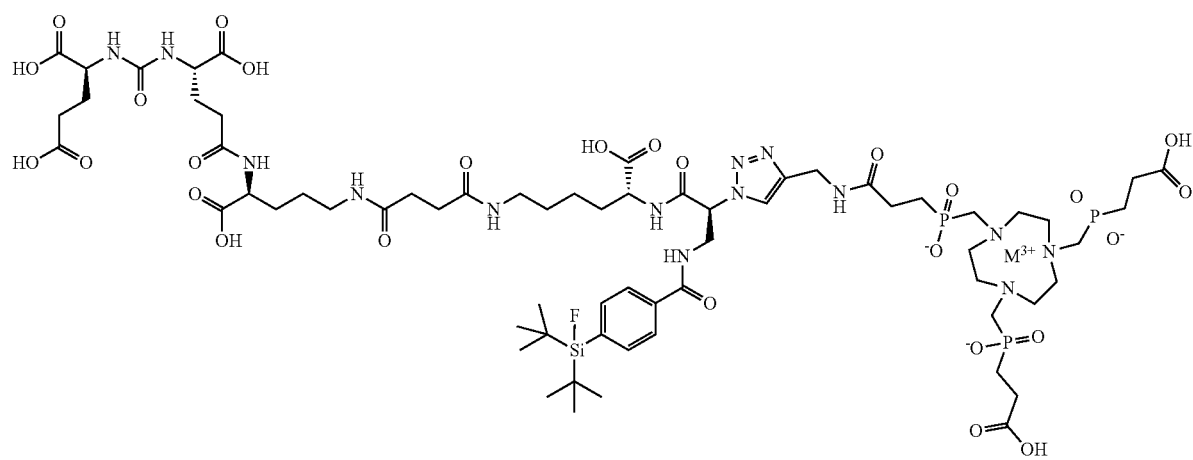
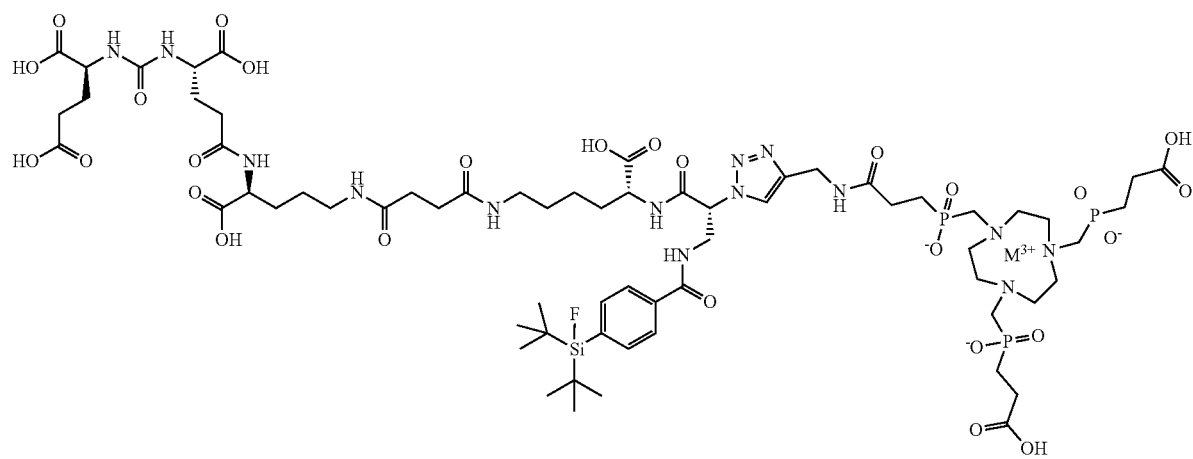

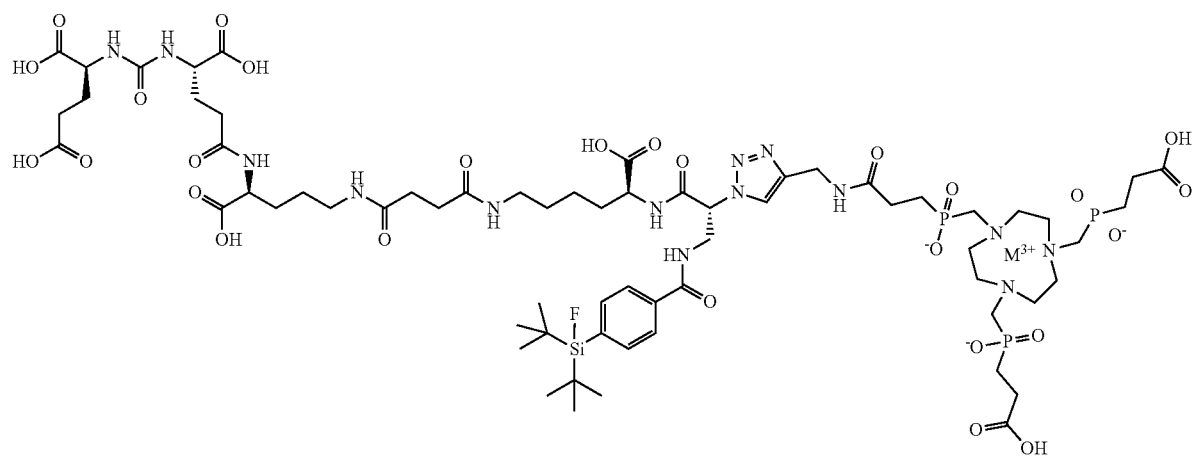
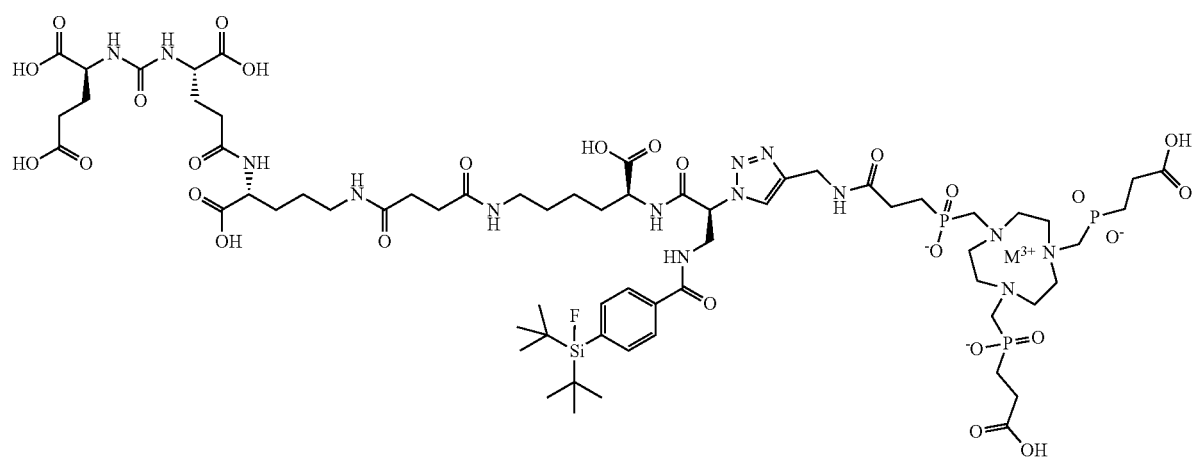
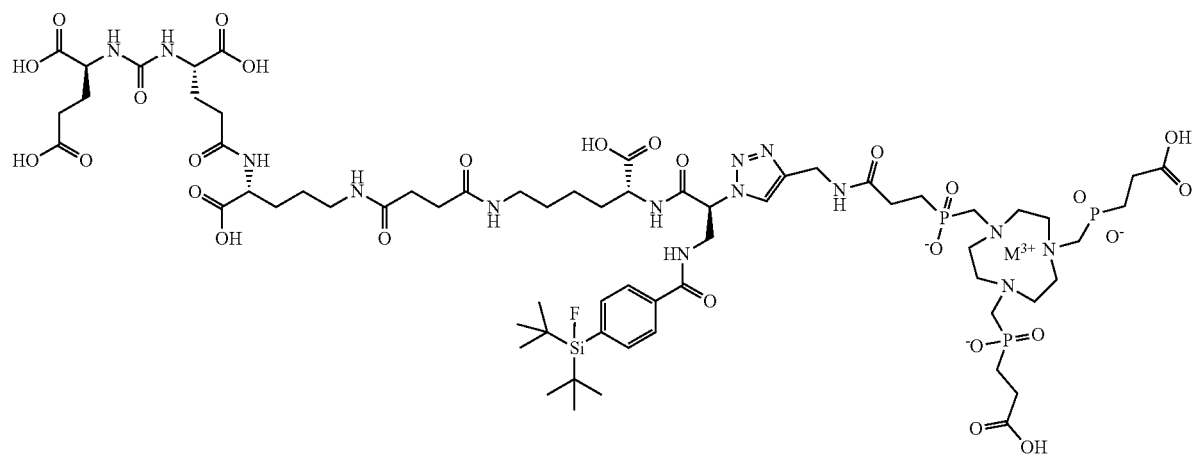

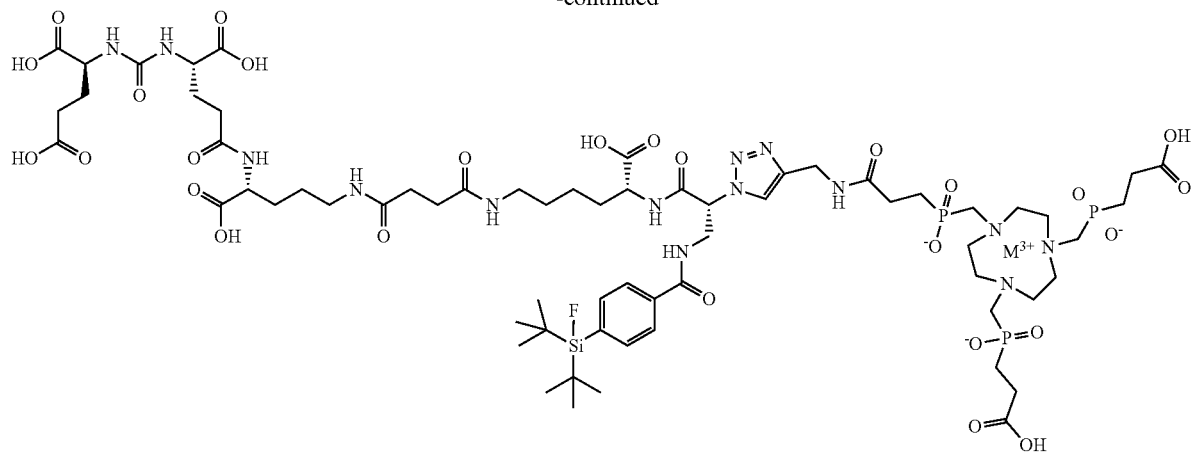
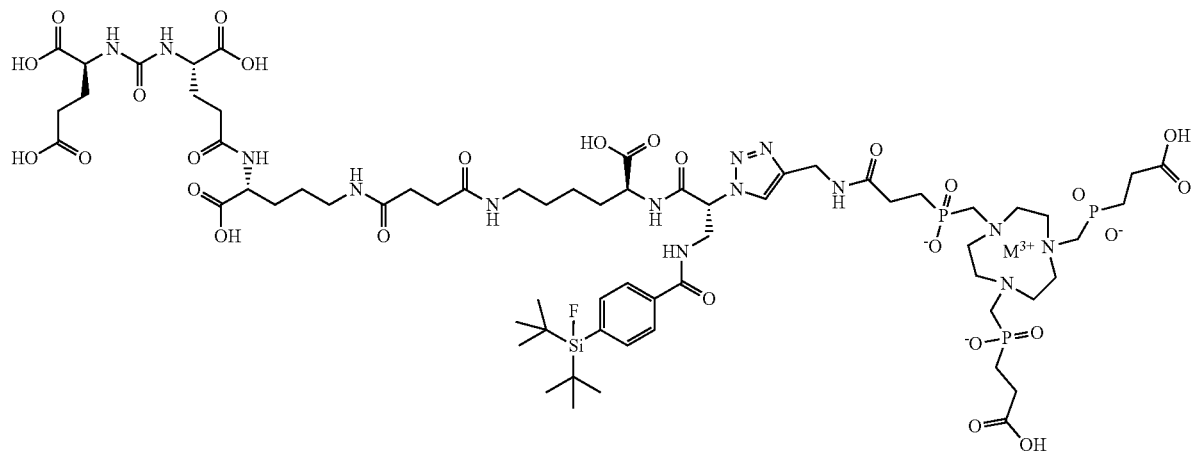
PSMA-SIFA 10
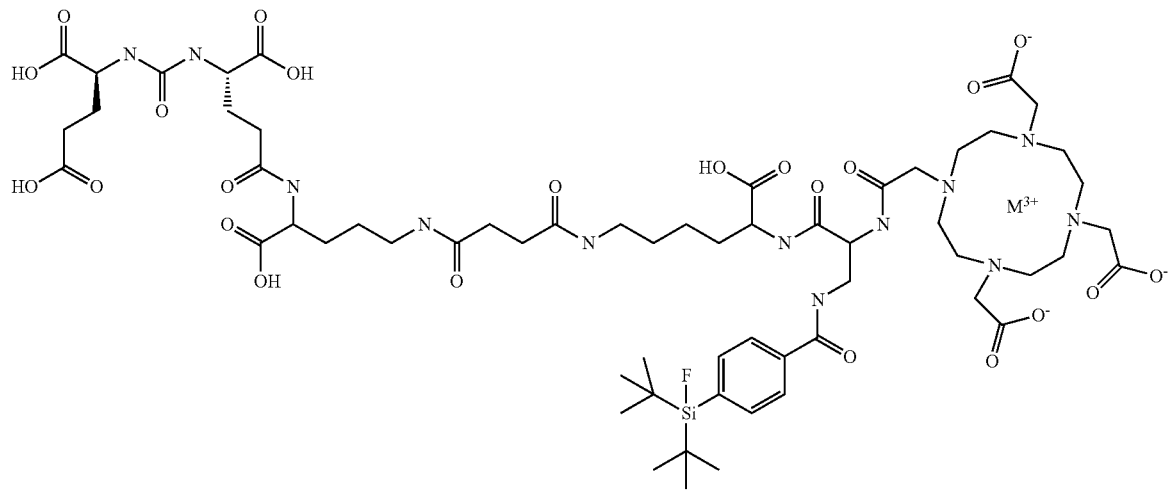 [SMILES: CC(C)(C)[Si](F)(c1ccc(C(=O)NCC(NC(=O)CN2CCN(CC(=O)[O-])CCN(CC(=O)[O-])CCN(CC(=O)[O-])CC2)C(=O)NC(CCCCNC(=O)CCC(=O)NCCCC(NC(=O)CC[C@H](NC(=O)N[C@@H](CCC(=O)O)C(=O)O)C(=O)O)C(=O)O)C(=O)O)cc1)C(C)(C)C ; "M3+"]

and isomers thereof:
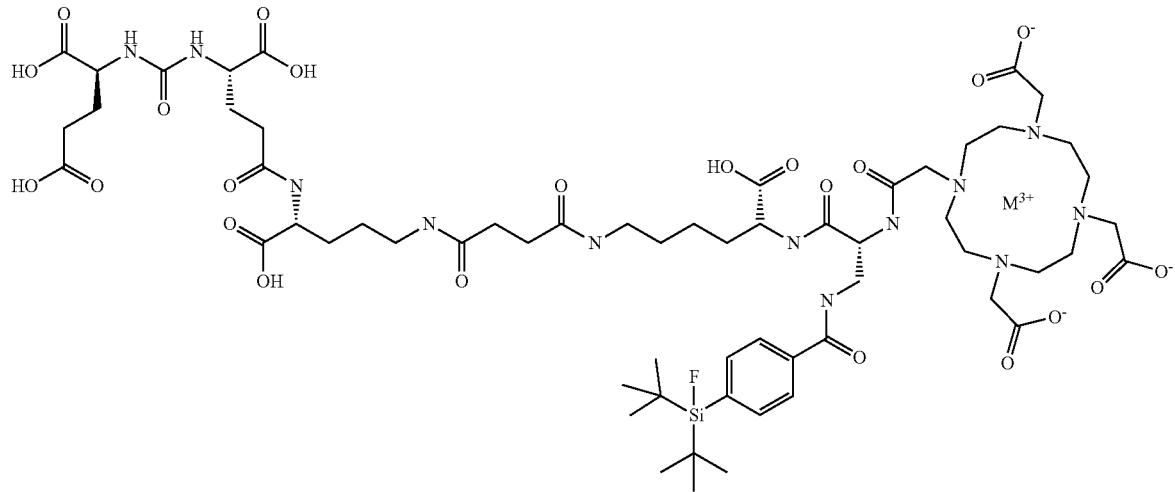
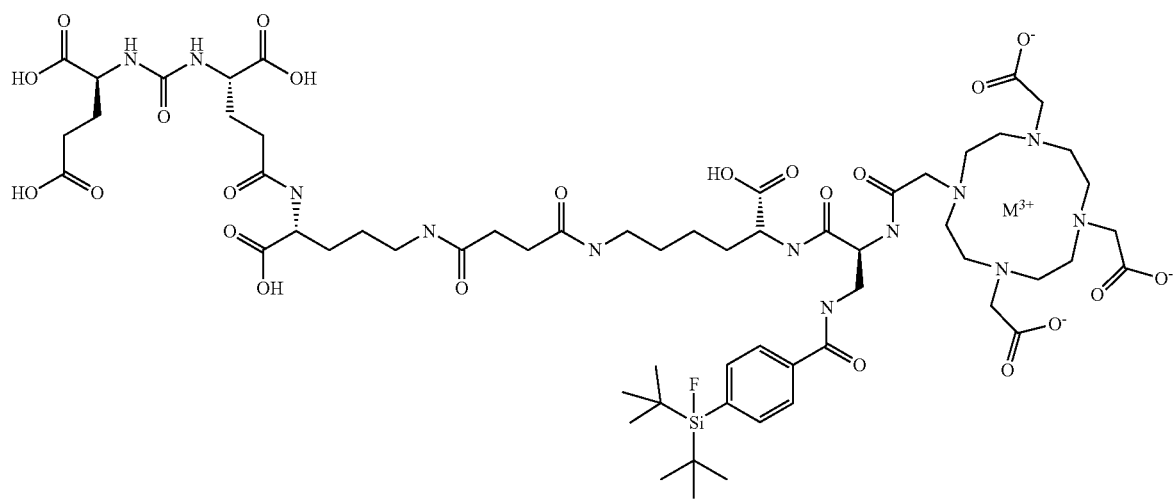
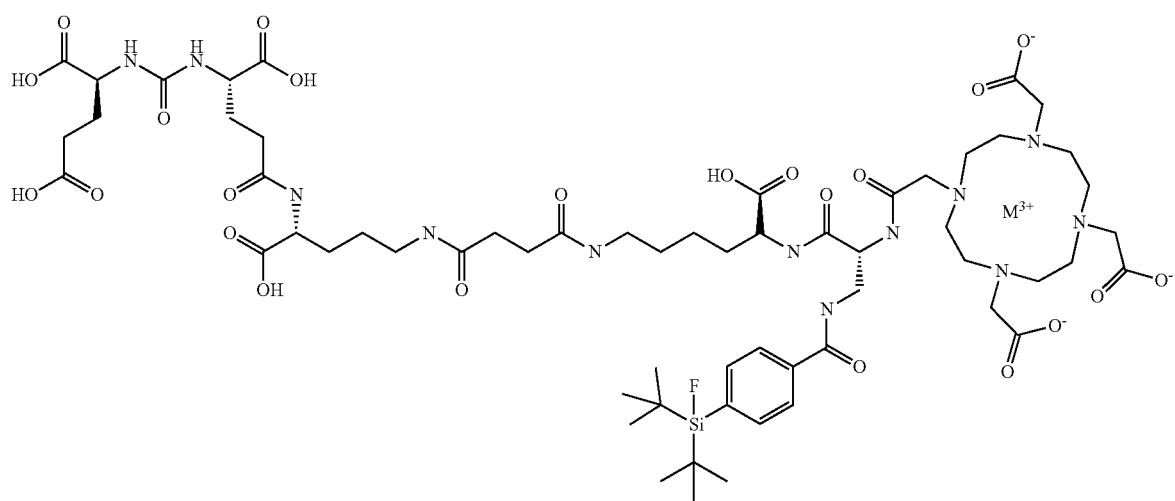

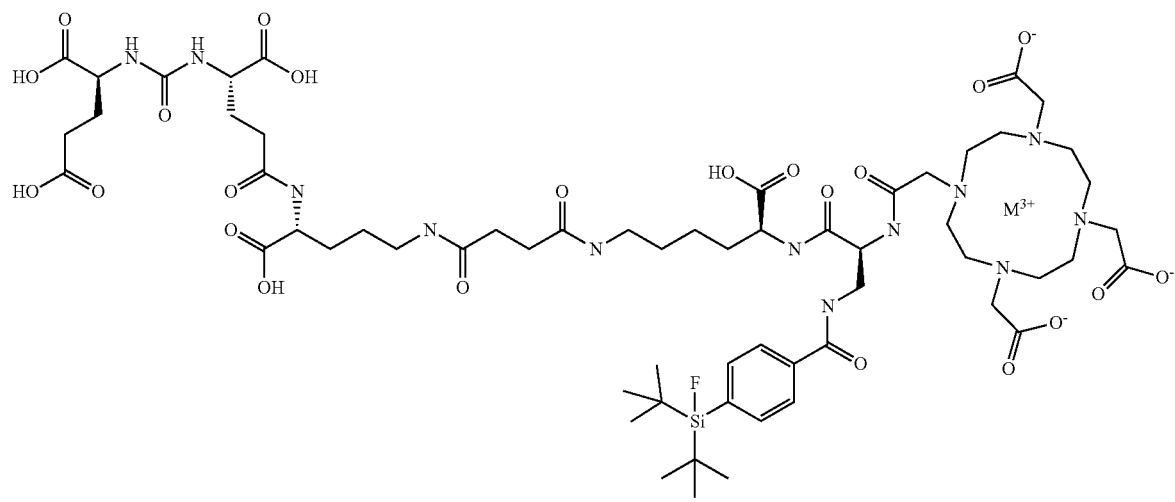
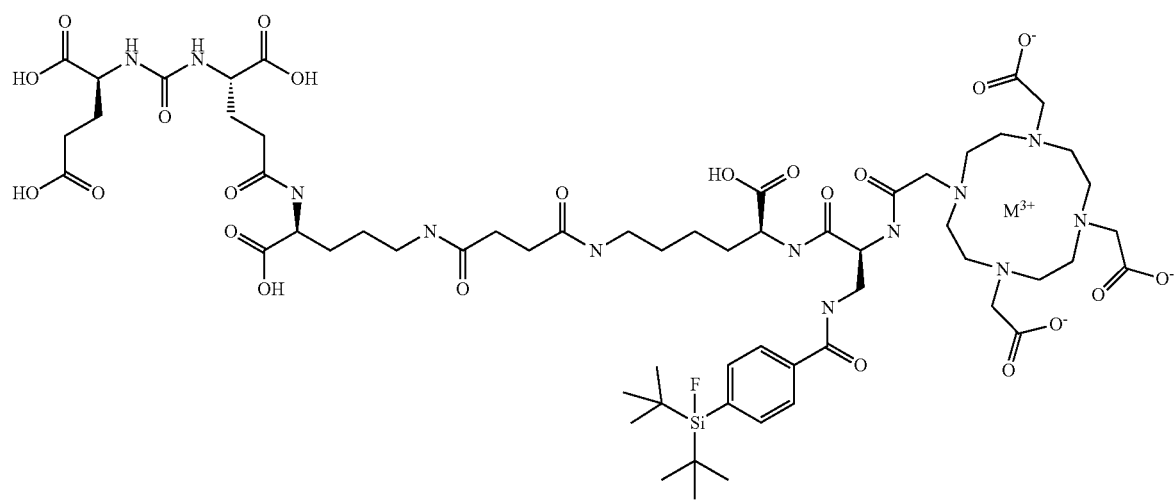
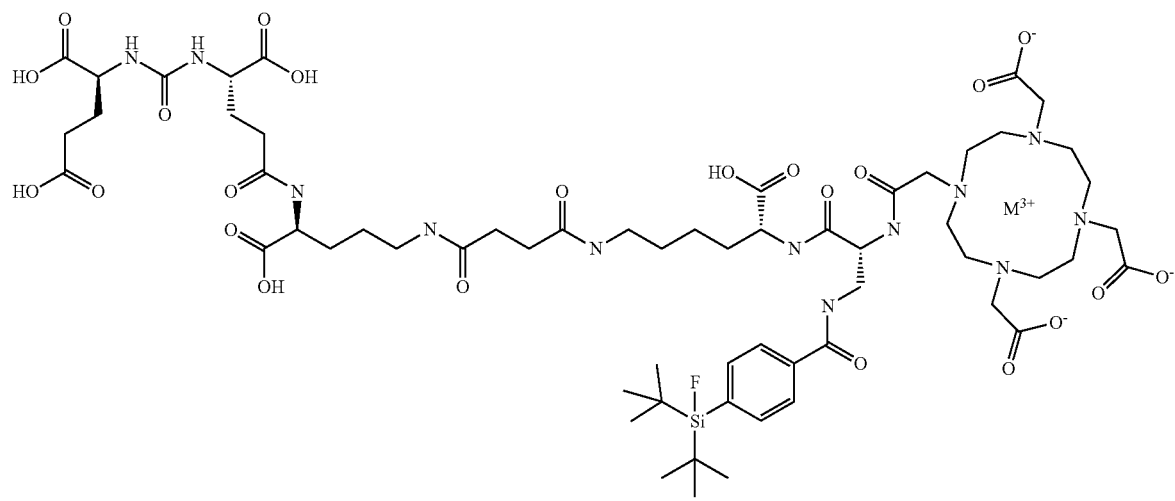

-continued
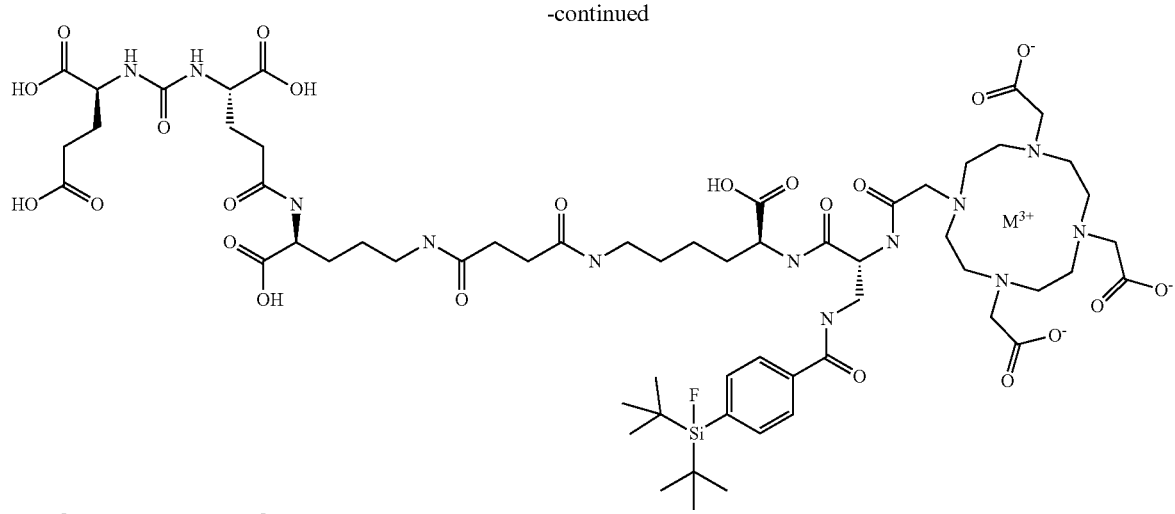
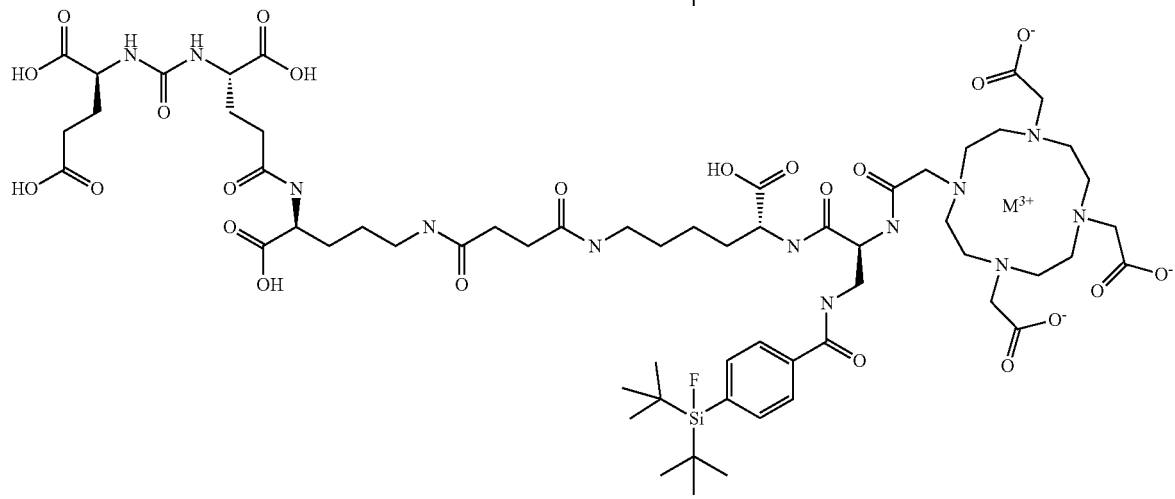
40
PSMA-SIFA 11
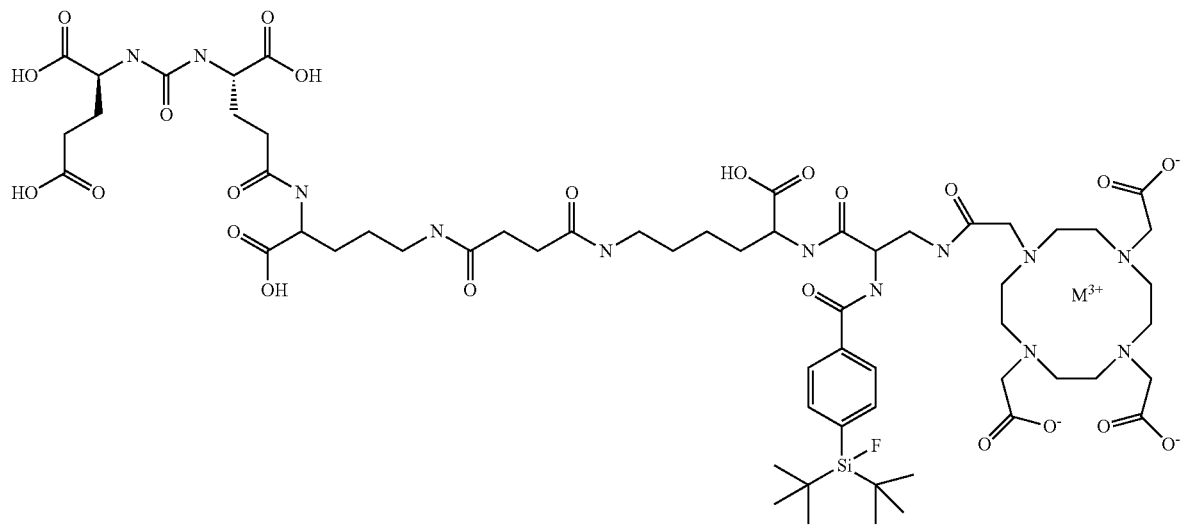 [SMILES: CC(C)(C)[Si](F)(c1ccc(C(=O)NC(CNC(=O)CN2CCN(CC(=O)[O-])CCN(CC(=O)[O-])CCN(CC(=O)[O-])CC2)C(=O)NC(CCCCNC(=O)CCC(=O)NCCCC(NC(=O)CC[C@H](NC(=O)N[C@@H](CCC(=O)O)C(=O)O)C(=O)O)C(=O)O)C(=O)O)cc1)C(C)(C)C ; "M3+"]

and isomers thereof:
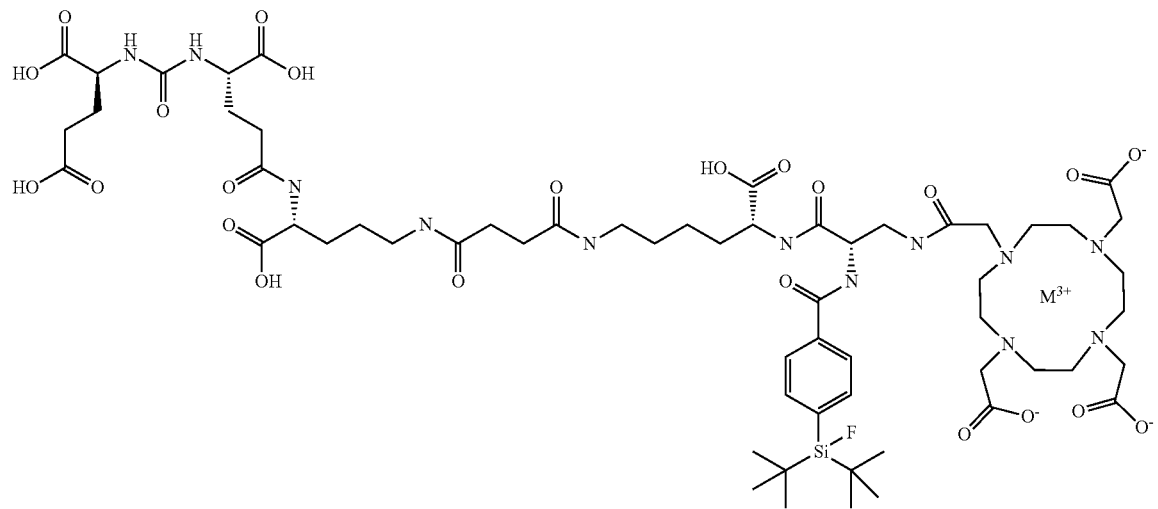
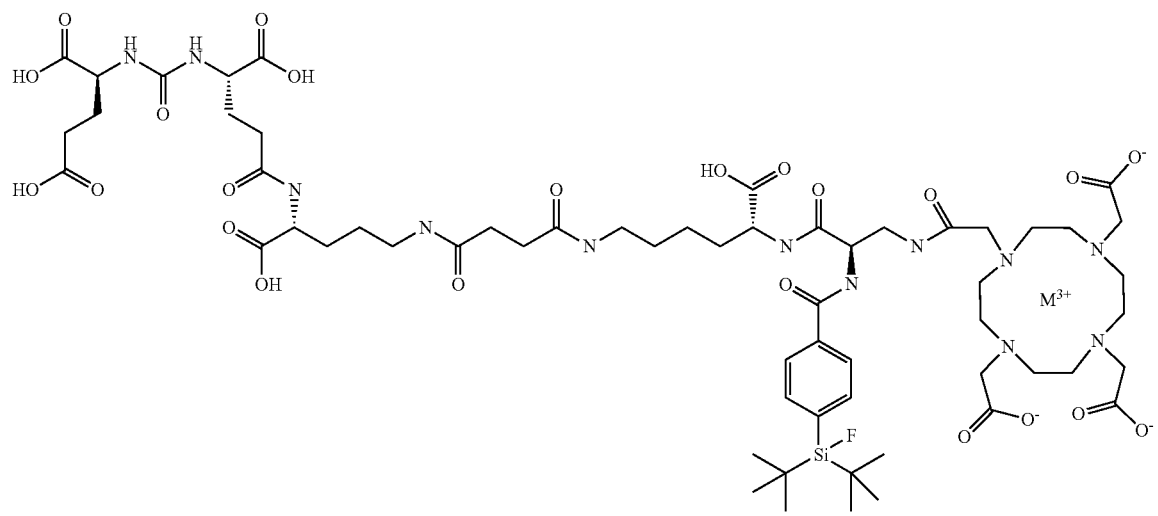
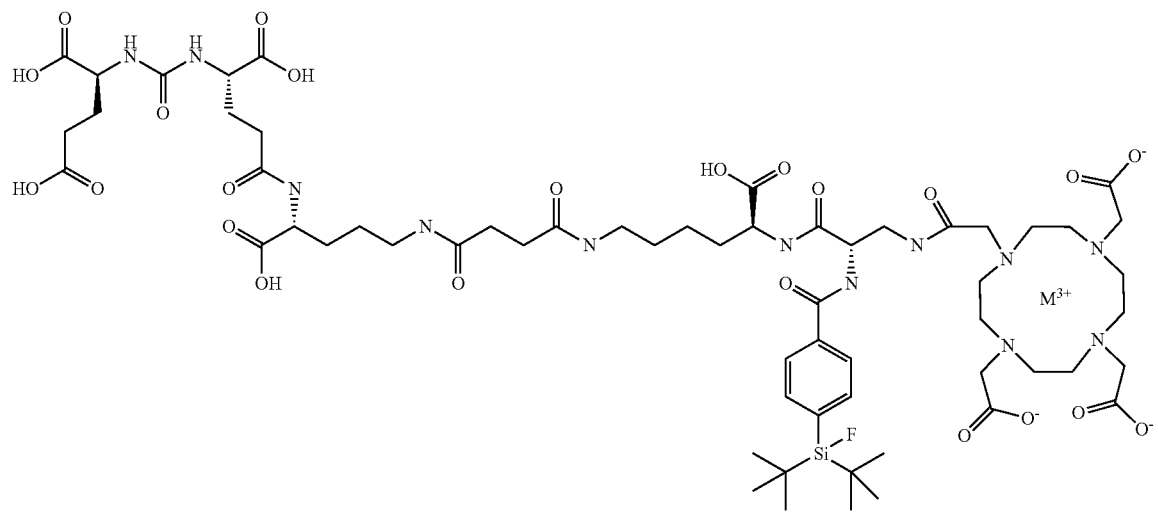

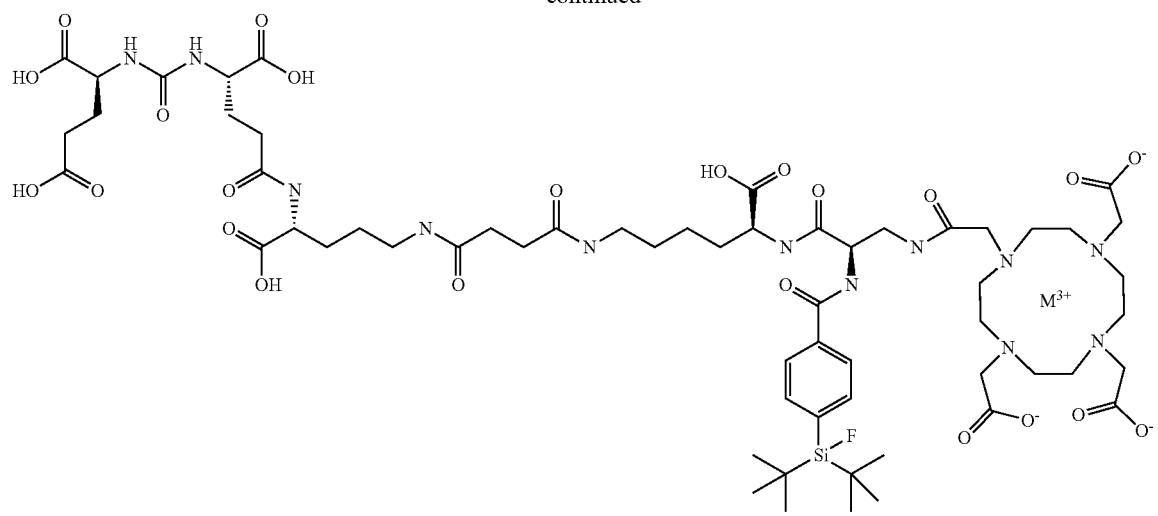
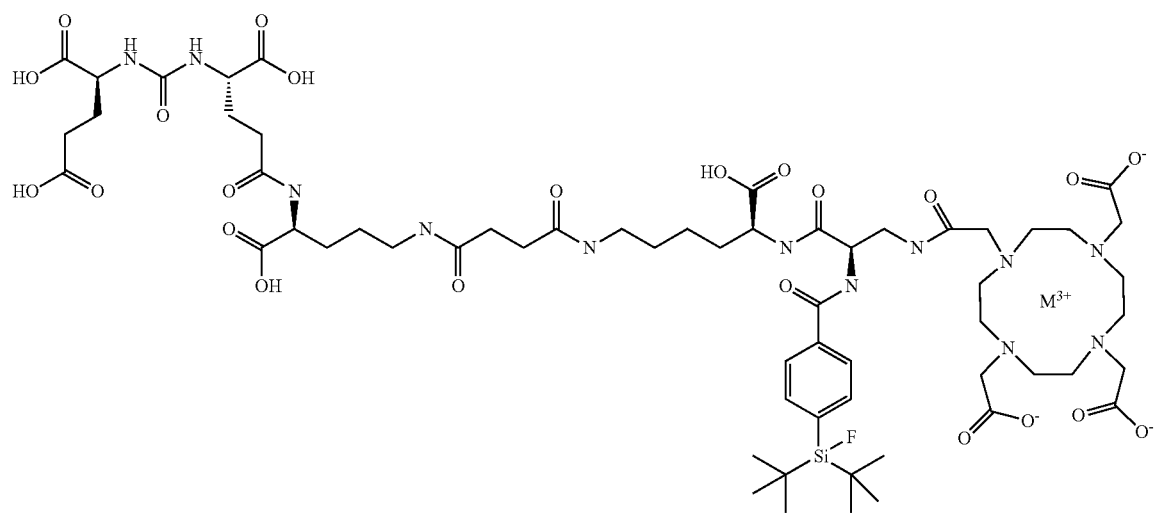
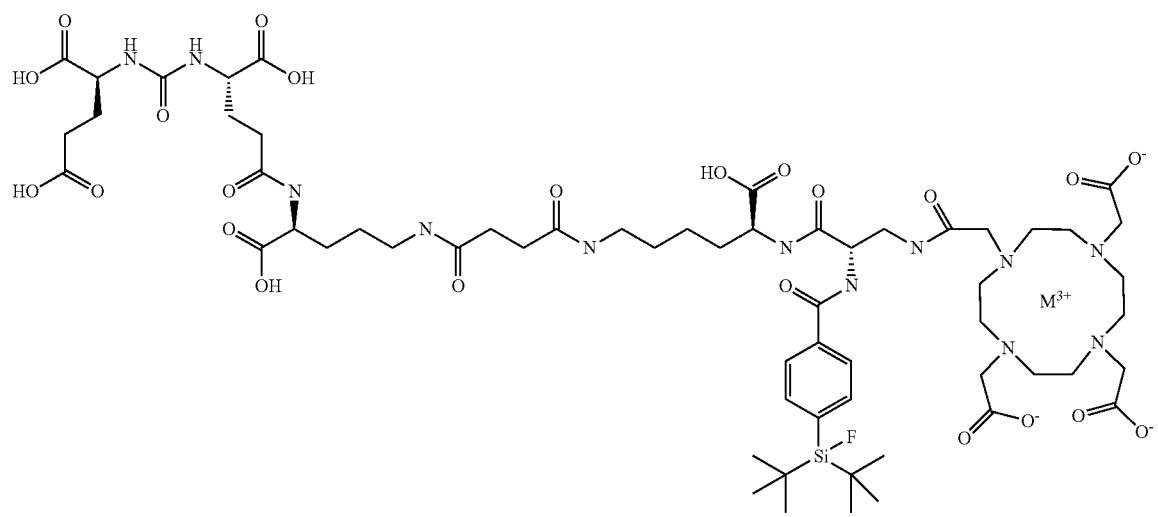

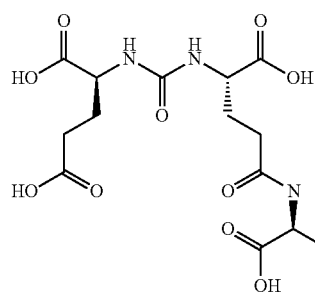
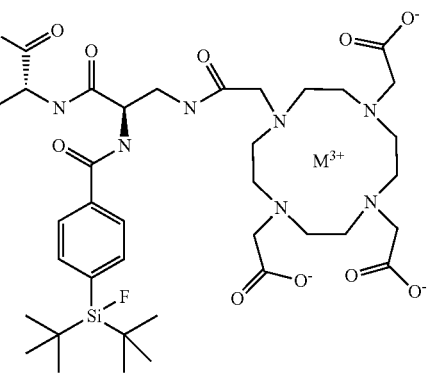
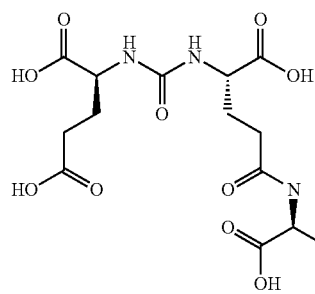
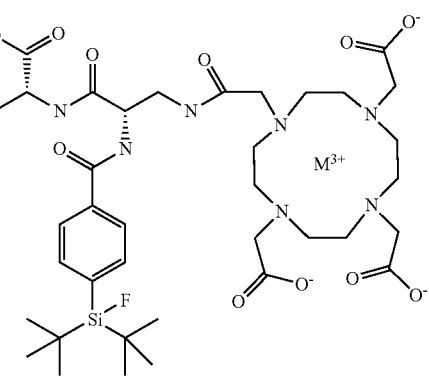

Preferred labelling schemes for these most preferred compounds are as defined herein above.

In a further aspect, the present invention provides a pharmaceutical imaging composition comprising or consisting of one or more conjugates or compounds of the invention as disclosed herein above.

In a further aspect, the present invention provides a diagnostic composition comprising or consisting of one or more conjugates or compounds of the invention as disclosed herein above.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc.

Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 0.1 ng and 10 mg/kg body weight per dose; however, doses below or above this exemplary range are envisioned, especially considering the aforementioned factors.

In a further aspect, the present invention provides one or more compounds of the invention as disclosed herein above for use in diagnostic medicine.

Preferred uses in medicine are in nuclear medicine such as nuclear diagnostic imaging, also named nuclear molecular imaging, and/or targeted radiotherapy of diseases associated with an overexpression, preferably of PSMA on the diseased tissue.

In a further aspect, the present invention provides a compound of the invention as defined herein above for use in a method of diagnosing and/or staging cancer, preferably prostate cancer. Prostate cancer is not the only cancer to express PSMA. Nonprostate cancers to demonstrate PSMA expression include breast, lung, colorectal, and renal cell carcinoma. Thus any compound described herein having a PSMA binding moiety can be used in the diagnosis, imaging or treatment of a cancer having PSMA expression.

Preferred indications are the detection or staging of cancer, such as, but not limited high grade gliomas, lung cancer and especially prostate cancer and metastasized prostate cancer, the detection of metastatic disease in patients with primary prostate cancer of intermediate-risk to high-risk, and the detection of metastatic sites, even at low serum PSA values in patients with biochemically recurrent prostate cancer. Another preferred indication is the imaging and visualization of neoangiogensis.

In a further aspect, the present invention provides a conjugate or compound of the invention as defined herein above for use in a method of diagnosing and/or staging cancer, preferably prostate cancer.

The Figures illustrate:

FIG. 1: Exemplary correlation of determination of the nine reference substances in OriginPro 2016G.

Figure 2A:
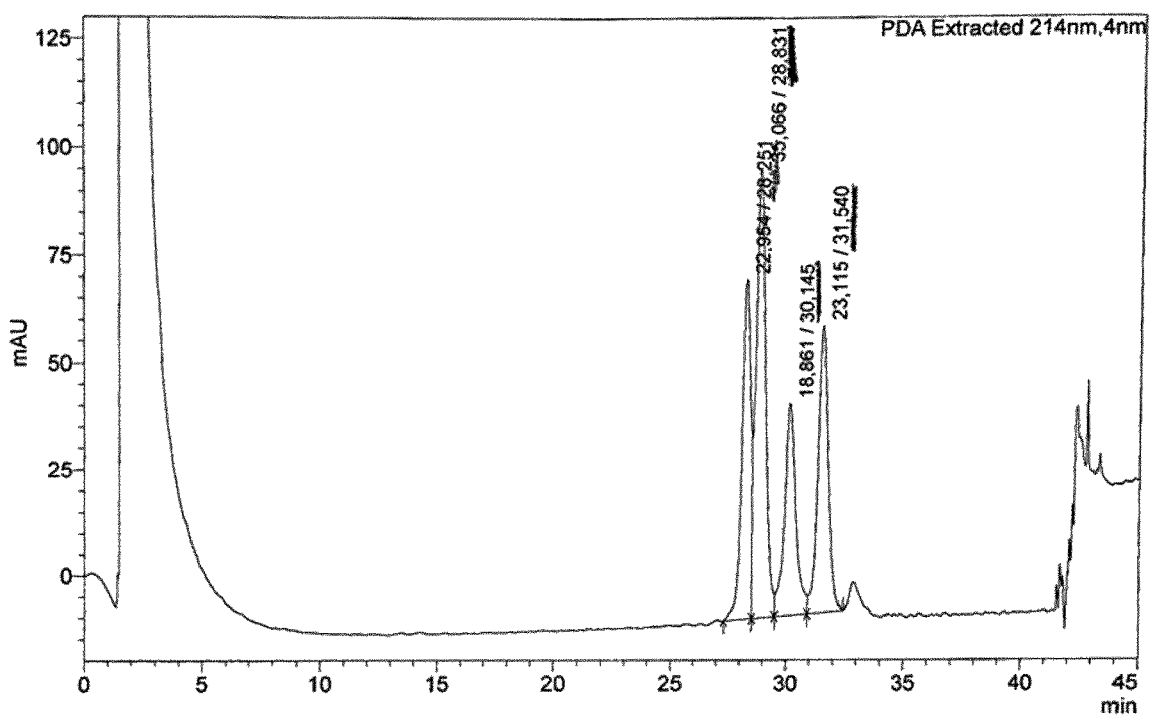
Figure 2B:
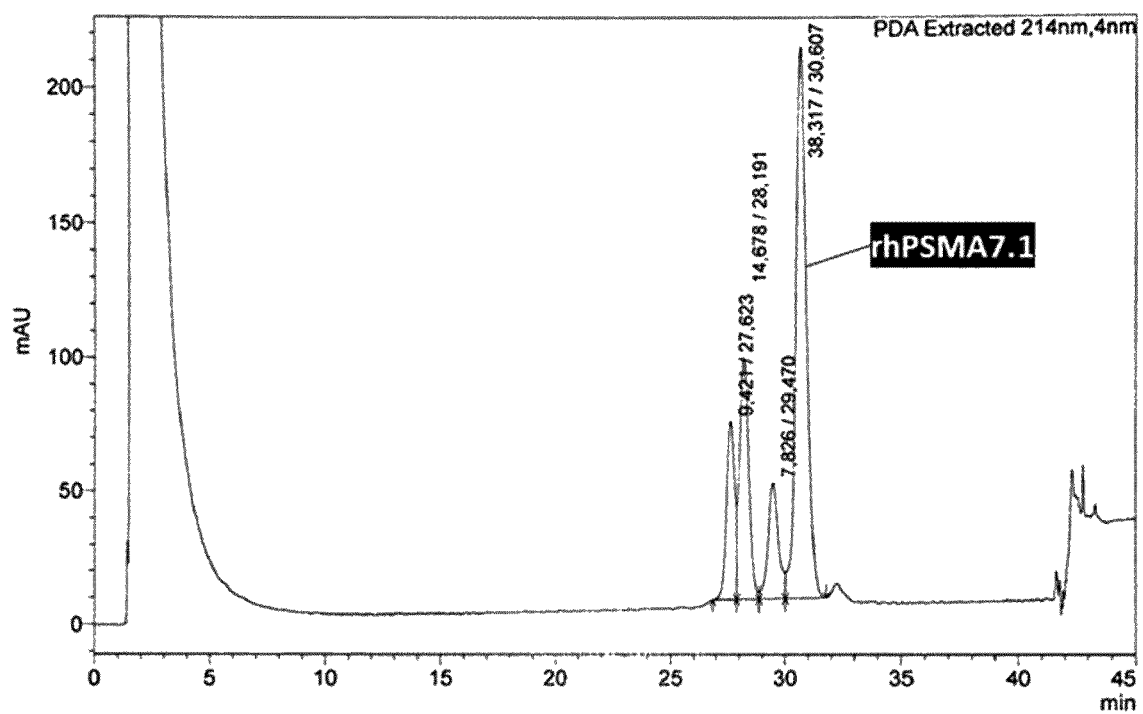
Figure 2C:
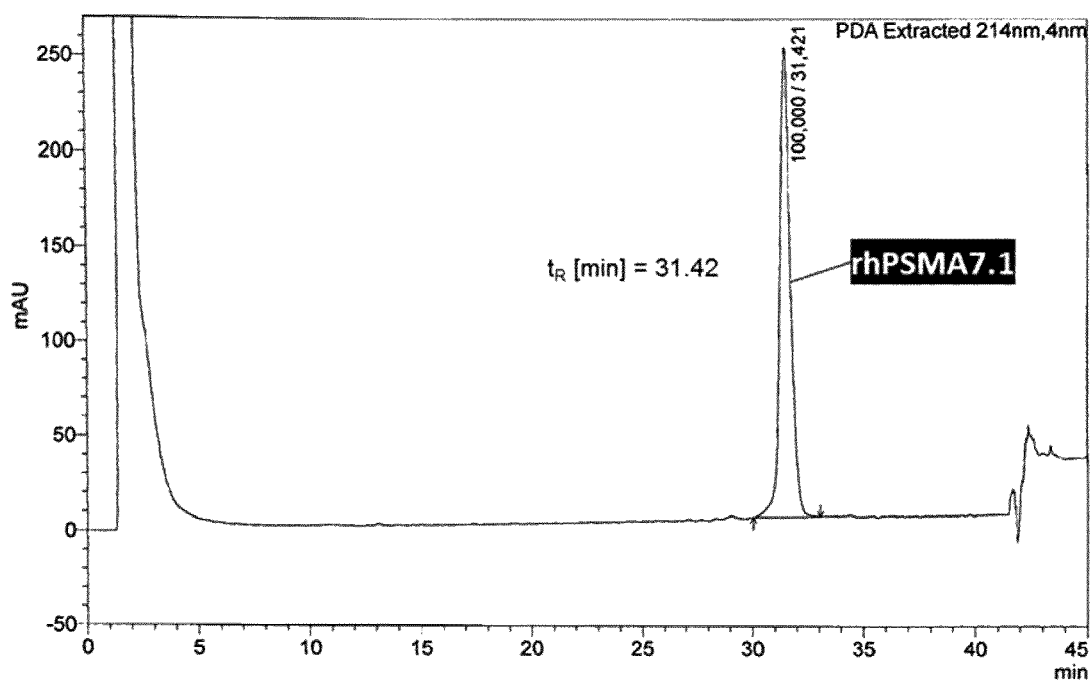
Figure 3A:
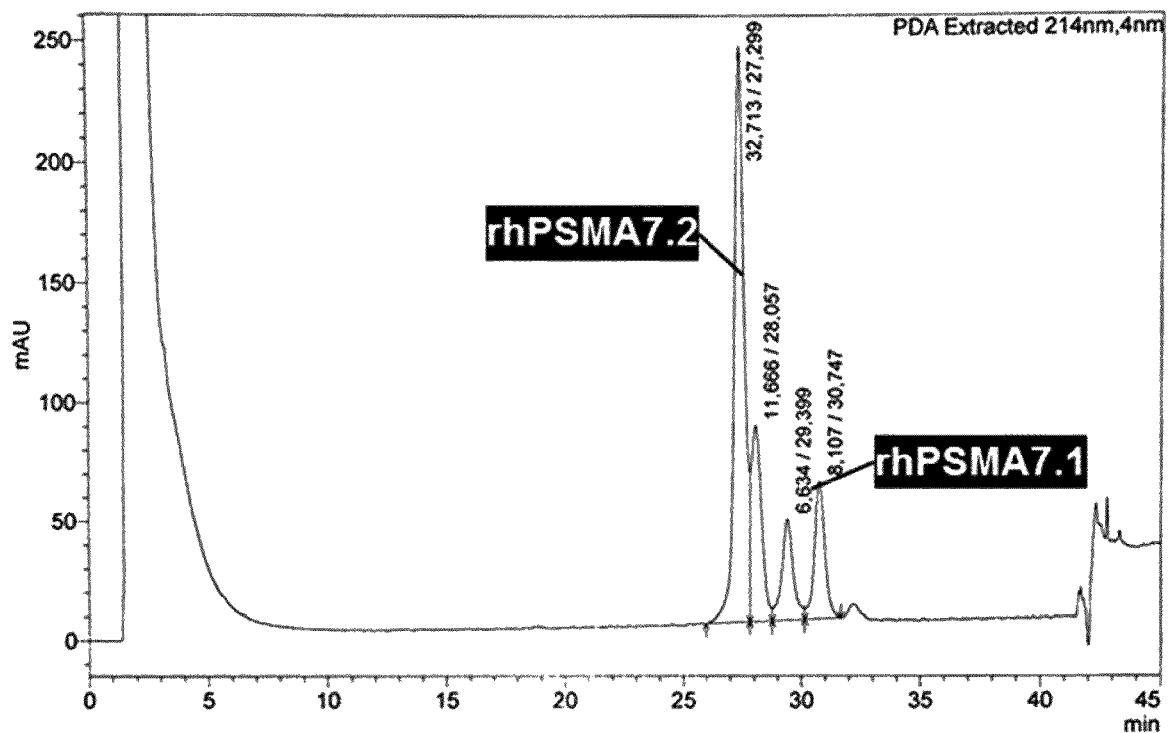
Figure 3B:
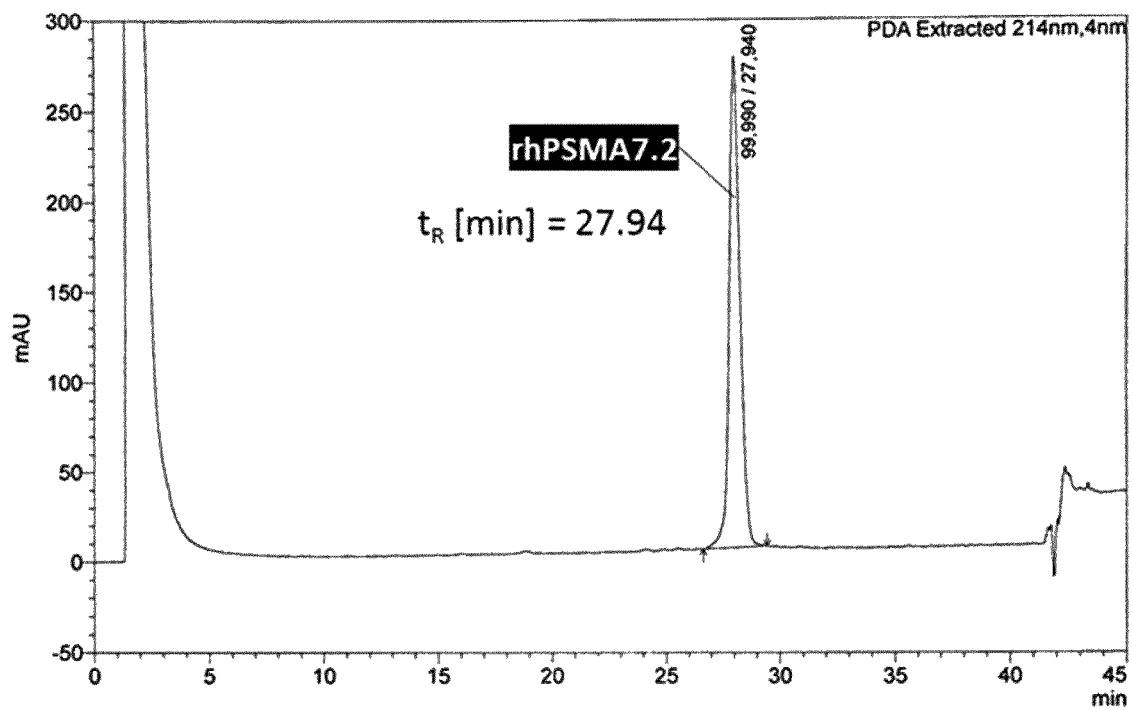
Figure 4A:
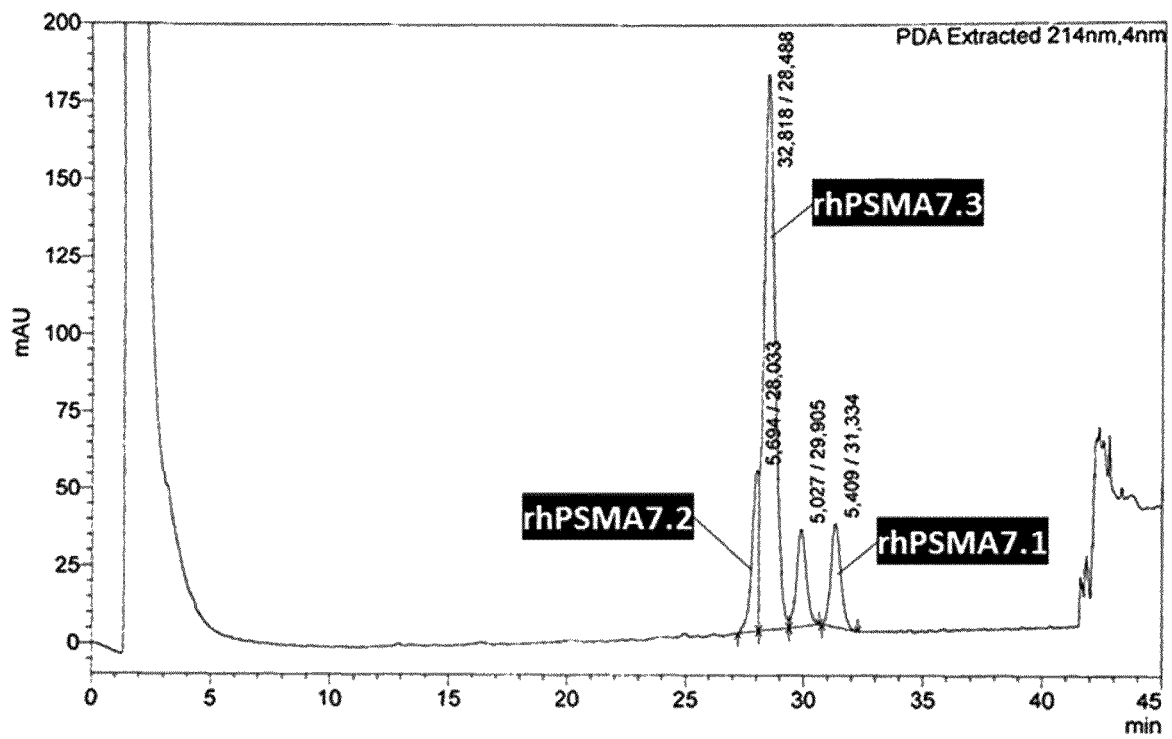
Figure 4B:
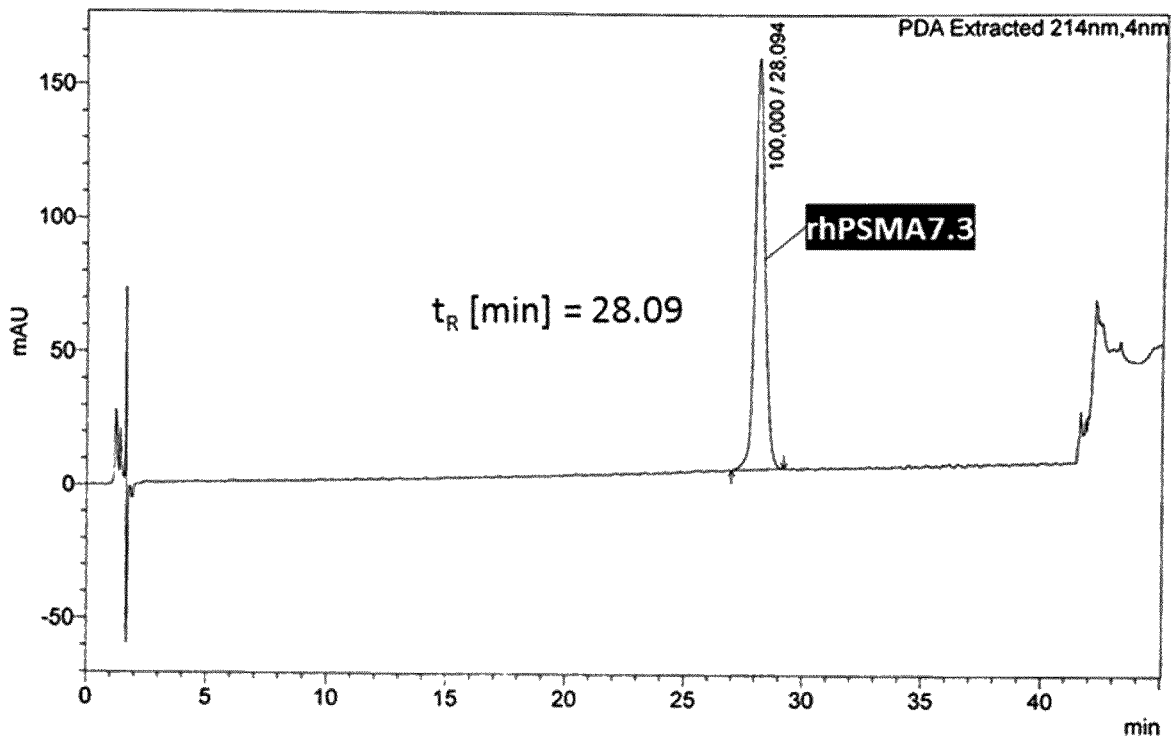
Figure 5A:
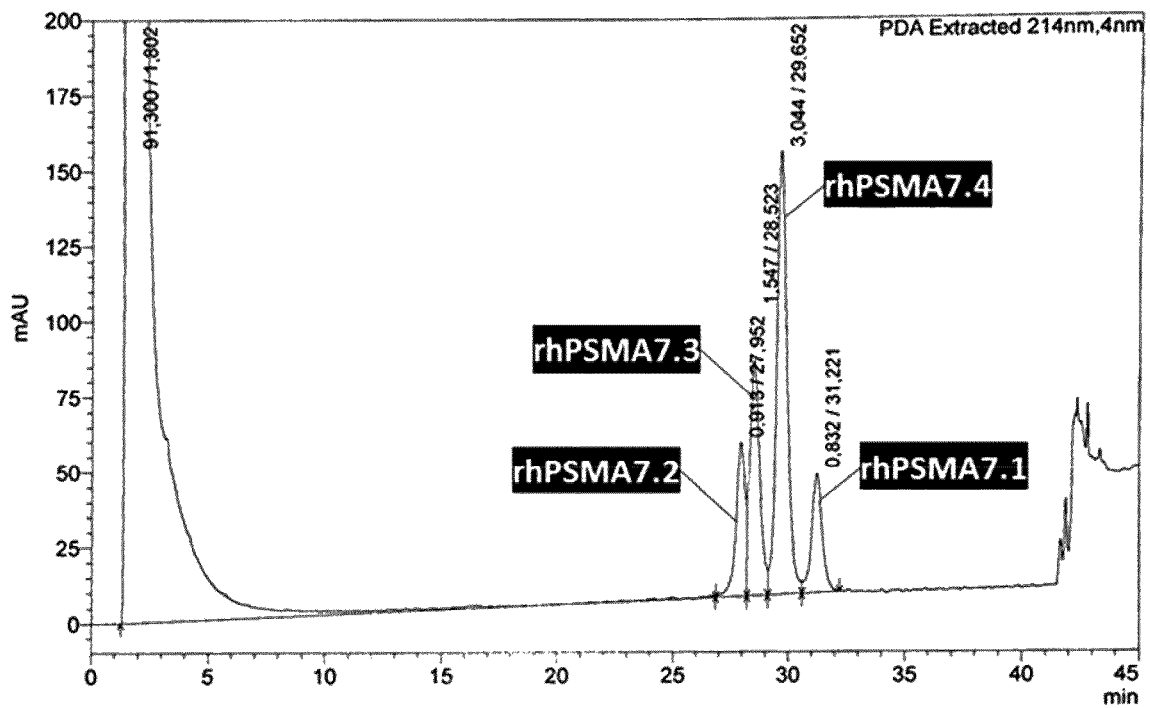
Figure 5B:
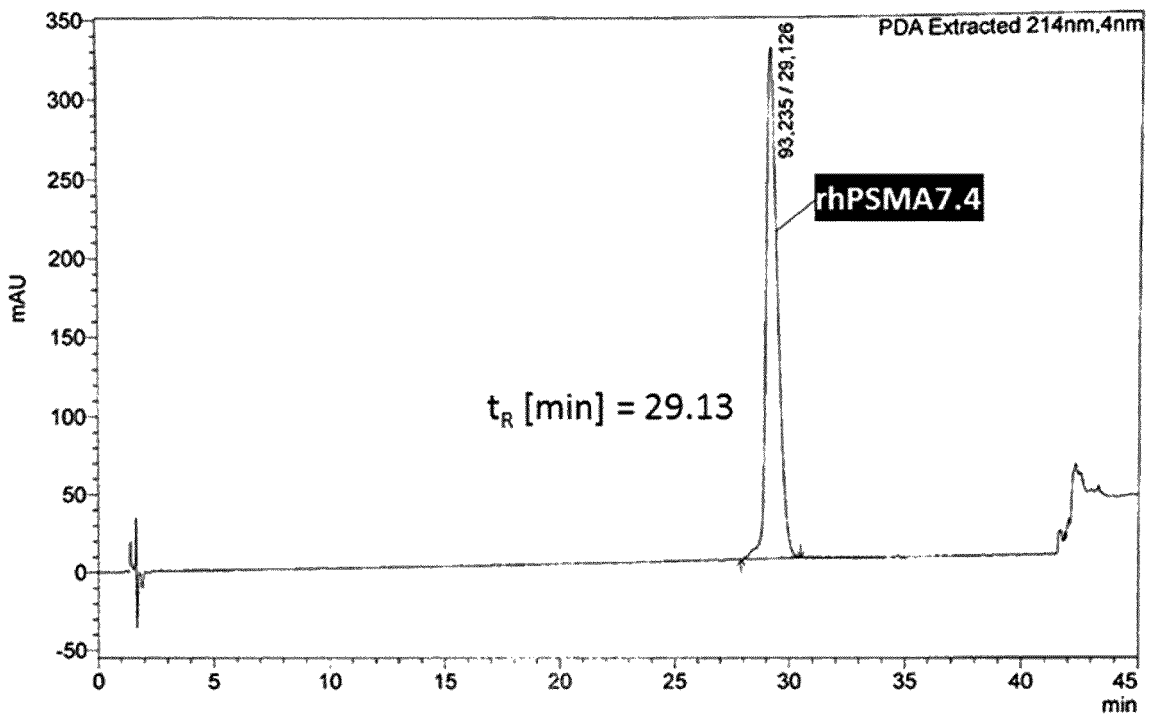

FIG. 2a: Quality Control of [19F][natGa]-rhPSMA7-rac ([19F][natGa]D/L-Dap-R/S-DOTAGA-rhPSMA-7-rac), (batch 10, precursor for the production of ([18F][natGa]D/L-Dap-R/S-DOTAGA-rhPSMA-7 at the Department of Nuclear Medicine, TUM). HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 2b: Peak assignment: D-Dap-R-DOTAGA-rhPSMA-7.1 rhPSM7-rac from FIG. 2a coinjected with enantiopure D-Dap-R-DOTAGA-rhPSMA-7.1. HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 2c: HPLC profile of D-Dap-R-DOTAGA-rhPSMA-7.1. HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 3a: Peak assignment: L-Dap-R-DOTAGA-rhPSMA-7.2 rhPSM7-rac from FIG. 2a coinjected with enantiopure L-Dap-R-DOTAGA-rhPSMA-7.2. HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 3b: HPLC profile of L-Dap-R-DOTAGA-rhPSMA-7.2 HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 4a: Peak assignment: D-Dap-S-DOTAGA-rhPSMA-7.3 rhPSM7-rac from FIG. 2a coinjected with enantiopure D-Dap-S-DOTAGA-rhPSMA-7.3. HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 4b: HPLC profile of D-Dap-D-DOTAGA-rhPSMA-7.3 HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 5a: Peak assignment: L-Dap-S-DOTAGA-rhPSMA-7.4 rhPSM7-rac from FIG. 2a coinjected with enantiopure D-Dap-S-DOTAGA-rhPSMA-7.3. HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 5b: HPLC profile of L-Dap-D-DOTAGA-rhPSMA-7.4 HPLC-conditions: Solvent A: H20+0.1% TFA; Solvent B: MeCN+0.1% TFA. Gradient: 25-35% B 0-40 min, 95-95% B 40-45 min, 35-35% B 45-50 min; flow: 1 mL/min, column: Nucleosil 100-5 C18, 125×4.6 mm, Sample: 1 mM (DMSO), 10 µL FIG. 6a: Binding affinities (IC50 [nM]) of rhPSMA7.1 and 7.2 to PSMA. Affinities were determined using LNCaP cells (150000 cells/well) and ((4-[125I]iodobenzoyl)KuE ([125I]IB-KuE; c=0.2 nM) as the radioligand (1 h, 4° C., HBSS+1% BSA). Data are expressed as mean±SD (n=3, in 3 different experiments).

Figure 6A:
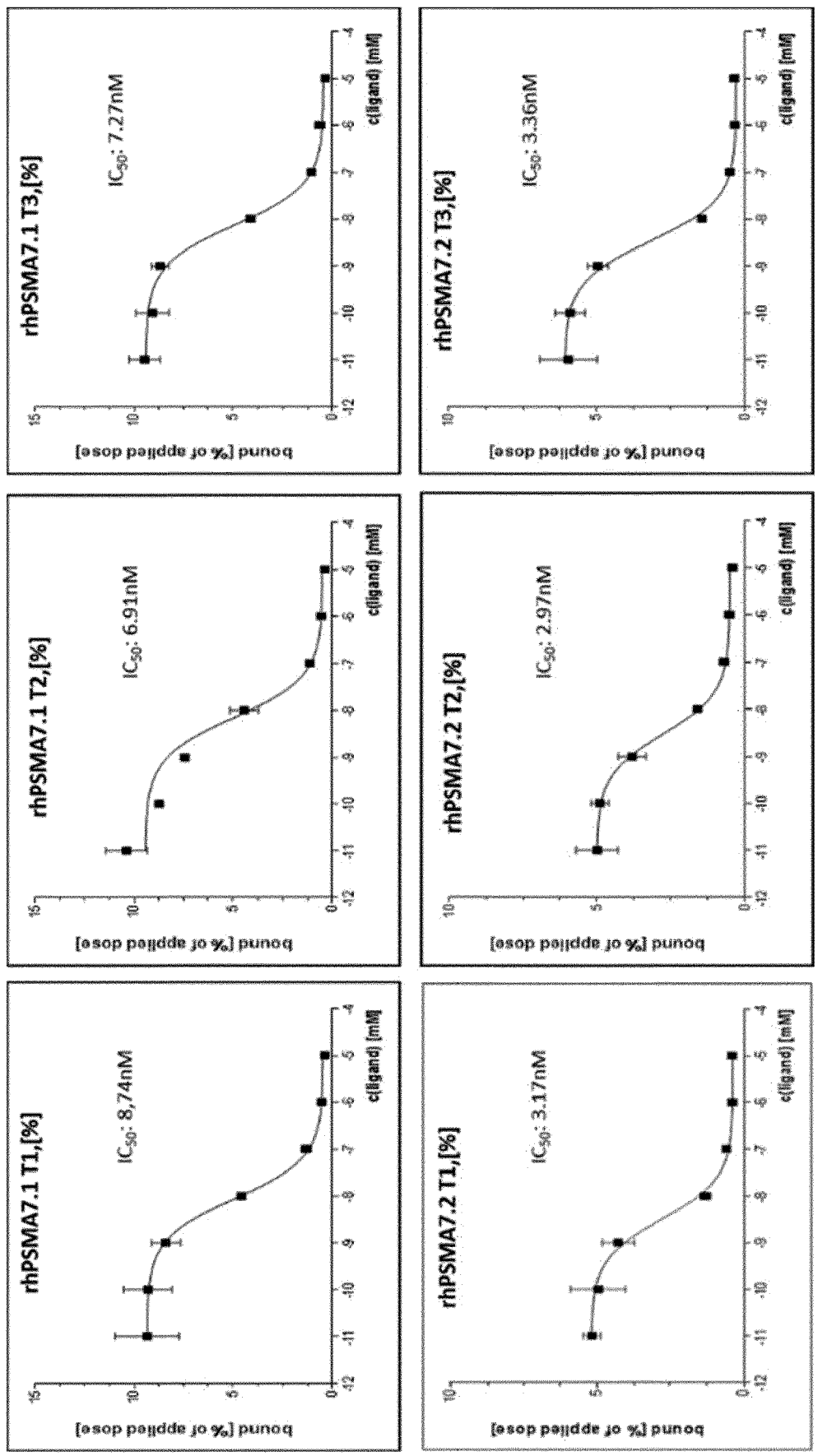
Figure 6B:
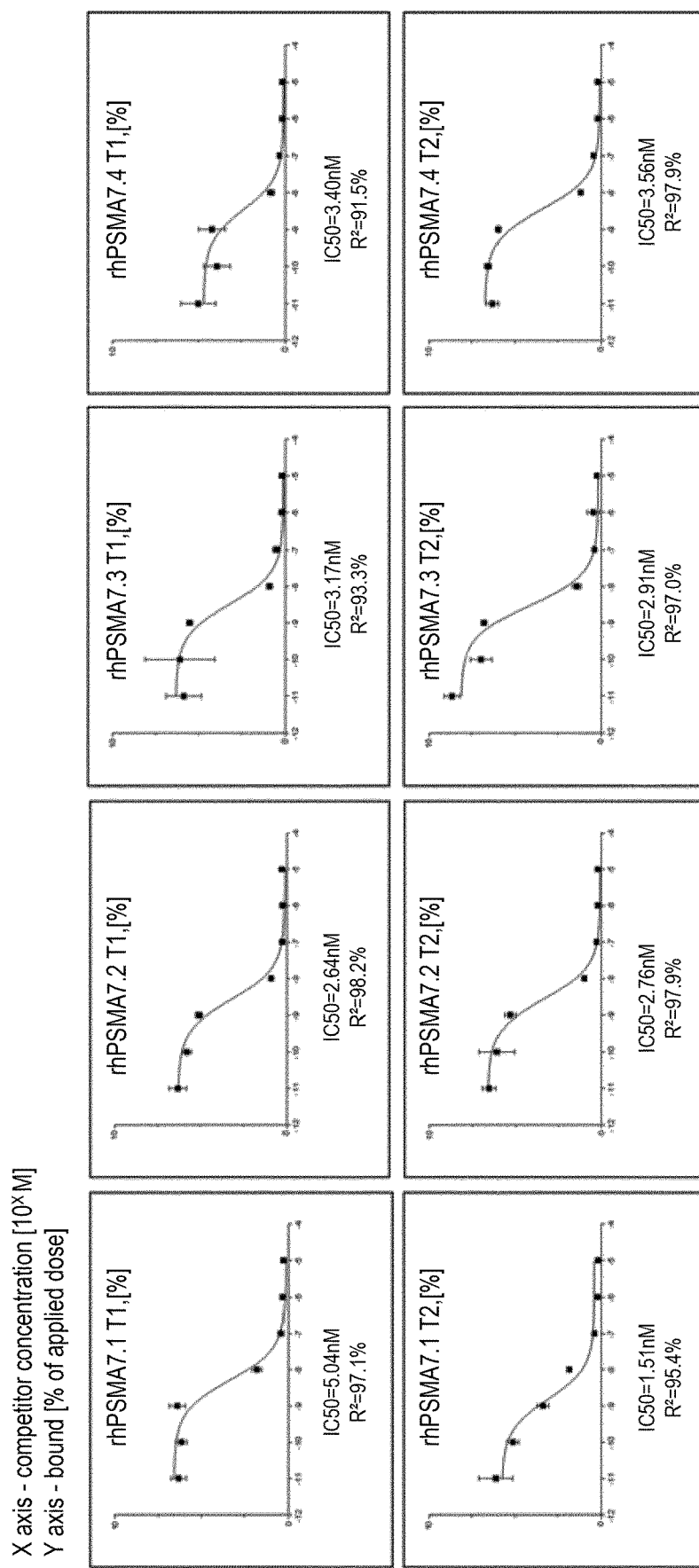
Figure 6B:
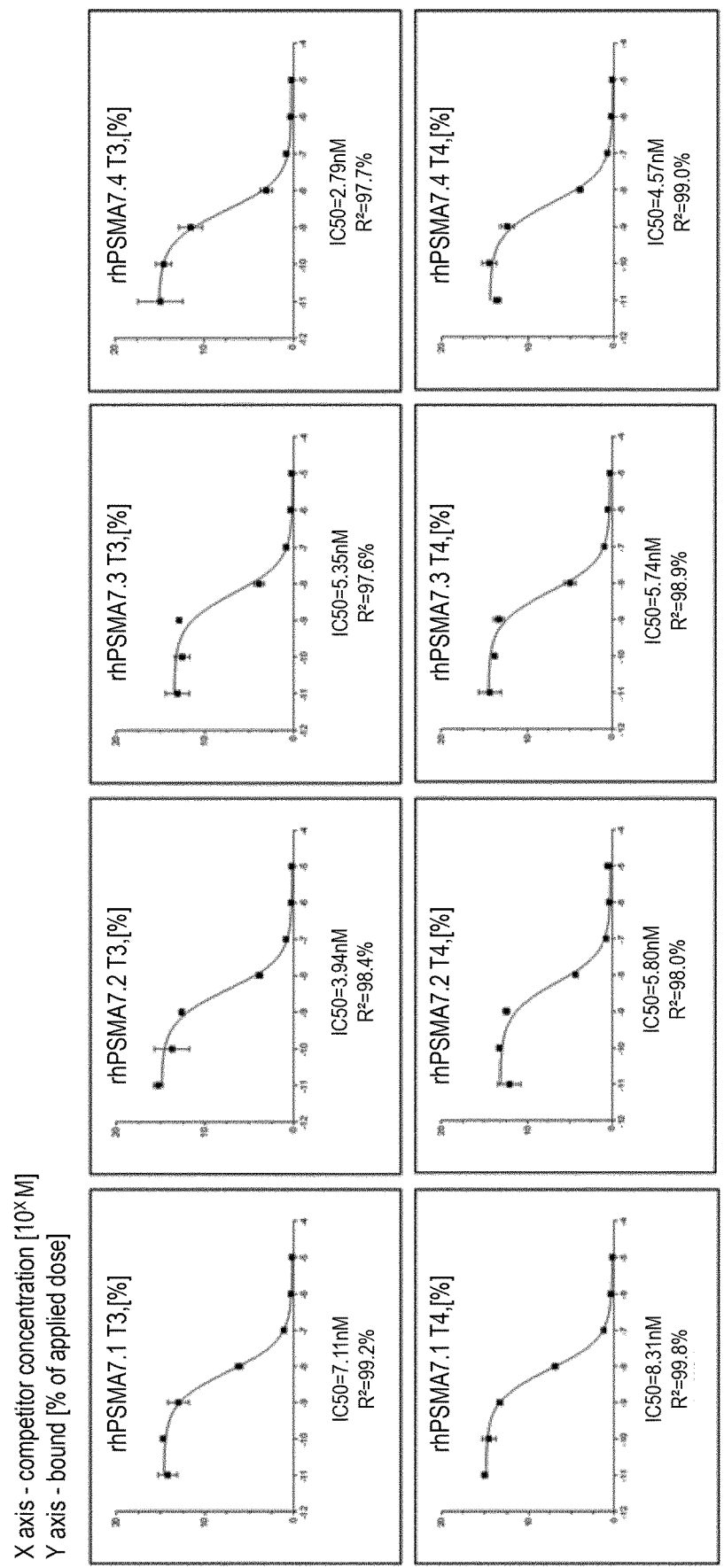
Figure 6B:
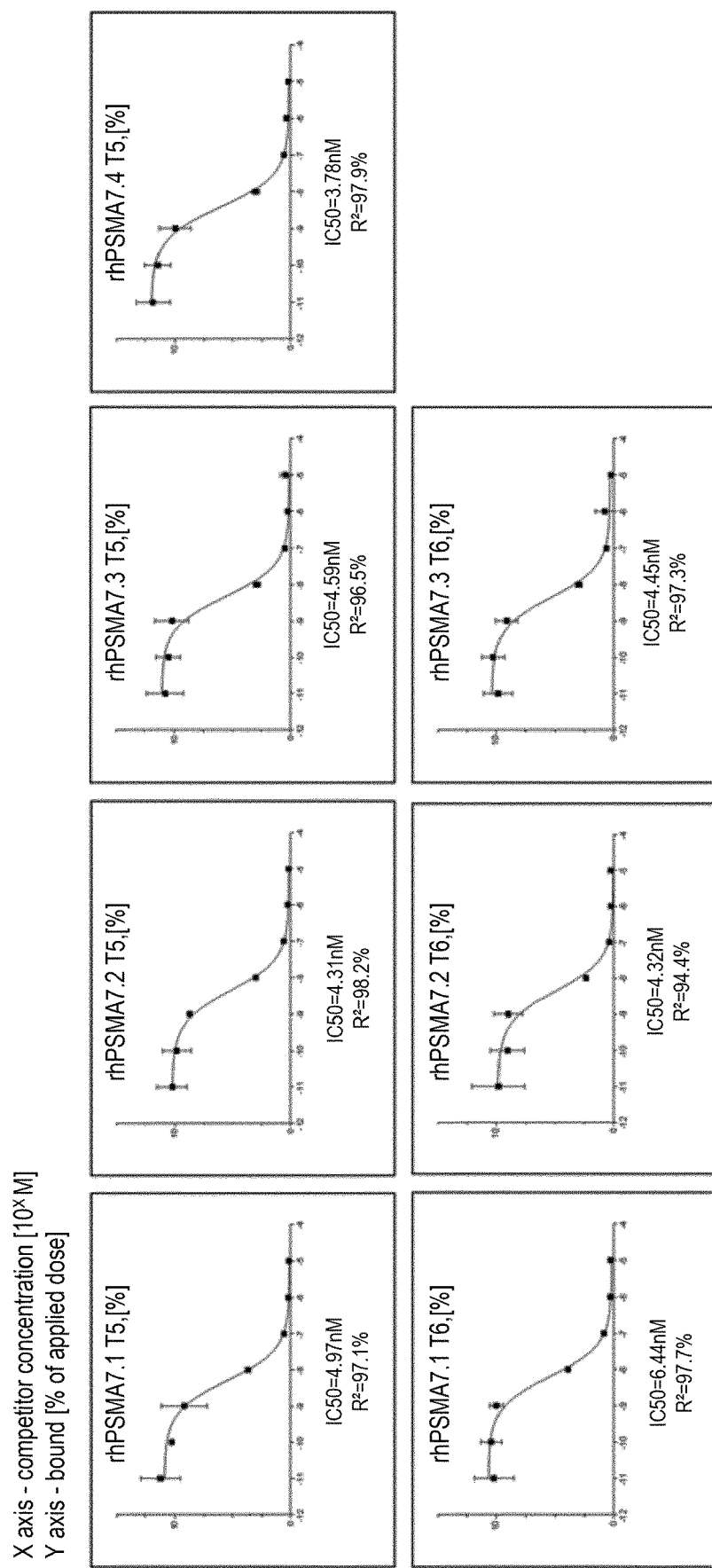

FIG. 6b: Determination of the binding affinities [nM] of the rhPSMA7 isomers to PSMA. Each of the four column shows the individual affinity measurements for rhPSAM7.1 (left) to rhPSMA7.4 (right). Conditions as described in the legend to FIG. 6a.

Figure 7:
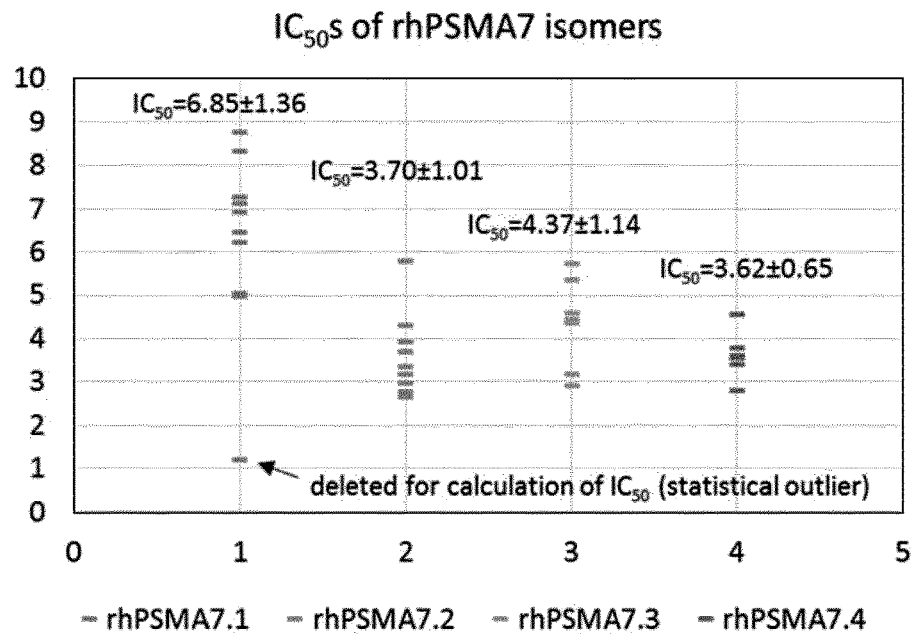
Figure 8:
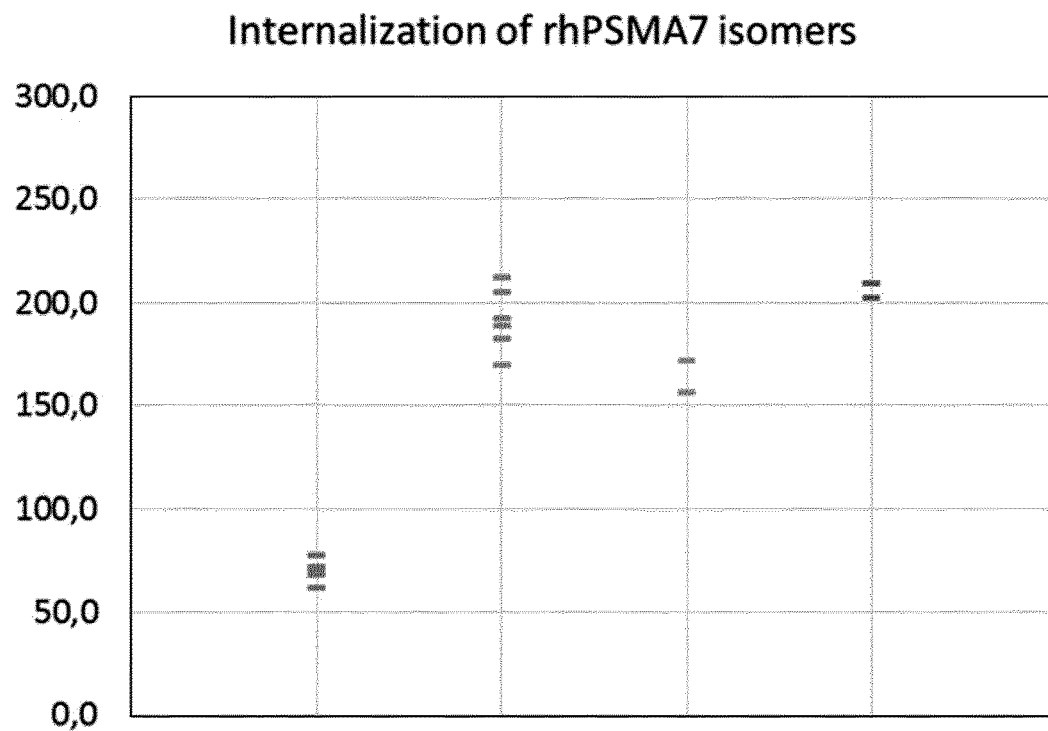

FIG. 7: Depiction of the individual IC50 [nM] measurements shown in FIGS. 6a and 6b. Value No 5 of rhPSMA7.1 was deleted Conditions as described in the legend to FIG. 6a FIG. 8: Depiction of the individual internalization measurements [% of [$^{125}$I]IB-KuE]. Internalized activity (c=0.5 nM) at 1 hour as % of the reference ligand ([$^{125}$I]I-BA)KuE (c=0.2 nM), determined on LNCaP cells (37° C., DMEM F12+5% BSA, 125000 cells/well). Data is corrected for non-specific binding (10 µmol PMPA) and expressed as mean±SD (n=3).

Figure 9:
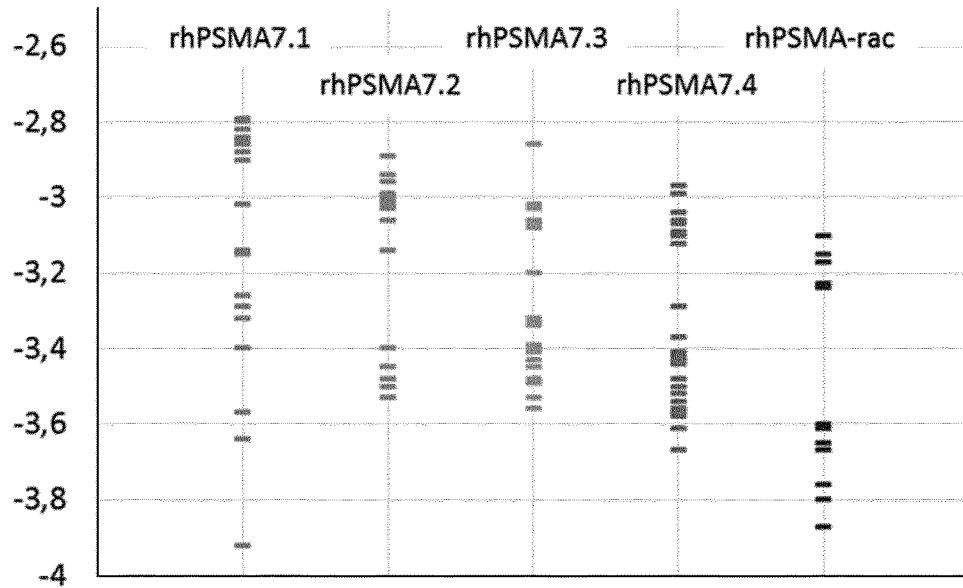

FIG. 9: Depiction of the individual measurements of the logP's of the rhPSMA isomers.

Figure 10:
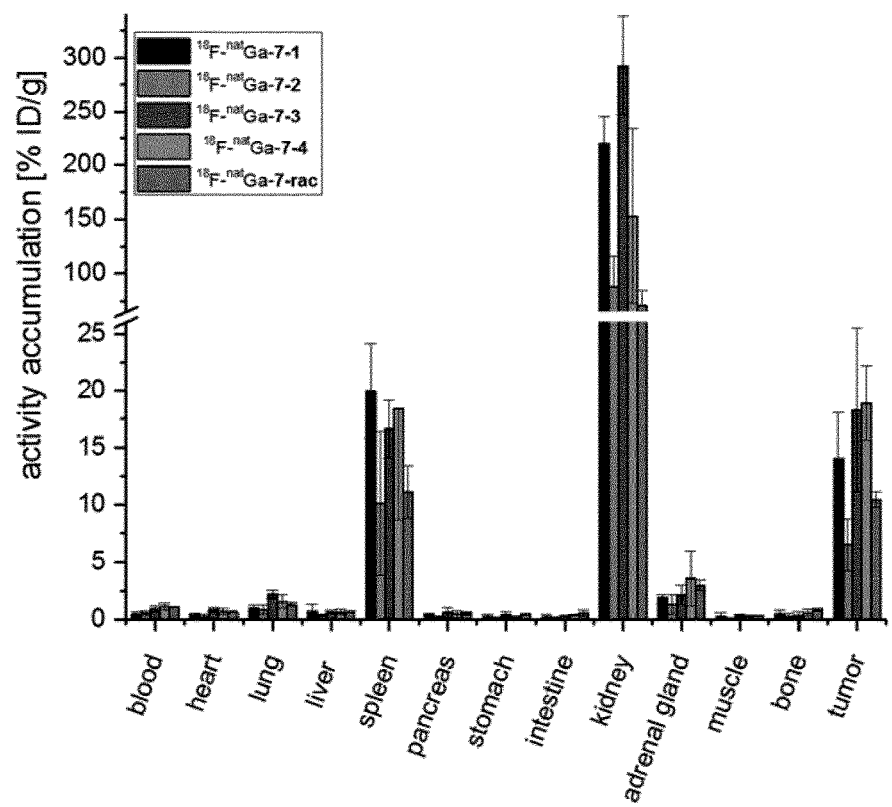

FIG. 10: Biodistribution (in % ID/g) of $^{18}$F-labeled rhPSMA tracers at 1 h p.i in LNCaP tumor-bearing SCID mice. Data are expressed as mean±SD (n=4 for rhPSMA7.1, n=5 for 7.2, n=4 for 7.3, n=5 for 7.4 and n=3 for 7-rac).

Figure 11:
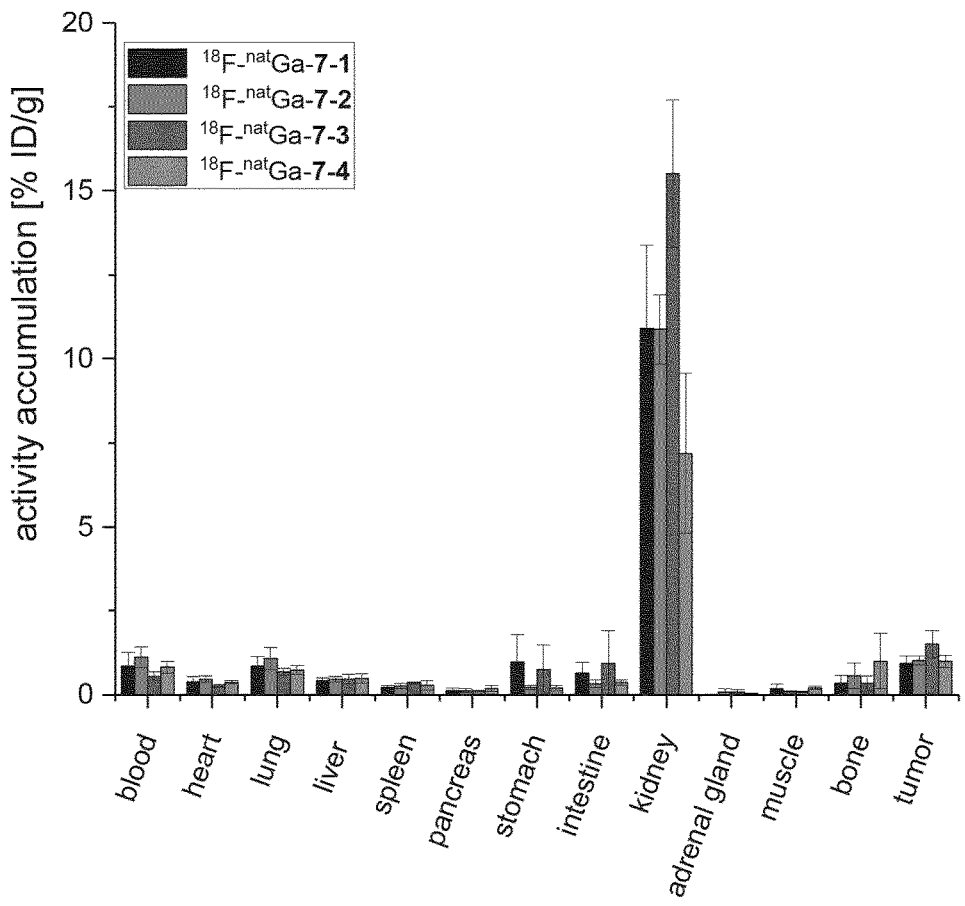

FIG. 11: Biodistribution [% ID/g] of $^{18}$F-rhPSMAs co-injected with PMPA (8 mg/kg) at 1 h p.i in LNCaP tumor-bearing SCID mice. Data are expressed as mean±SD (n=3).

Figure 12:
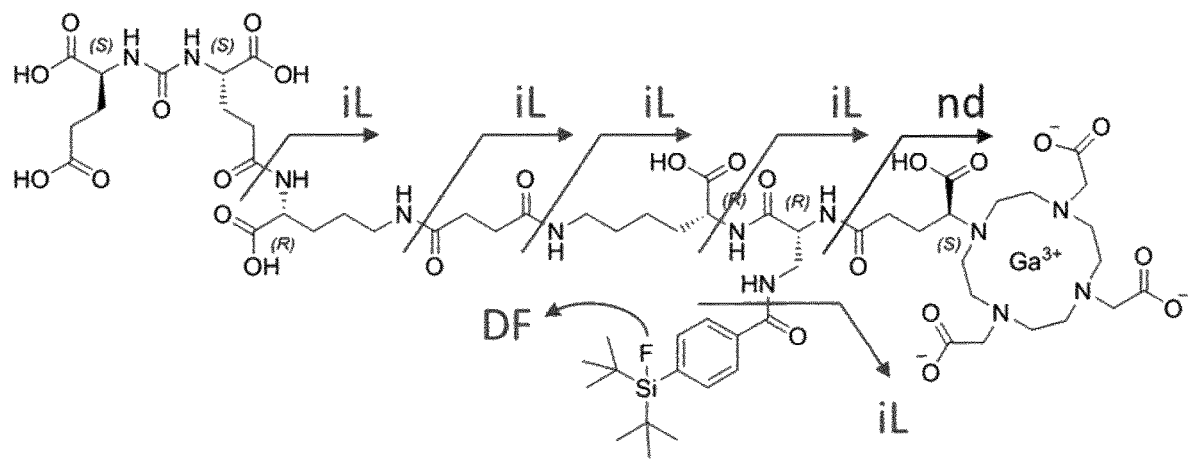

FIG. 12: Possible species generated by metabolic cleavage of amide bonds. iL: cleavage forms a species with increased lipophilicity; DF: defluorination; nd: not detectable, since not radioactive.

Figure 13:
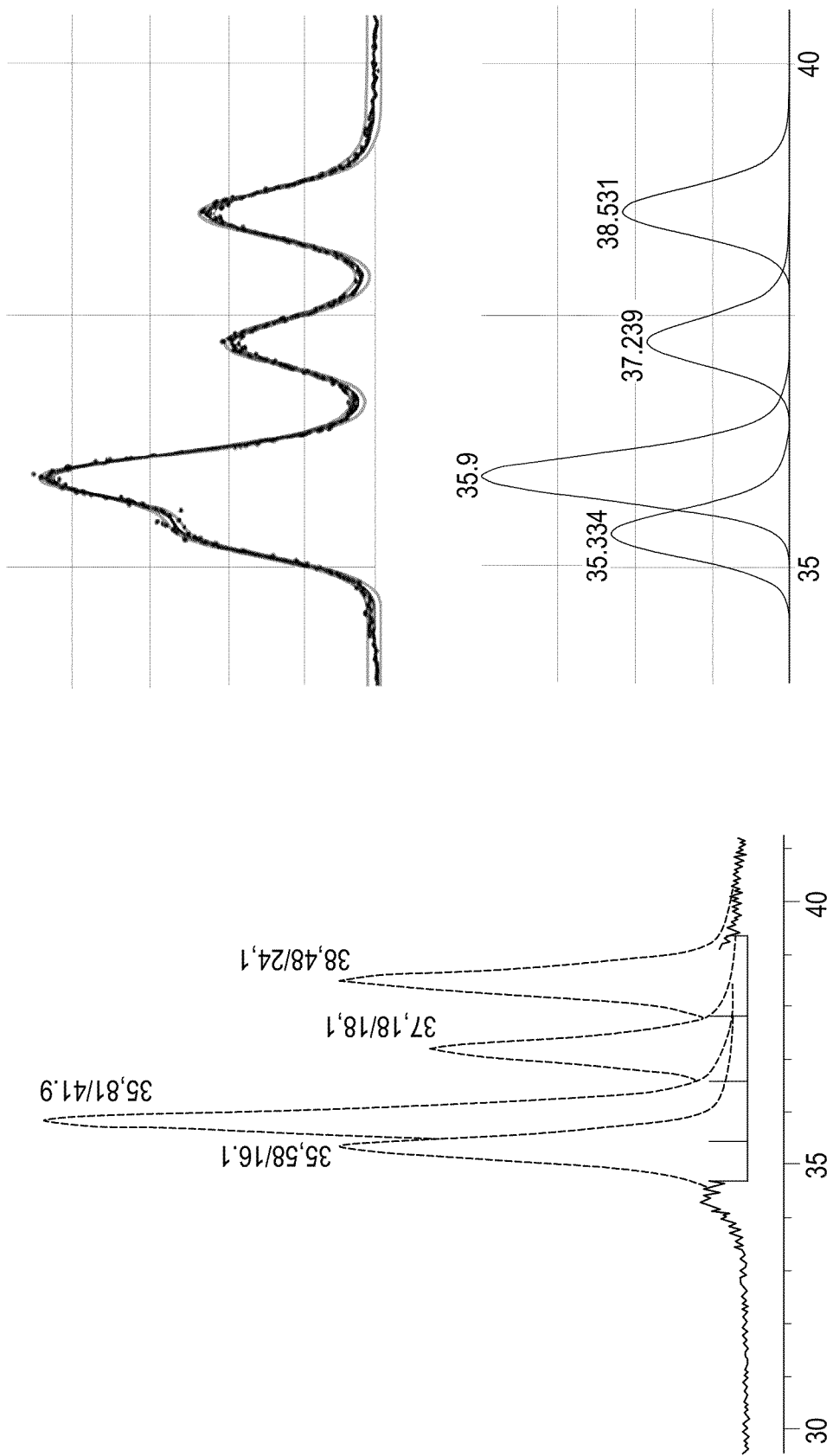

FIG. 13: Left: Graphical analysis of overlapping peaks 1 (rhPSMA7.2) and 2 (rhPSMA7.3); right: deconvolution and integration of peak profiles by Systat PeakFit Software); top: experimental data fitted, bottom: deconvoluted single peaks.

Figure 14A:
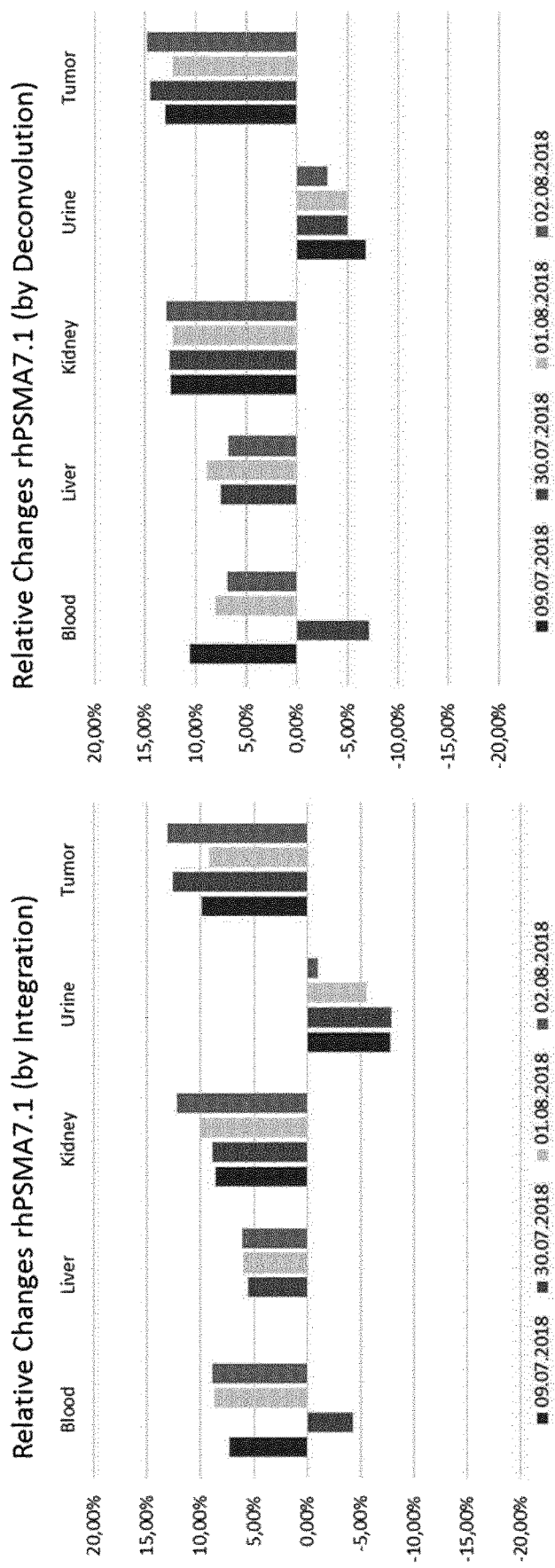

FIG. 14a: Quantification of relative changes (in % change of injected racemic mixture) to evaluate the reproducibility of classical integration (by HPLC program) and deconvolution (by 'PeakFit') of peak 4 (rhPSMA7.1). Both methods demonstrate similar performance for this peak.

Figure 14B:
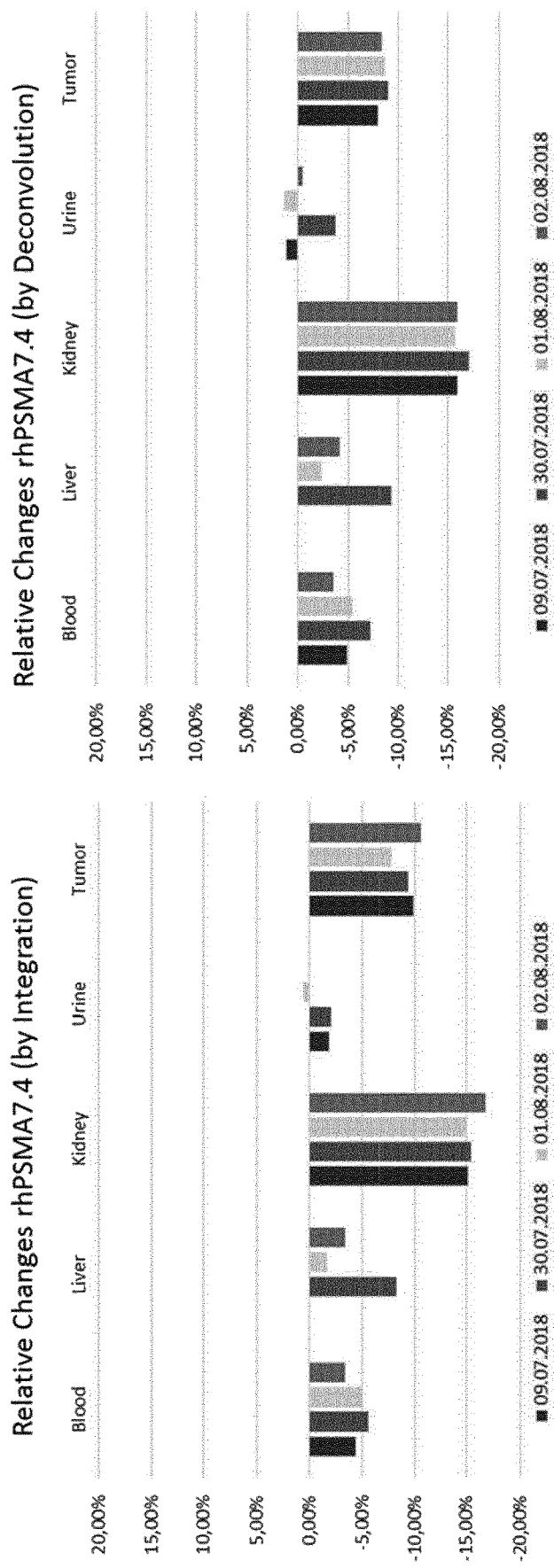

FIG. 14b: Quantification of relative changes (in % change of injected racemic mixture) to evaluate the reproducibility of classical integration (by HPLC program) and deconvolution (by 'PeakFit') of peak 3 (rhPSMA7.4). Both methods demonstrate similar performance for this peak.

Figure 15:
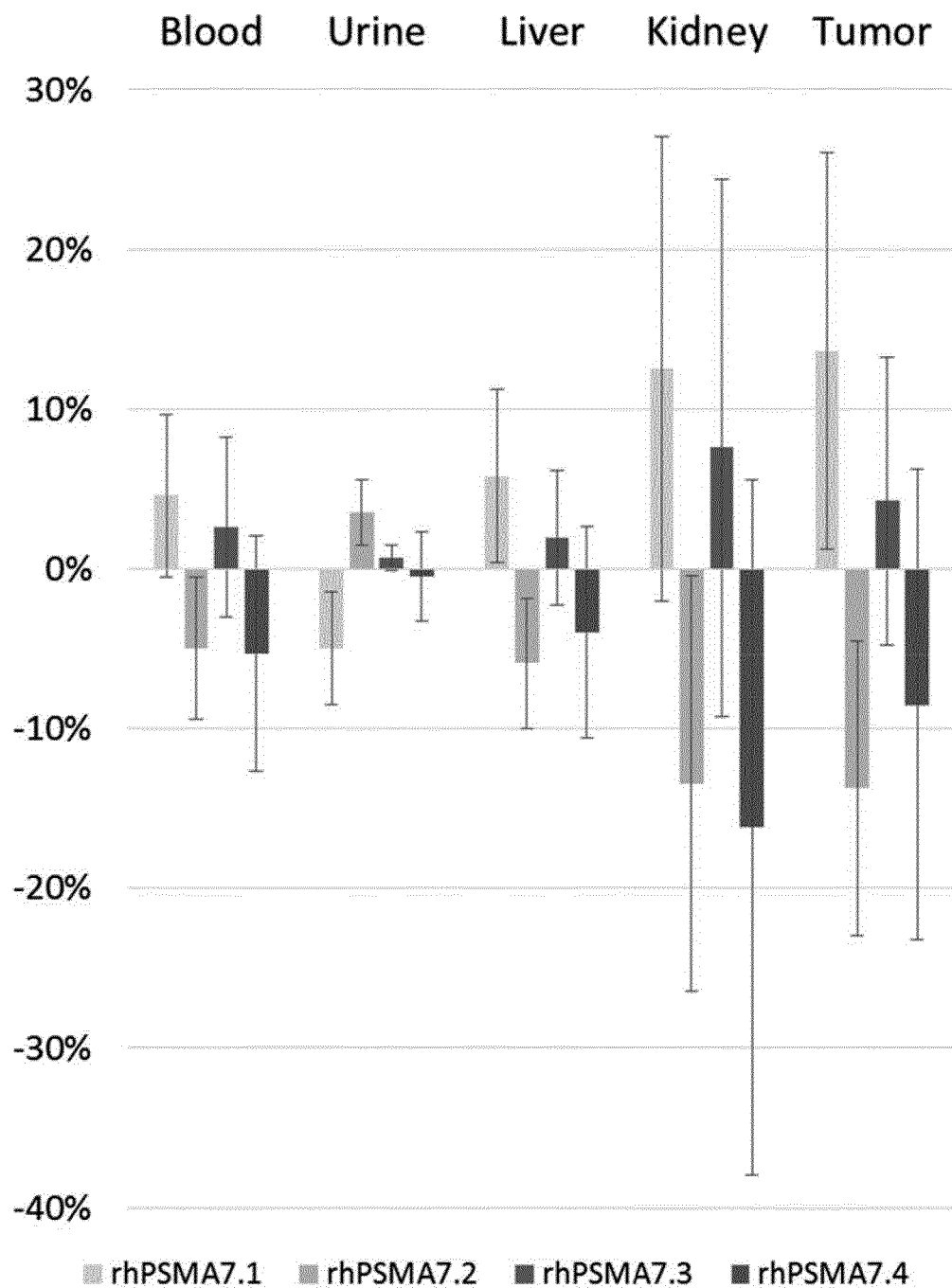

FIG. 15: Percentage change of each rhPSAM7.1-7.4 isomer in blood, liver, kidney, tumor and urine with respect to its proportion the injected solution ([$^{18}$F][$^{nat}$Ga] rhPSMA7-rac. Data expressed as mean values±SD (n=4; see also FIG. 16).

Figure 16:
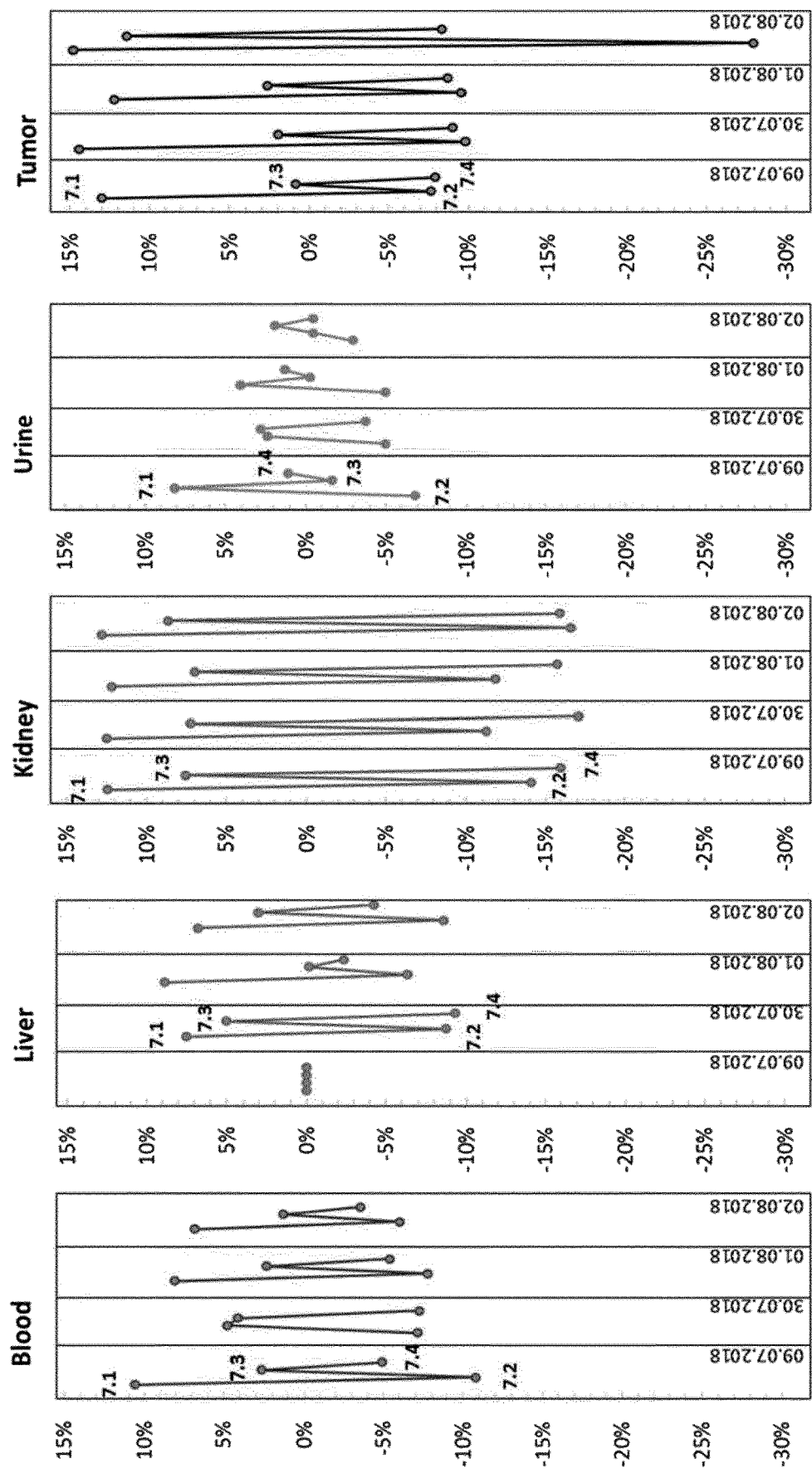

FIG. 16: Percentage change of each rhPSAM7.1-7.4 isomer for each sample and experiment) in blood, liver, kidney, tumor and urine with respect to its proportion in the injected solution ([$^{18}$F][$^{nat}$Ga]rhPSMA7-rac). Analyses were carried out with Systat PeakFit.

Figure 17:
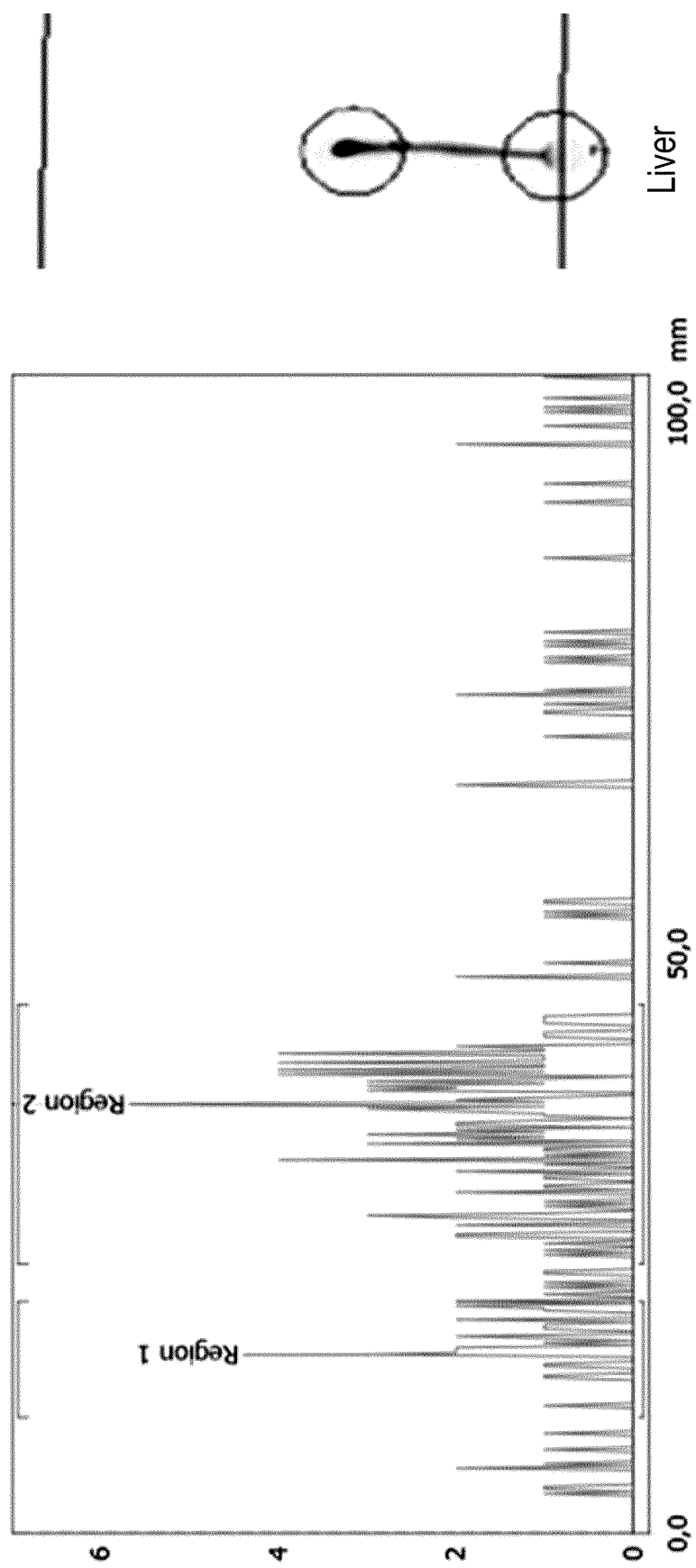

FIG. 17: Left: TLC scanner profile of a TLC plate with liver sample (30.07.2018, overall cts: 142 cts). Due to their bad statistics and limited validity dataset with cts<200 were removed. Right: Phophoimage of a TLC plate with liver sample: long tailing of the moving tracer.

Figure 18:
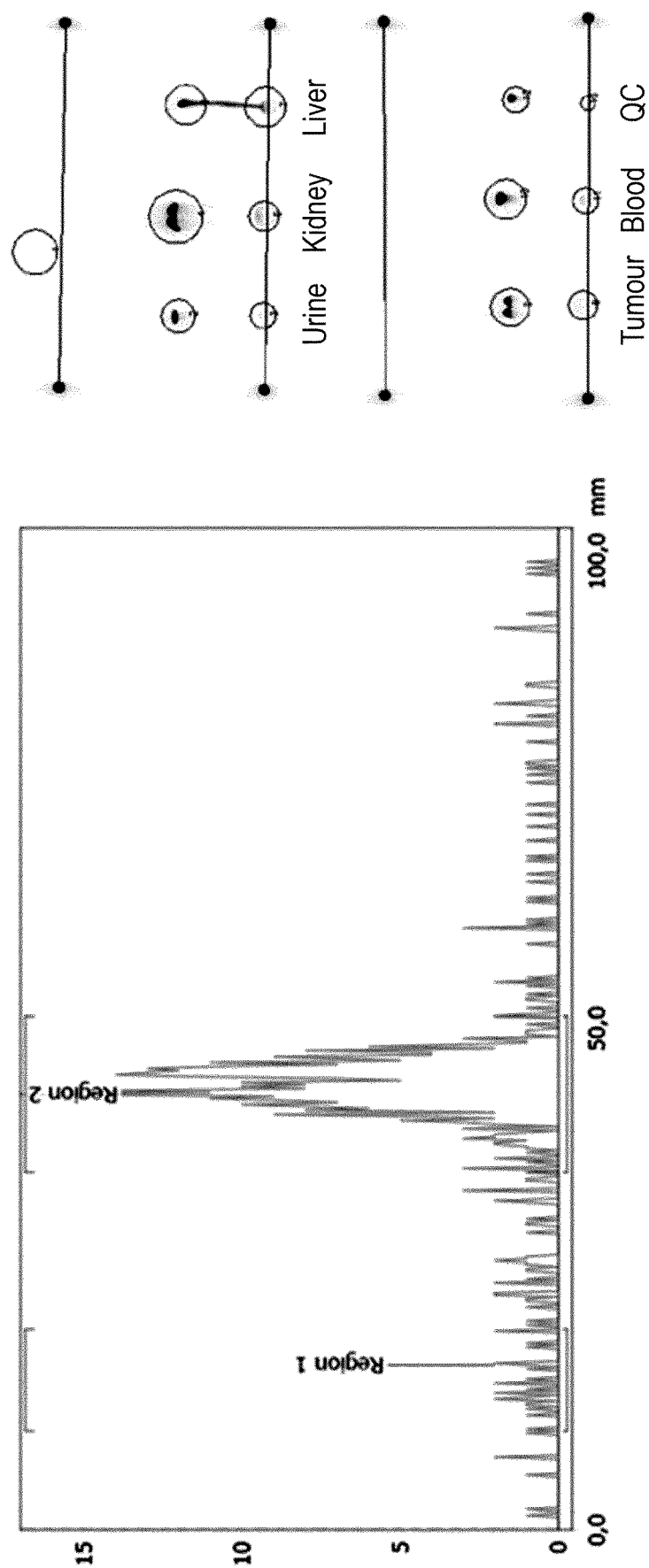

FIG. 18: Left: TLC scanner profile of a TLC plate with a quality control sample (01.08.2018, overall cts: 384). Right: Exemplay phophoimage of a TLC plate with Urine, kidney, liver, tumor, blood and QK sample.

Figure 19:
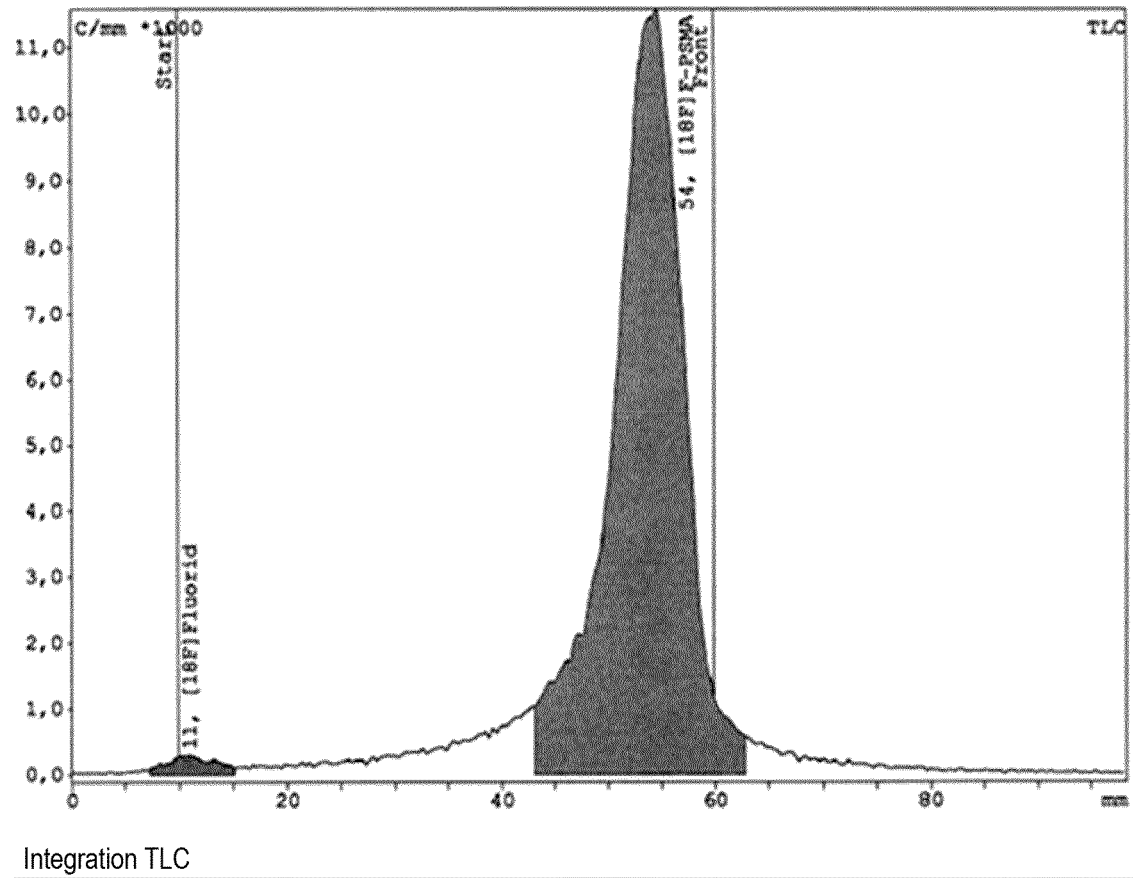

FIG. 19: Radio-TLC of [F-18]rhPSMA7-rac (30.07.2018) as part of the Quality Control in the Department of Nuclear Medicine prior to clinical application of the tracer. Note that a tailing of the tracer is even observed in the formulation buffer (and thus in the absence of proteins).

Figure 20:
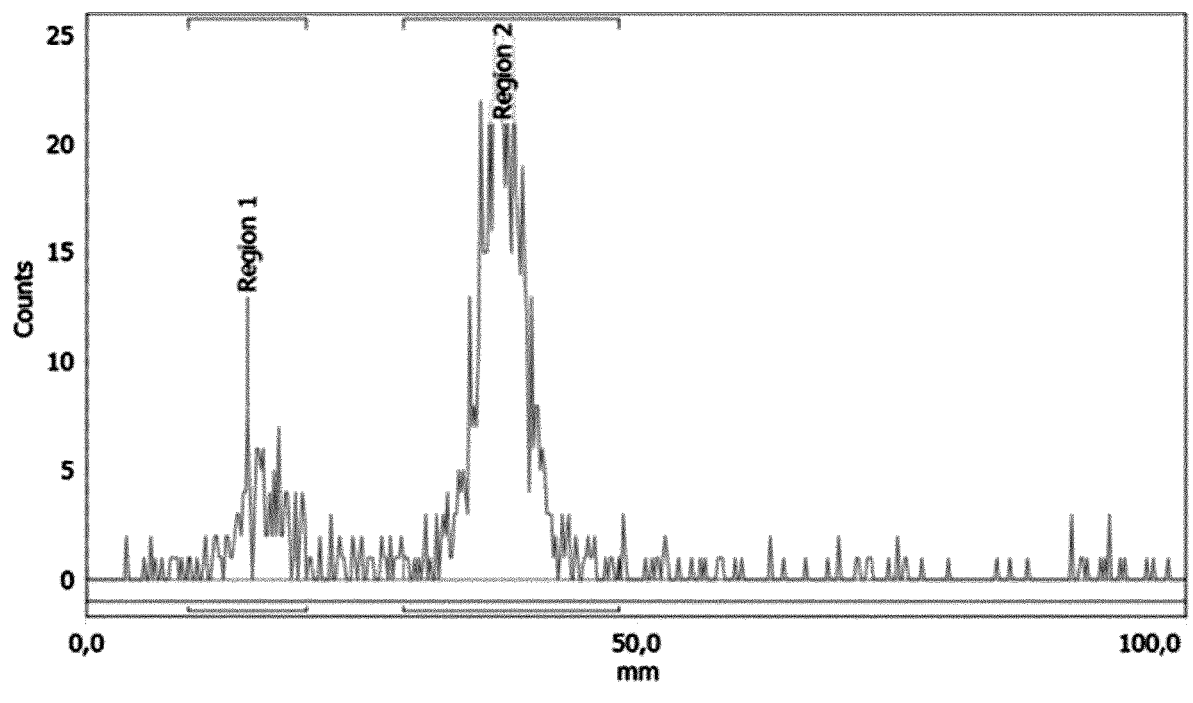

FIG. 20: Quantification of free [F-18]Fluoride and 'intact' [F-18]rhPSMA7-rac by radio-TLC of a urine sample (30.07.2018).

Figure 21:
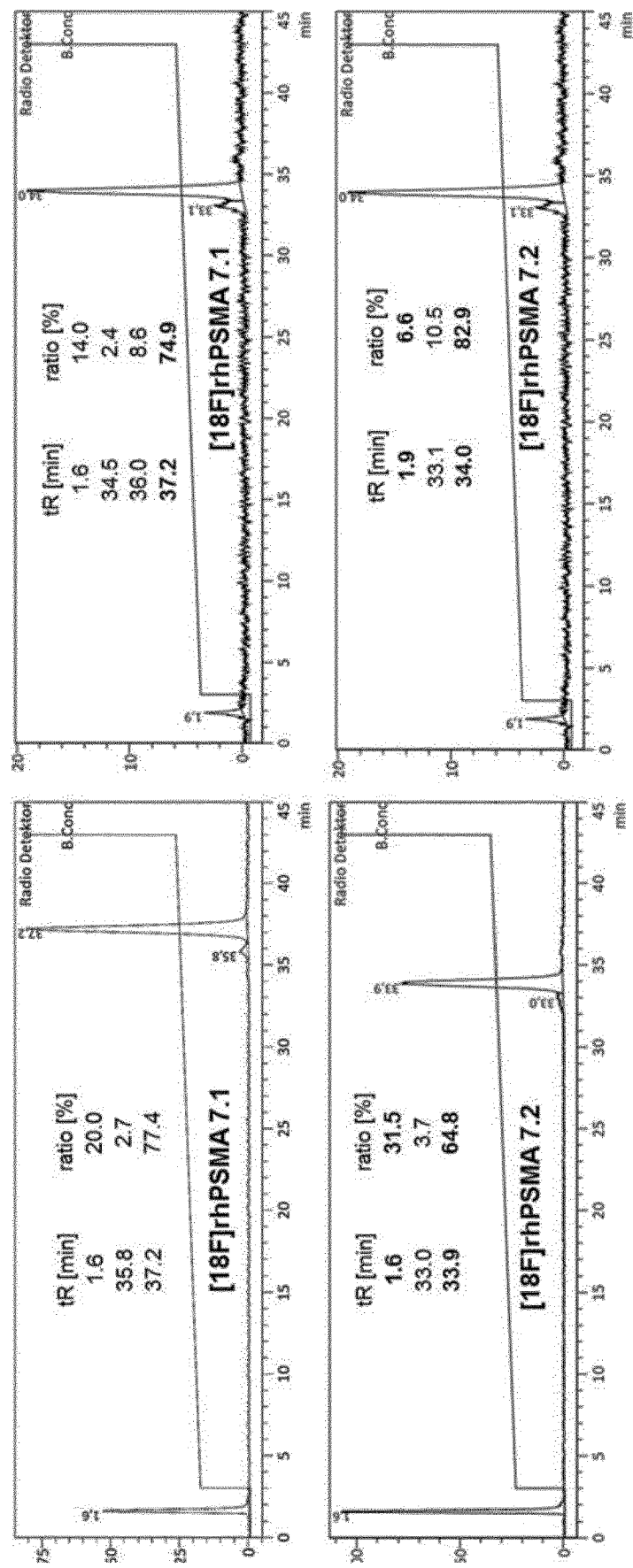
Figure 21:
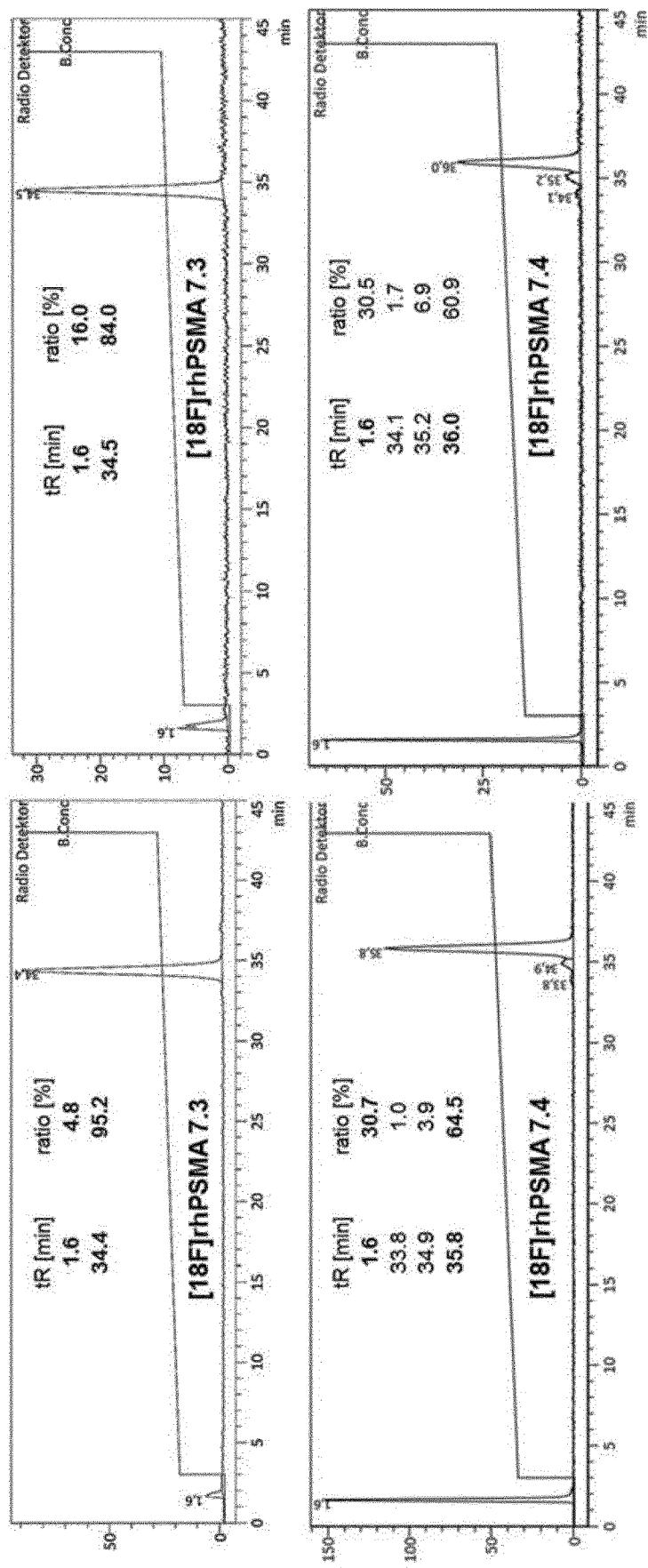

FIG. 21: Left: Radio-HPLC analysis of urine collected and pooled from 4 normal mice injected with the respective [F-18]rhPSAM-7.x tracer. Right: Radio-HPLC analysis of 'cold' urine spiked with the respective [F-18]rhPSAM-7.x tracer for a period of 1 h (7.1., 7.2.), 0.5 h (7.3.) and 2 h (7.4.). HPLC-conditions: Solvent A: H20+0.1% TFA; Solvent B: MeCN+0.1% TFA; Gradient: 5% isocratic 0-3 min, 25-35% B 3-43 min, 95-95% B 43-48 min; flow: 1 mL/min, column: Nucleosil 100-5 C18, 125×4.6 mm FIG. 22: Separation of radioactive species in urine by cartridge fixation and TLC. Top: Radio-HPLC analysis of urine 30 min p.i. of [F-18]rhPSMA7.3 in mice showing a small proportion at 1.6 min and intact tracer at ca. 34.5 min. Bottom (left): urine of mice, 30 min p.i. of [F-18] rhPSMA7.3, was diluted and subjected to STRATA-X cartridge fixation. The cartridge was washed and eluted with MeCN/water (60/40 v/v +1% TFA); only intact tracer was detected. Bottom (right): both the breakthrough from the cartridge fixation (non-retained components) and the fraction finally eluted MeCN/water from the cartridge were analysed by TLC (bottom, right). Whereas 96.1% [F-18] rhPSMA7.3 and only 3.9% [F-18]fluoride were found in the eluate of the cartridge, the reverse ratio was found in the breakthrough of the cartridge (3.4% [F-18]rhPSMA7.3 and only 96.6% [F-18]fluoride)

Figure 23:
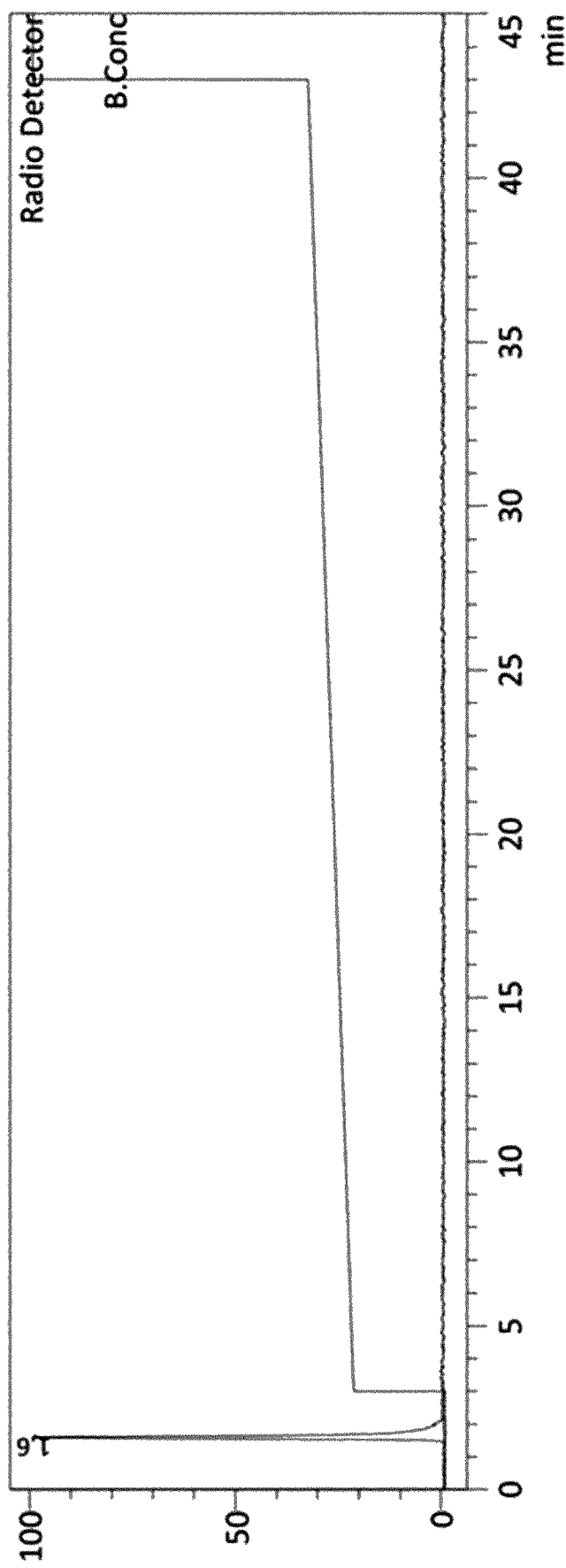

FIG. 23: To fresh and nonradioactive urine of mice [F-18]rhPSMA7.3 was added, followed by 0.5 μmol cold F-19-fluoride; incubation for 2 h. Radioactivity was completely (98.5%) converted to a very hydrophilic fraction representing [F-18]fluoride (peak at 1.6 min). Note: peak at 1.6 min was subsequently immobilized on a QMA cartridge and eluted with with NaCl (1M) (=fluoride).

Figure 24:
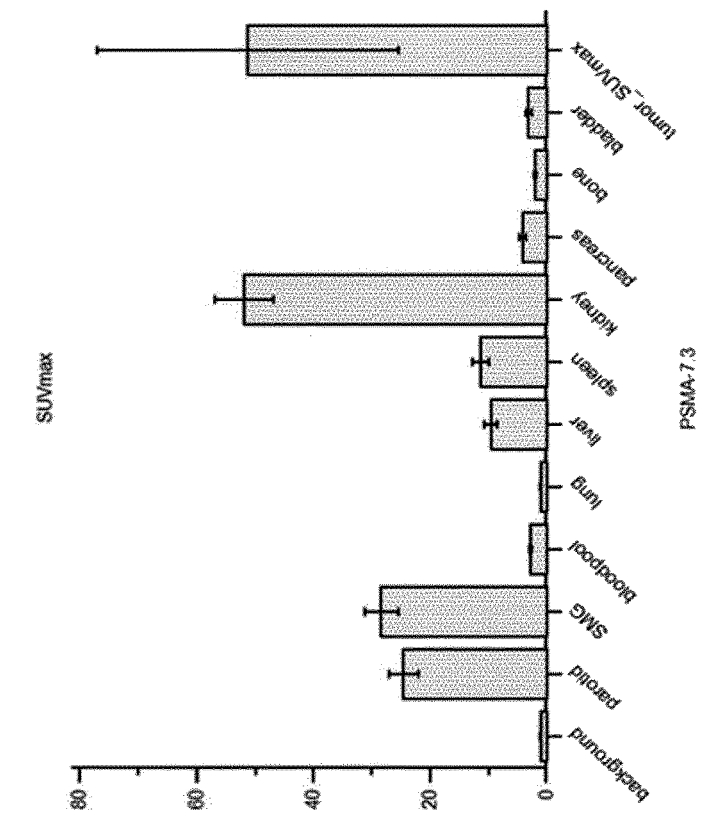
Figure 24:
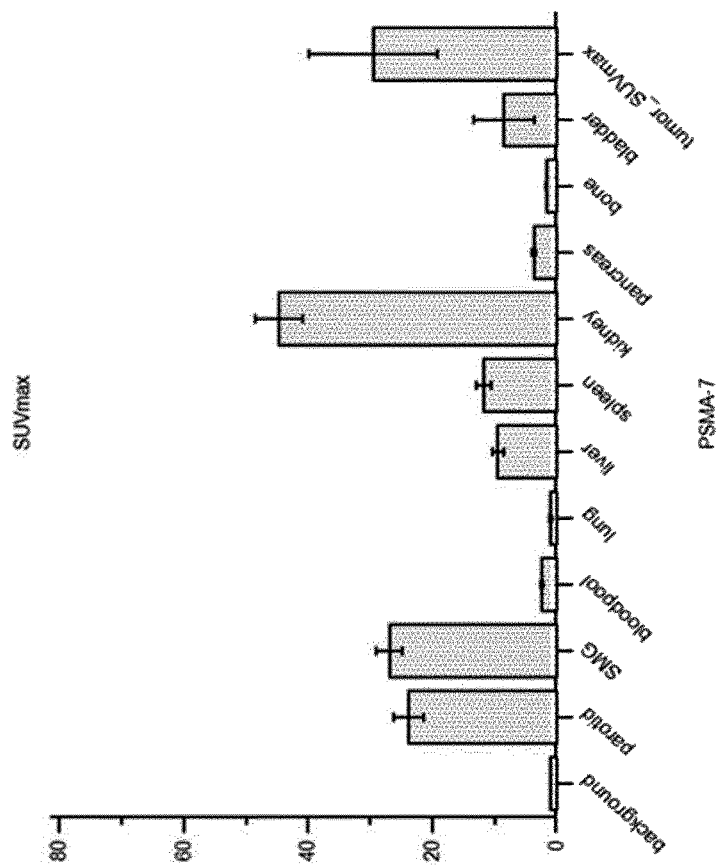

FIG. 24: Clinical biodistribution and uptake in tumor lesions of 18F-rhPSMA-7 (left) and 18F-rhPSMA-7.3 (right) as demonstrated by SUVmax. Data are expressed as mean±SD.

Figure 25:
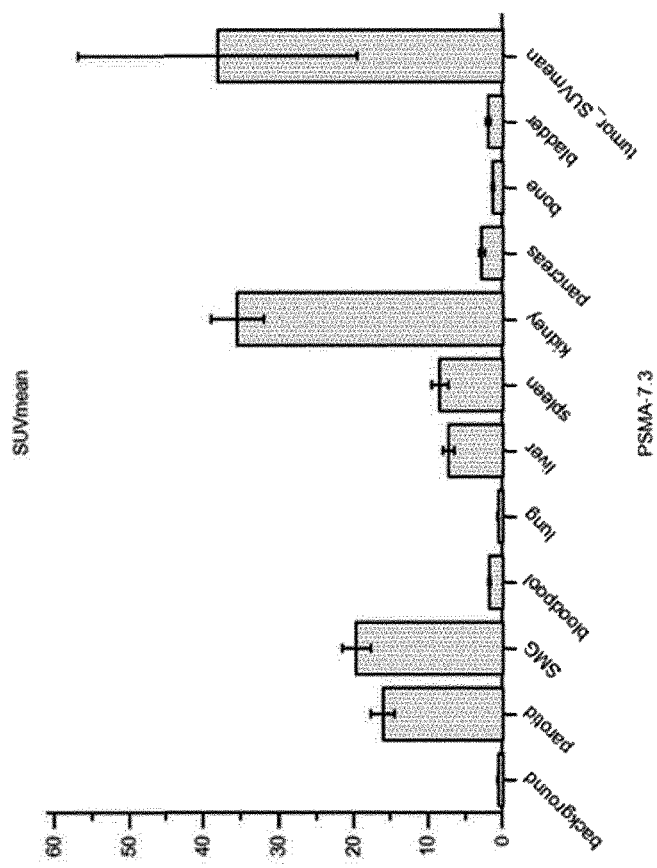
Figure 25:
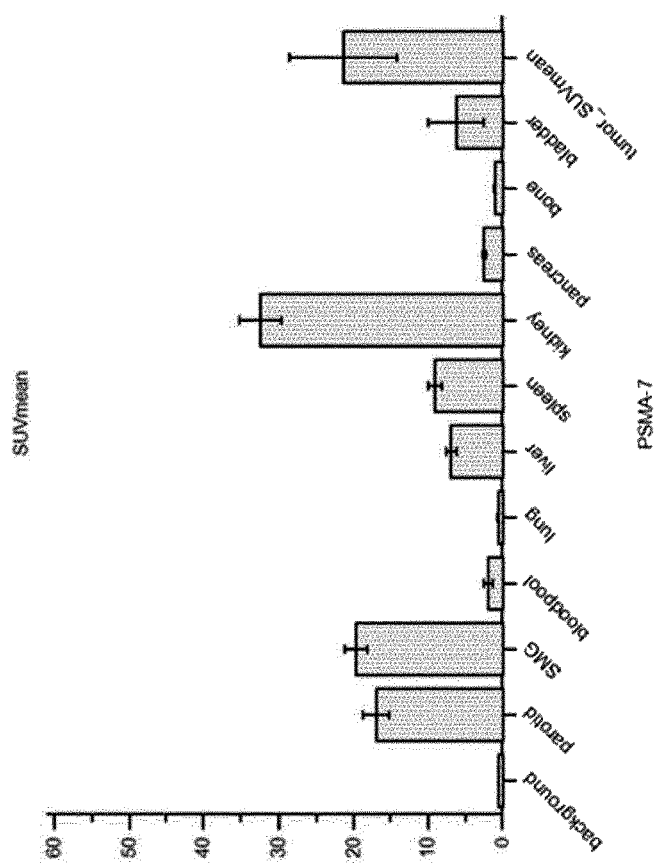

FIG. 25: Clinical biodistribution and uptake in tumor lesions of $^{18}$F-rhPSMA-7 (left) and $^{18}$F-rhPSMA-7.3 (right) as demonstrated by SUVmean. Data are expressed as mean±SD.

Figure 26:
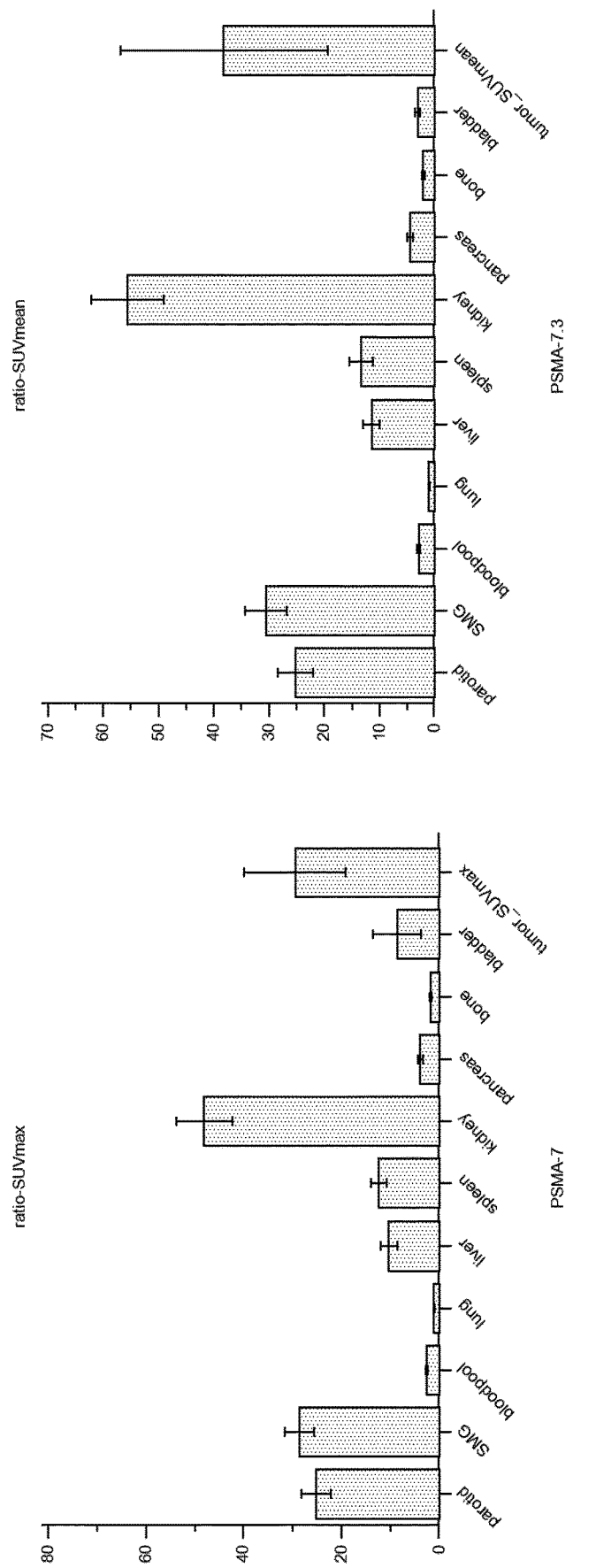

FIG. 26. Clinical biodistribution and uptake in tumor lesions of $^{18}$F-rhPSMA-7 (left) and $^{18}$F-rhPSMA-7.3 (right) as demonstrated by the ratio SUVmax to background. Data are expressed as mean±SD.

Figure 27:
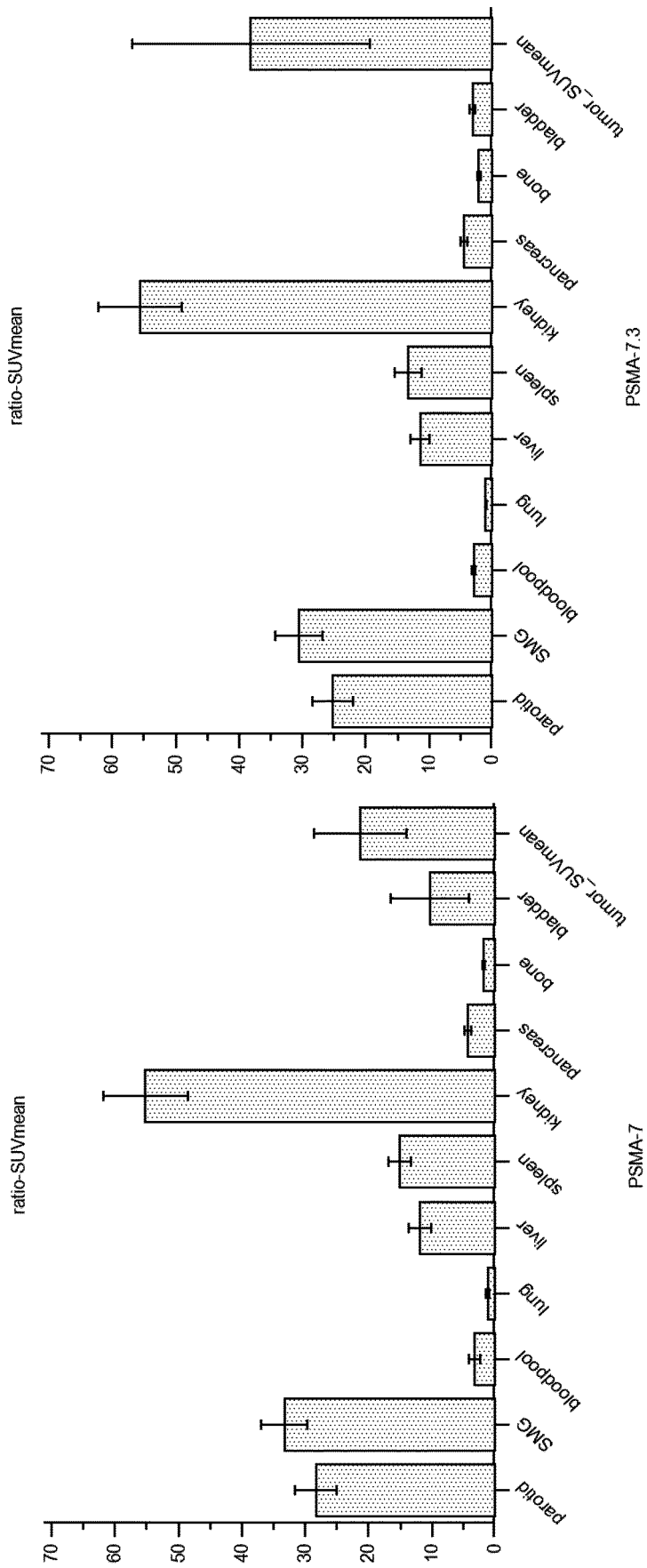

FIG. 27: Clinical biodistribution and uptake in tumor lesions of $^{18}$F-rhPSMA-7 (left) and $^{18}$F-rhPSMA-7.3 (right) as demonstrated by the ratio SUVmean to background. Data are expressed as mean±SD.

Figure 28:
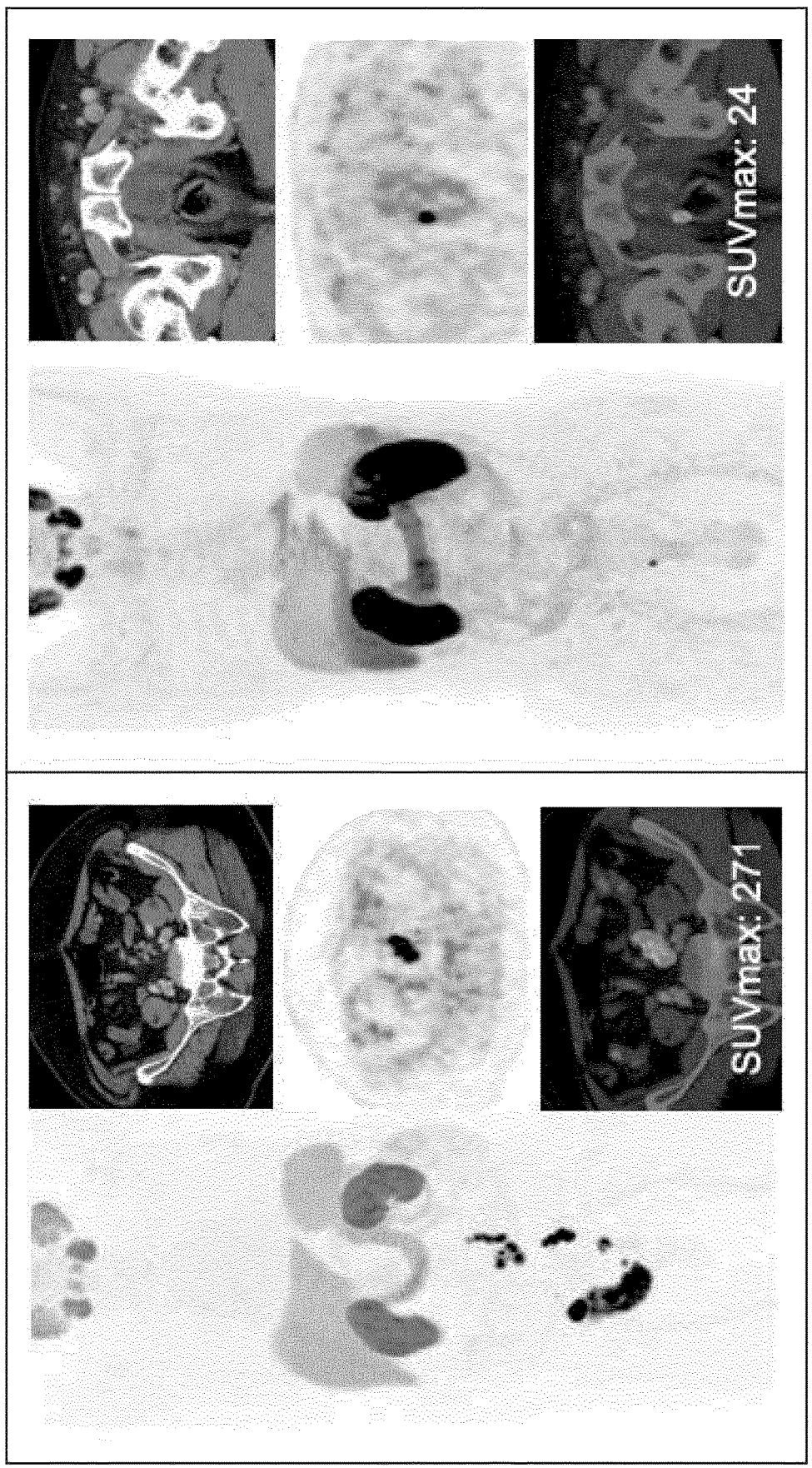

FIG. 28: Two clinical case examples of $^{18}$F-rhPSMA-7.3 PET-imaging.

THE EXAMPLES ILLUSTRATE THE INVENTION

Example 1

Material and Methods

The Fmoc-(9-fluorenylmethoxycarbonyl-) and all other protected amino acid analogs were purchased from Bachem (Bubendorf, Switzerland) or Iris Biotech (Marktredwitz, Germany). The tritylchloride polystyrene (TCP) resin was obtained from PepChem (Tübingen, Germany). Chematech (Dijon, France) delivered the chelators DOTAGA-anhydride, (R)-DOTA-GA(tBu)$_4$ and (S)-DOTA-GA(tBu)$_4$. All necessary solvents and other organic reagents were purchased from either, Alfa Aesar (Karlsruhe, Germany), Sigma-Aldrich (Munich, Germany) or VWR (Darmstadt, Germany). Solid phase synthesis of the peptides was carried out by manual operation using an Intelli-Mixer syringe shaker (Neolab, Heidelberg, Germany). Analytical and preparative reversed-phase high pressure chromatography (RP-HPLC) were performed using Shimadzu gradient systems (Shimadzu Deutschland GmbH, Neufahrn, Germany), each equipped with a SPD-20A UV/Vis detector (220 nm, 254 nm). A Nucleosil 100 C18 (125×4.6 mm, 5 μm particle size) column (CS GmbH, Langerwehe, Germany) was used for analytical measurements at a flow rate of 1 mL/min. Both specific gradients and the corresponding retention times $t_R$ are cited in the text. Preparative HPLC purification was done with a Multospher 100 RP 18 (250×10 mm, 5 μm particle size) column (CS GmbH, Langerwehe, Germany) at a constant flow rate of 5 mL/min. Analytical and preparative radio RP-HPLC was performed using a Nucleosil 100 C18 (5 μm, 125×4.0 mm) column (CS GmbH, Langerwehe, Germany). Eluents for all HPLC operations were water (solvent A) and acetonitrile (solvent B), both containing 0.1% trifluoroacetic acid. Electrospray ionization-mass spectra for characterization of the substances were acquired on an expression$^L$ CMS mass spectrometer (Advion Ltd., Harlow, UK). NMR spectra were recorded on Bruker AVHD-300 or AVHD-400 spectrometers at 300 K. pH values were measured with a Seven Easy pH-meter (Mettler Toledo, Gießen, Germany).

Synthesis Protocols

1) Solid-Phase Peptide Synthesis Following the Fmoc-Strategy

TCP-Resin Loading (GP1)

Loading of the tritylchloride polystyrene (TCP) resin with a Fmoc-protected amino acid (AA) was carried out by stirring a solution of the TCP-resin (1.95 mmol/g) and Fmoc-AA-OH (1.5 eq.) in anhydrous DCM with DIPEA (4.5 eq.) at room temperature for 2 h. Remaining tritylchloride was capped by the addition of methanol (2 mL/g resin) for 15 min. Subsequently the resin was filtered and washed with DCM (2×5 mL/g resin), DMF (2×5 mL/g resin), methanol (5 mL/g resin) and dried in vacuo. Final loading l of Fmoc-AA-OH was determined by the following equation:

$$l\left[\frac{\text{mmol}}{g}\right] = \frac{(m_2 - m_1) \times 1000}{(M_W - M_{HCl})m_2}$$

$m_2$=mass of loaded resin [g]
$m_1$=mass of unloaded resin [g]
$M_w$=molecular weight of AA [g/mol]
$M_{HCl}$=molecular weight of HCl [g/mol]

On-Resin Amide Bond Formation (GP2)

For conjugation of a building block to the resin bound peptide, a mixture of TBTU and HOBT is used for pre-activation with DIPEA or 2,4,6-trimethylpyridine as a base in DMF (10 mL/g resin) for 5 min. The exact stoichiometry and reaction time for each conjugation step is given in the synthesis protocol. After reaction, the resin was washed with DMF (6×5 mL/g resin).

On-Resin Fmoc-Deprotection (GP3)

The resin-bound Fmoc-peptide was treated with 20% piperidine in DMF (v/v, 8 mL/g resin) for 5 min and subsequently for 15 min. Afterwards, the resin was washed thoroughly with DMF (8×5 mL/g resin).

On-Resin Dde-Deprotection (GP4)

The Dde-protected peptide (1.0 eq.) was dissolved in a solution of 2% hydrazine monohydrate in DMF (v/v, 5 mL/g resin) and shaken for 20 min (GP4a). In the case of present Fmoc-groups, Dde-deprotection was performed by adding a solution of imidazole (0.92 g/g resin), hydroxylamine hydrochloride (1.26 g/g reisn) in NMP (5.0 mL) and DMF (1.0 mL) for 3 h at room temperature (GP4b). After deprotection the resin was washed with DMF (8×5 mL/g resin).

Peptide Cleavage from the Resin with Simultaneous Deprotection of Acid Labile Protecting Groups (GP 5)

The fully protected resin-bound peptide was dissolved in a mixture of TFA/TIPS/water (v/v/v; 95/2.5/2.5) and shaken for 30 min. The solution was filtered off and the resin was treated in the same way for another 30 min. Both filtrates were combined, stirred for additional 5 h and concentrated under a stream of nitrogen. After dissolving the residue in a mixture of tert-butanol and water and subsequent lyophilisation the crude peptide was obtained.

$^{nat}$Ga-Complexation (GP6)

For $^{nat}$Ga-complexation, the peptide (1.0 eq.) was dissolved in a 3:1 (v/v) mixture of tBuOH in H$_2$O and an aqueous solution of Ga(NO$_3$)$_3$ (3.5 eq.) was added. After heating the resulting mixture for 30 min at 75° C. the peptide was purified by RP-HPLC.

2) Synthesis of the PSMA Binding Motif

Glu-urea-Glu ((tBuO)EuE(OtBu)2)

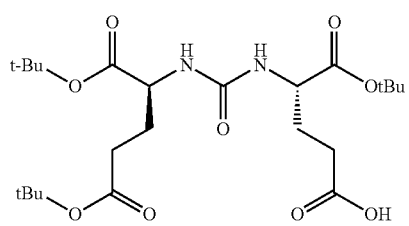 [SMILES: CC(C)(C)OC(=O)CC[C@H](NC(=O)N[C@@H](CCC(=O)O)C(=O)OC(C)(C)C)C(=O)OC(C)(C)C]

The tBu-protected Glu-urea-Glu binding motif (EuE) was synthesized according to a previously published procedure (scheme 1) for tBu-protected Glu-urea-Lys (EuK)[1].

[1]Weineisen, M.; Simecek, J.; Schottelius, M.; Schwaiger, M.; Wester, H. J., Synthesis and preclinical evaluation of DOTAGA-conjugated PSMA ligands for functional imaging and endoradiotherapy of prostate cancer. *EJNMMI research* 2014, 4 (1), 63.

Di-tert-butyl (1H-imidazole-1-carbonyl)-L-glutamate (i)

A solution of DCM containing 2.0 g (7.71 mmol, 1.0 eq.) l-di-tert-butyl-L-glutamate.HCl was cooled on ice for 30 min and afterwards treated with 2.69 mL TEA (19.28 mmol, 2.5 eq.) and 3.3 mg (0.3 mmol, 0.04 eq.) DMAP. After additional stirring for 5 min, 1.38 g (8.84 mmol, 1.1 eq.) of 1,1'-carbonyldiimidazole (CDI) dissolved in DCM were slowly added over a period of 30 min. The reaction mixture was further stirred overnight and enabled to warm to RT. The reaction was stopped using 8 mL saturated NaHCO$_3$ with concomitant washing steps of water (2×) and brine (2×) and dried over Na$_2$SO$_4$. The remaining solvent was removed in vacuo and the crude product (S)-Di-tert-butyl 2-(1H-imidazole-1-carboxamido)pentanedioate (i) was used without further purification.

5-benzyl 1-(tert-butyl) (((S)-1,5-di-tert-butoxy-1,5-dioxopentan-2-yl)carbamoyl)-L-glutamate (ii)

2.72 g (7.71 mmol, 1.0 eq.) of the crude product (S)-Di-tert-butyl-2-(1H-imidazole-1-carboxamido) pentanedioate (i) were dissolved in 1,2-dichloroethane (DCE) and cooled on ice for 30 min. To this solution were added 2.15 mL (15.42 mmol, 2.0 eq.) TFA and 2.54 g (7.71 mmol, 1.0 eq.) H-L-Glu(OBzl)-OtBu.HCl and the solution was stirred overnight at 40° C. The remaining solvent was evaporated and the crude product purified using silica gel flash-chromatography with an eluent mixture containing ethyl acetate/hexane/TFA (500:500:0.8; v/v/v). After removal of the solvent, 5-benzyl-1-(tert-butyl)-WS)-1,5-di-tert-butoxy-1,5-dioxopentan-2-yl)carbamoyl)-L-glutamate (ii) was obtained as a colorless oil.

(tBuO)EuE(OtBu)$_2$ (iii)

To synthesize (tBuO)EuE(OtBu)$_2$, 3.17 g (5.47 mmol, 1.0 eq.) of 5-benzyl-1-(tert-butyl)-(((S)-1,5-di-tert-butoxy-1,5-dioxopentan-2-yl)carbamoyl)-L-glutamate (ii) were dissolved in 75 mL EtOH and 0.34 g (0.57 mmol, 0.1 eq.) palladium on activated charcoal (10%) were given to this solution. The flask containing the reaction mixture was initially purged with H$_2$ and the solution was stirred overnight at room temperature under light H$_2$-pressure (balloon). The crude product was purified through celite and the solvent evaporated in vacuo. The product (iii) was obtained as a hygroscopic solid (84%). HPLC (10% to 90% B in 15 min): $t_R$=11.3 min. Calculated monoisotopic mass (C$_{23}$H$_{49}$N$_2$O$_9$): 488.3; found: m/z=489.4 [M+H]$^+$, 516.4 [M+Na]$^+$.

Scheme 1 Synthesis of (tBuO)EuE(OtBu)$_2$

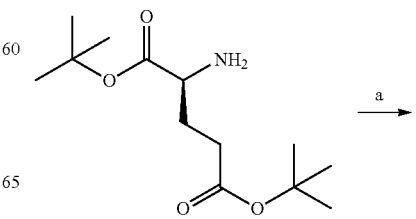

-continued

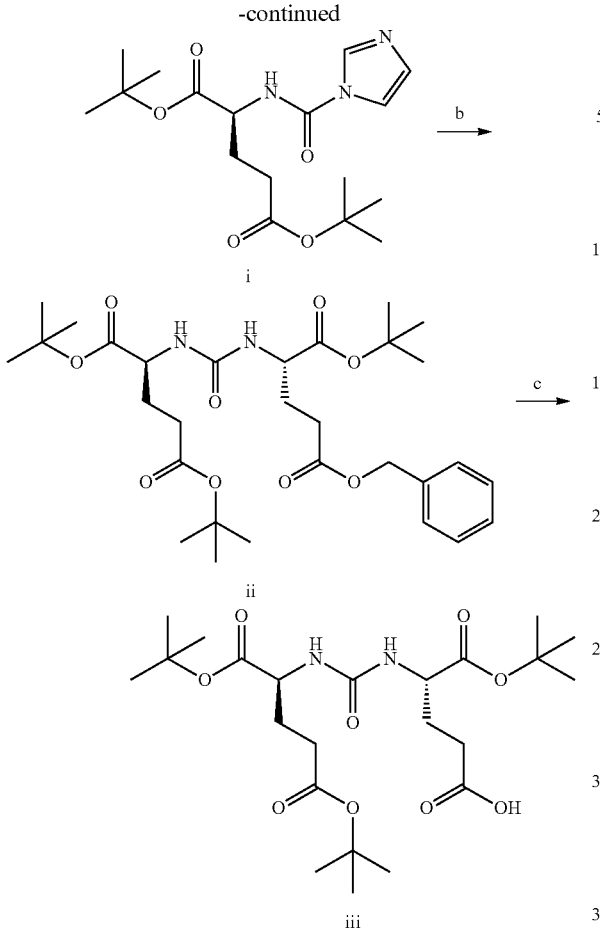

a) DCI, TEA, DMAP (DCM);
b) H—L—Glu(OBzl)—OtBu•HCl, TEA (DCE);
c) Pd/C (10%), H₂ (EtOH).

3) Synthesis of the Silicon-Fluoride Acceptor 4-(Di-tert-butylfluorosilyl)benzoic acid (SiFA-BA)

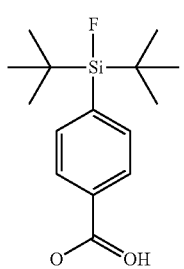 [SMILES: CC(C)(C)[Si](F)(c1ccc(C(=O)O)cc1)C(C)(C)C]

SiFA-BA was synthesized according to a previously published procedure (scheme 2)[2]. All reactions were carried out in dried reaction vessels under argon using a vacuum gas manifold.

[2]Iovkova, L.; Wangler, B.; Schirrmacher, E.; Schirrmacher, R.; Quandt, G.; Boening, G.; Schurmann, M.; Jurkschat, K., para-Functionalized aryl-di-tert-butylfluorosilanes as potential labeling synthons for (18)F radiopharmaceuticals. *Chemistry (Weinheim an der Bergstrasse, Germany)* 2009, 15 (9), 2140-7.

((4-bromobenzyl)oxy)(tert-butyl)dimethylsilane (i)

To a stirred solution of 4-bromobenzylalcohol (4.68 g, 25.0 mmol, 1.0 eq.) in anhydrous DMF (70 mL) imidazole (2.04 g, 30.0 mmol, 1.2 eq.) and TBDMSCI (4.52 g, 30.0 mmol, 1.2 eq.) were added and the resulting mixture was stirred at room temperature for 16 h. The mixture was then poured into ice-cold H₂O (250 mL) and extracted with Et₂O (5×50 mL). The combined organic fractions were washed with sat. aq. NaHCO₃ (2×100 mL) and brine (100 mL), dried, filtered and concentrated in vacuo to give the crude product which was purified by flash column chromatography (silica, 5% EtOAc/petrol) to give i as a colourless oil (7.18 g, 95%). ¹H NMR (400 MHz, CDCl3): δ [ppm]=0.10 (6H, s, SiMe₂t-Bu), 0.95 (9H, s, SiMe₂tBu), 4.69 (2H, s, CH₂OSi), 7.21 (2H, d), 7.46 (2H, d). HPLC (50 to 100% B in 15 min): $t_R$=15 min.

Di-tert-butyl{4-[(tert-butyldimethylsilyloxy)methyl]phenyl}fluorosilane (ii)

At −78° C. under magnetic stirring, a solution of tBuLi in pentane (7.29 mL, 1.7 mol/L, 12.4 mmol 2.4 eq.) was added to a solution of ((4-bromobenzyl)oxy)(tert-butyl)dimethylsilane (i) (1.56 g, 5.18 mmol, 1.0 eq.) in dry THF (15 mL). After the reaction mixture had been stirred for 30 min at −78° C., the suspension obtained was added dropwise over a period of 30 min to a cooled (−78° C.) solution of di-tert-butyldifluorosilane (1.12 g, 6.23 mmol, 1.2 eq.) in dry THF (10 mL). The reaction mixture was allowed to warm to room temperature over a period of 12 h and then hydrolyzed with saturated aqueous NaCl solution (100 mL). The organic layer was separated and the aqueous layer was extracted with diethyl ether (3×50 mL). The combined organic layers were dried over magnesium sulfate and filtered. The filtrate was concentrated in vacuo to afford ii as a yellowish oil (1.88 g, 95%). It was used for subsequent reactions without further purification. NMR spectra were in accordance with the data reported in the literature[2]. HPLC (50 to 100% B in 20 min): $t_R$=19 min.

4-(Di-tert-butylfluorosilanyl)benzyl alcohol (iii)

A catalytic amount of concentrated aqueous HCl (0.5 mL) was added to a suspension of ii (1.88 g, 4.92 mmol, 1.0 eq.) in methanol (50 mL). The reaction mixture was stirred for 18 h at room temperature and then the solvent and the volatiles were removed under reduced pressure. The residue was redissolved in diethyl ether (40 mL) and the solution was washed with saturated aqueous NaHCO₃ solution. The aqueous layer was extracted with diethyl ether (3×50 mL). The combined organic layers were dried over magnesium sulfate and filtered. The filtrate was concentrated in vacuo to afford iii as a yellowish oil (1.29 g, 98%) that solidified. The product was used without further purification. NMR spectra were in accordance with the data reported in the literature[2]. HPLC (50 to 100% B in 15 min): $t_R$=8.2 min.

4-(Di-tert-butylfluorosilyl)benzaldehyde (iv)

A solution of the alcohol iii (1.37 g, 5.10 mmol, 1.0 eq.) in dry dichloromethane (20 mL) was added dropwise to a stirred ice-cooled suspension of pyridinium chlorochromate (2.75 g, 12.8 mmol, 2.5 eq.) in dry dichloromethane (60 mL). After the reaction mixture had been stirred for 30 min at 0° C. and for 2.5 h at room temperature, anhydrous diethyl ether (40 mL) was added and the supernatant solution was decanted from the black gum-like material. The insoluble material was washed thoroughly with diethyl ether and the combined organic phases were passed through a short pad of silica gel (10 cm per g crude product) for filtration. The solvents were removed in vacuo to yield aldehyde iv as a yellowish oil (1.31 g, 96%). NMR spectra were in accordance with the data reported in the literature[2]. HPLC (50 to 100% B in 15 min): $t_R$=10.5 min.

4-(Di-tert-butylfluorosilyl)benzoic acid (v)

At room temperature, 1 M aqueous $KMnO_4$ (30 mL) was added to a mixture of iv (1.31 g, 4.92 mmol, 1.0 eq.), tert-butanol (30 mL), dichloromethane (3.3 mL), and 1.25 M $NaH_2PO_4 \cdot H_2O$ buffer (20 mL) at pH 4.0-4.5. After the mixture had been stirred for 25 min, it was cooled to 5° C., whereupon excess $KMnO_4$ (0.78 g, 4.92 mmol, 1.0 eq.) was added. The reaction was then quenched by the addition of saturated aqueous $Na_2SO_3$ solution (50 mL). Upon addition of 2 M aqueous HCl, all of the $MnO_2$ dissolved. The resulting solution was extracted with diethyl ether (3×100 mL). The combined organic layers were washed with saturated aqueous $NaHCO_3$ solution, dried over $MgSO_4$, filtered, and concentrated under reduced pressure to provide a white solid, which was purified by recrystallization from $Et_2O$/n-hexane (1:3, for 12 h) to give v (0.84 g, 60%). NMR spectra were in accordance with the data reported in the literature[2]. HPLC (50 to 100% B in 15 min): $t_R$=8.5 min.

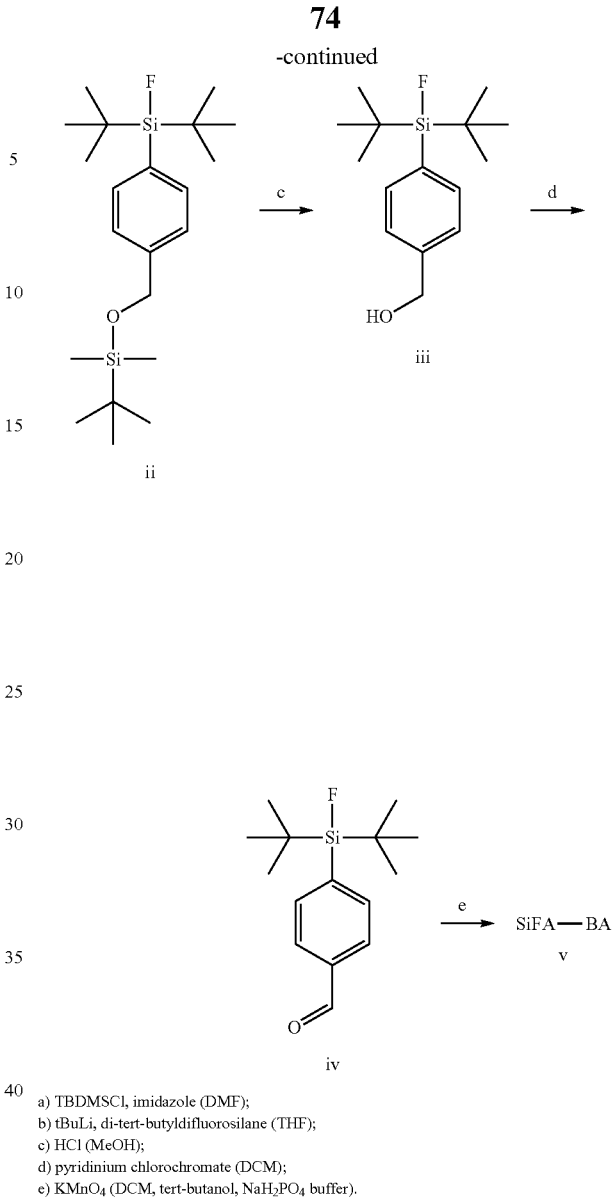

a) TBDMSCl, imidazole (DMF);
b) tBuLi, di-tert-butyldifluorosilane (THF);
c) HCl (MeOH);
d) pyridinium chlorochromate (DCM);
e) $KMnO_4$ (DCM, tert-butanol, $NaH_2PO_4$ buffer).

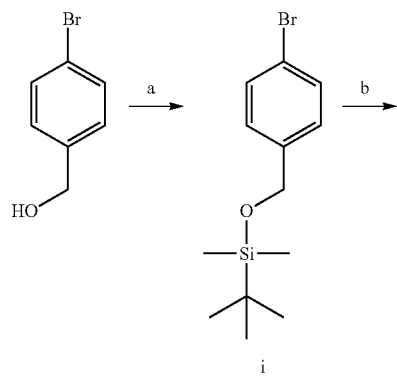

Scheme 2 Synthesis of SiFA—BA

4) Synthesis of rhPSMA-7.1-7.4

The first synthetic steps for preparation of the four different isomers of rhPSMA-7 are identical and carried out together, applying the standard Fmoc-SPPS protocol described above, starting from resin bound Fmoc-D-Orn (Dde)-OH. After cleavage of the Fmoc group with 20% piperidine in DMF (GP3), (tBuO)EuE(OtBu)$_2$ (2.0 eq.) was conjugated with HOAt (2.0 eq.), TBTU (2.0 eq.) and DIPEA (6.0 eq.) in DMF for 4.5 h. After cleavage of the Dde-group with a mixture of 2% hydrazine in DMF (GP4a), a solution of succinic anhydride (7.0 eq.) and DIPEA (7.0 eq.) in DMF was added and left to react for 2.5 h. Conjugation of Fmoc-D-Lys(OtBu).HCl (2.0 eq.) was achieved by adding a mixture of HOAt (2.0 eq.), TBTU (2.0 eq.) and DIPEA (6.0 eq.) in DMF to the resin. After pre-activation for 5 min, Fmoc-D-Lys(OtBu).HCl (2.0 eq.) dissolved in DMF was added and left to react for 2.5 h (GP2). Subsequent cleavage of the Fmoc-group was performed, by adding a mixture of 20% piperidine in DMF (GP3). Finally, the resin was split in order to synthesize rhPSMA-7.1-7.4 (scheme 3).

rhPSMA-7.1 (D-Dap-(R)-DOTA-GA):

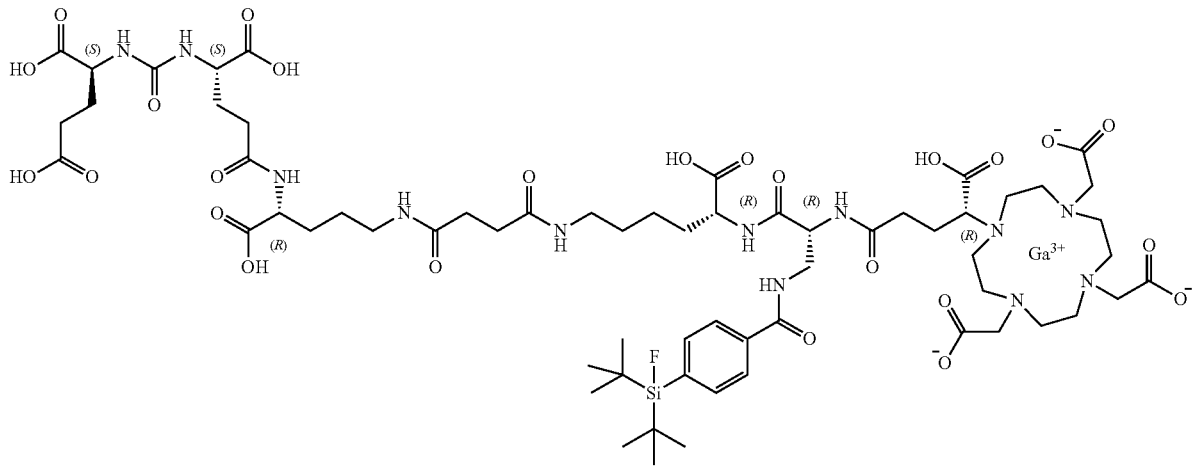

Fmoc-D-Dap(Dde)-OH (2.0 eq.) was pre-activated in a mixture of HOAt (2.0 eq.), TBTU (2.0 eq.) and 2,4,6-trimethylpyridine (6.7 eq.) in DMF and added to the resin-bound peptide for 2.5 h. Following orthogonal Dde-deprotection was done using imidazole and hydroxylamine hydrochloride dissolved in a mixture of NMP and DMF for 3 h. SiFA-BA (1.5 eq.) was reacted with the free amine of the side chain with HOAt (1.5 eq.), TBTU (1.5 eq.) and DIPEA (4.5 eq.), as activation reagents in DMF for 2 h. After Fmoc-deprotection with piperidine (GP3), (R)-DOTA-GA (tBu)$_4$ (2.0 eq.) was conjugated with HOAT (2.0 eq.), TBTU (2.0 eq.) and 2,4,6-trimethylpyridine (6.7 eq.) in DMF for 2.5 h. Cleavage from the resin with simultaneous deprotection of acid labile protecting groups was performed in TFA, according to GP5. $^{nat}$Ga-complexation of the peptide was carried out, as described in GP6.

rhPSMA-7.2 (L-Dap-(R)-DOTA-GA):

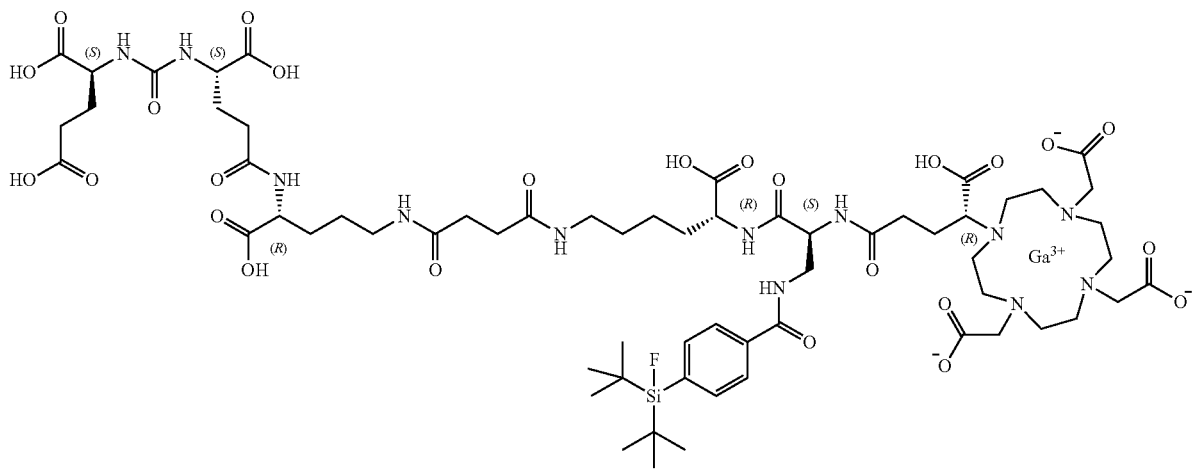

Fmoc-L-Dap(Dde)-OH (2.0 eq.) was pre-activated in a mixture of HOAt (2.0 eq.), TBTU (2.0 eq.) and 2,4,6-trimethylpyridine (6.7 eq.) in DMF for 2.5 h. Following orthogonal Dde-deprotection, conjugation of SiFA-BA and Fmoc-cleavage was carried out as described for rhPSMA-7.1. (R)-DOTA-GA(tBu)$_4$ (2.0 eq.) was conjugated with HOAT (2.0 eq.), TBTU (2.0 eq.) and 2,4,6-trimethylpyridine (6.7 eq.) in DMF for 2.5 h. Cleavage from the resin with simultaneous deprotection of acid labile protecting groups was performed in TFA according to GP5. $^{nat}$Ga-complexation of the peptide was carried out, as described in GP6. rhPSMA-7.3 (D-Dap-(S)-DOTA-GA):

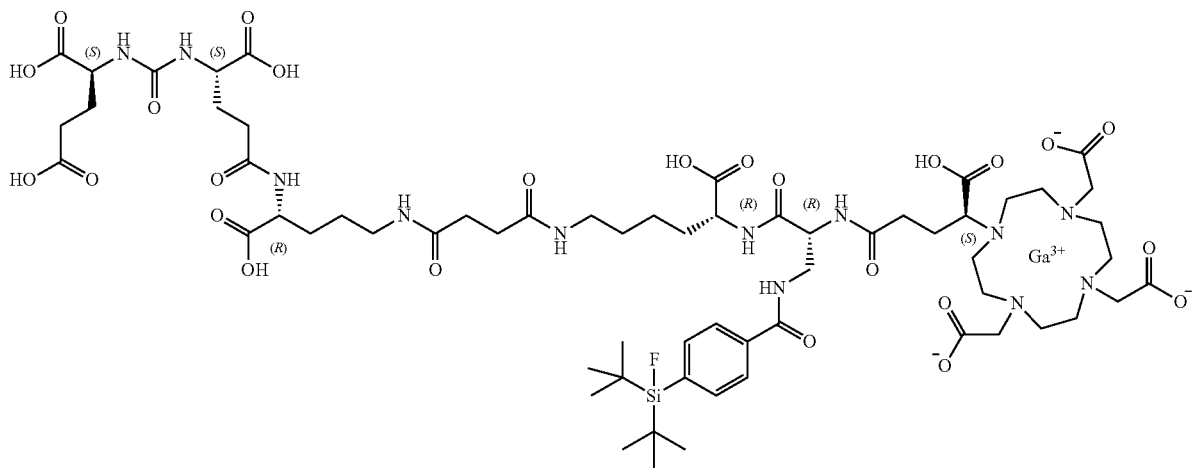

Fmoc-D-Dap(Dde)-OH (2.0 eq.) was pre-activated in a mixture of HOAt (2.0 eq.), TBTU (2.0 eq.) and 2,4,6-trimethylpyridine (6.7 eq.) in DMF for 2.5 h. Following orthogonal Dde-deprotection, conjugation of SiFA-BA and Fmoc-cleavage was carried out as described for rhPSMA-7.1. (S)-DOTA-GA(tBu)$_4$ (2.0 eq.) was conjugated with HOAT (2.0 eq.), TBTU (2.0 eq.) and 2,4,6-trimethylpyridine (6.7 eq.) in DMF for 2.5 h. Cleavage from the resin with simultaneous deprotection of acid labile protecting groups was performed in TFA according to GP5. $^{nat}$Ga-complexation of the peptide was carried out, as described in GP6. rhPSMA-7.4 (L-Dap-(S)-DOTA-GA):

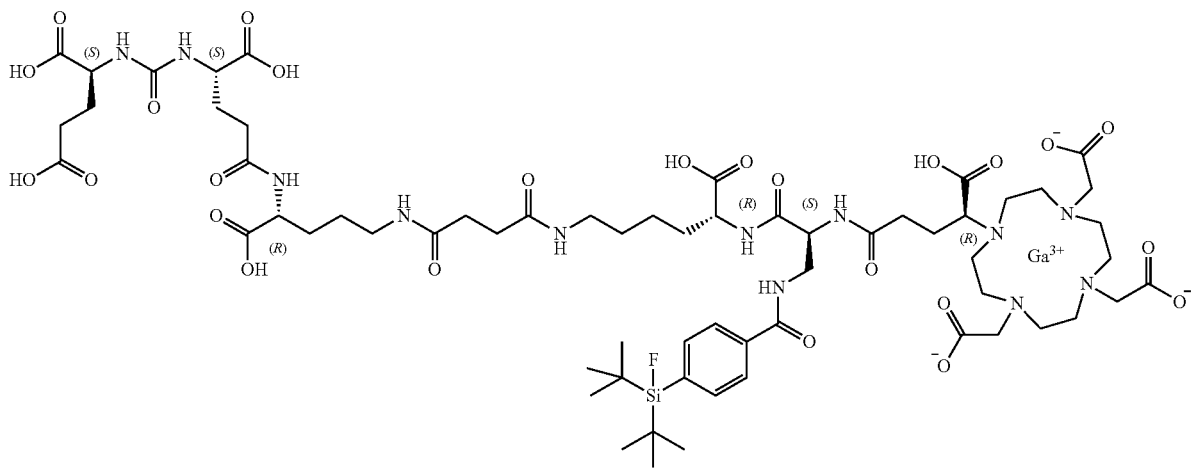

Fmoc-L-Dap(Dde)-OH (2.0 eq.) was pre-activated in a mixture of HOAt (2.0 eq.), TBTU (2.0 eq.) and 2,4,6-trimethylpyridine (6.7 eq.) in DMF for 2.5 h. Following orthogonal Dde-deprotection, conjugation of SiFA-BA and Fmoc-cleavage was carried out as described for rhPSMA-7.1. (S)-DOTA-GA(tBu)$_4$ (2.0 eq.) was conjugated with HOAT (2.0 eq.), TBTU (2.0 eq.) and 2,4,6-trimethylpyridine (6.7 eq.) in DMF for 2.5 h. Cleavage from the resin with simultaneous deprotection of acid labile protecting groups was performed in TFA according to GP5. $^{nat}$Ga-complexation of the peptide was carried out, as described in GP6.

rhPSMA-7.1:
  HPLC (10 to 70% B in 15 min): $t_R$=10.5 min.
  HPLC (25 to 35%B in 40 min): $t_R$=31.4 min.
rhPSMA-7.2:
  HPLC (10 to 70% B in 15 min): $t_R$=10.4 min.
  HPLC (25 to 35%B in 40 min): $t_R$=27.9 min.
rhPSMA-7.3:
  HPLC (10 to 70% B in 15 min): $t_R$=10.4 min.
  HPLC (25 to 35%B in 40 min): $t_R$=28.1 min.
rhPSMA-7.4:
  HPLC (10 to 70% B in 15 min): $t_R$=10.5 min.
  HPLC (25 to 35%B in 40 min): $t_R$=29.1 min.
rhPSMA-7.1-7.4:
  Calculated monoisotopic mass ($C_{63}H_{96}FGaN_{12}O_{25}Si$): 1536.6 found: m/z=1539.4 [M+H]+, 770.3 [M+2H]$2^+$.

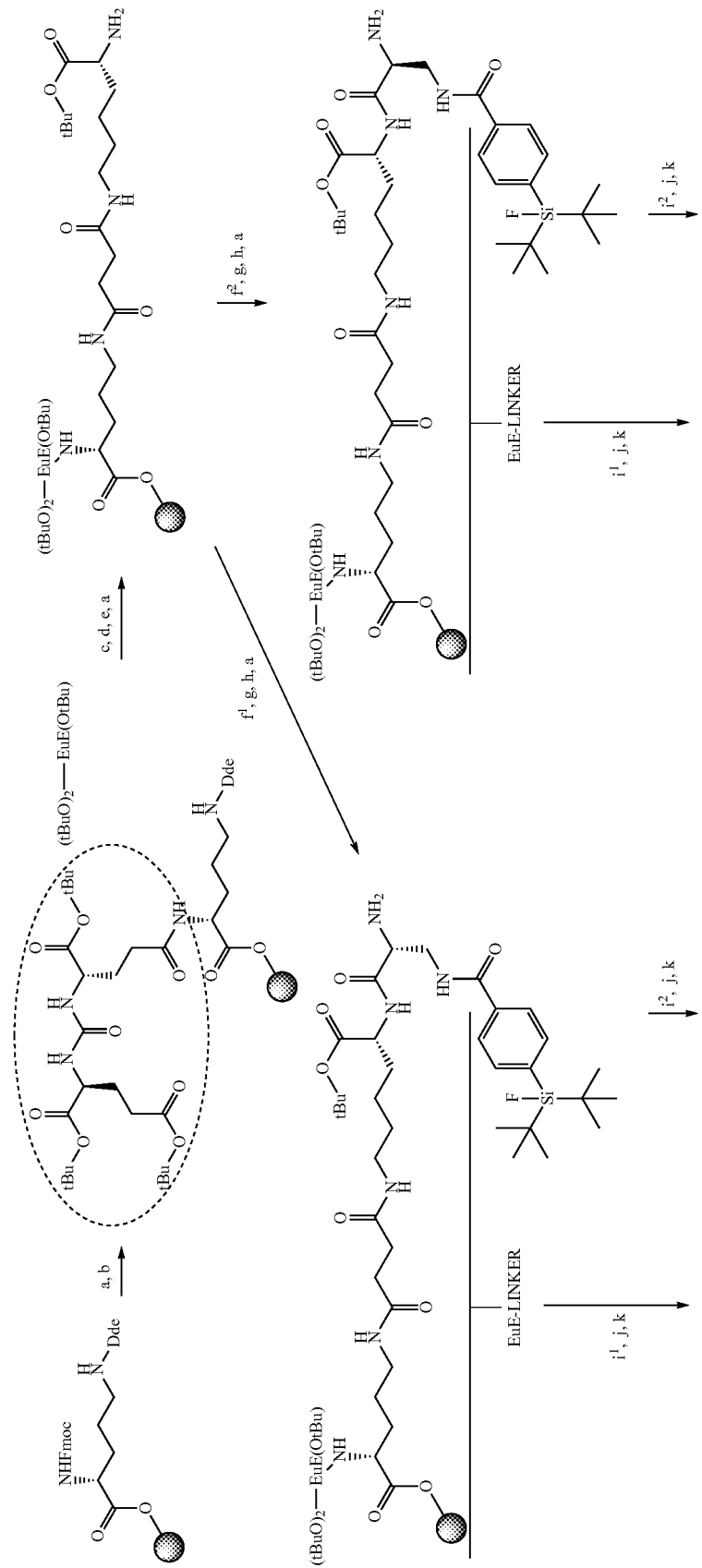

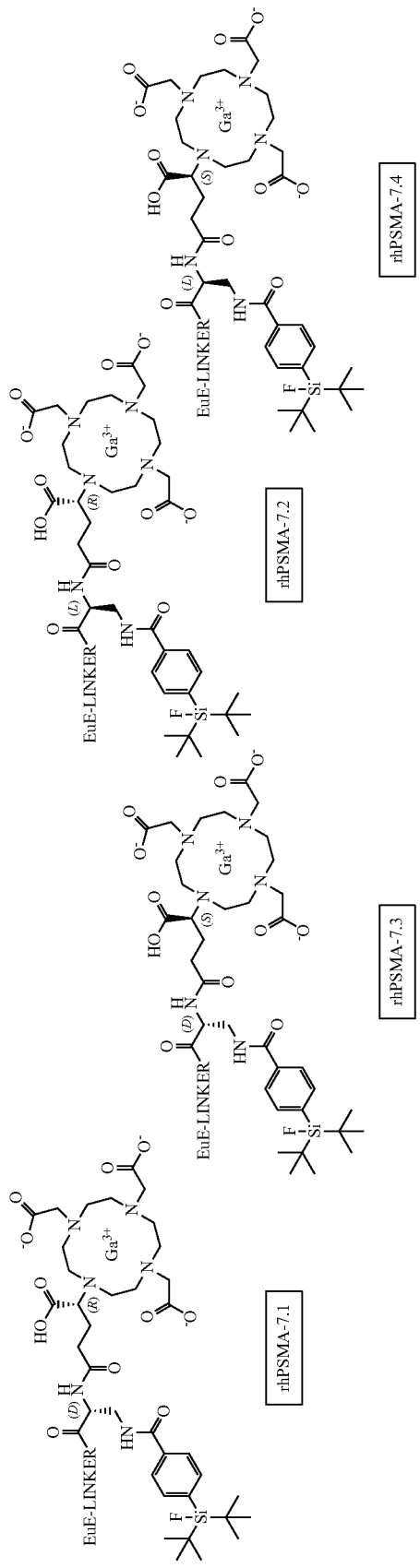

a) 20% piperidine, (DMF);
b) (tBuO)EuE(OtBu)2, HOAt, TBTU, DIPEA, (DMF);
c) 2% hydrazine (DMF);
d) succinic anhydride, DIPEA, (DMF);
e) Fmoc—D—Lys(OtBu)·HCl, HOAt, TBTU, DIPEA, (DMF);
f¹) Fmoc—D—Dap(Dde)—OH, HOAt, TBTU, 2,4,6-collidine, (DMF);
f²) Fmoc—L—Dap(Dde)—OH, HOAt, TBTU, 2,4,6-collidine, (DMF);
g) imidazole, hydroxylamine hydrochloride, (NMP, DMF);
h) SiFA—BA, HOAt, TBTU, DIPEA (DMF);
i¹) (R)—DOTA—GA(tBu)₄, HOAt, TBTU, 2,4,6-collidine (DMF);
i²) (S)—DOTA—GA(tBu)4, HOAt, TBTU, 2,4,6-collidine (DMF);
j) cleavage and deprotection: TFA, TIPS, H₂O;
k) Ga(NO₃)₃, (tBuOH, H₂O).

5) $^{18}$F-Labeling

For $^{18}$F-labeling a previously published procedure[3] was applied, which was slightly modified. Briefly, aqueous $^{18}$F was passed through a SAX cartridge (Sep-Pak Accell Plus QMA Carbonate light), which was preconditioned with 10 mL of water. After drying with 10 mL of air, water was removed, by rinsing the cartridge with 10 mL of anhydrous acetonitrile followed by 20 mL of air. $^{18}$F was eluted with 100 μmol of [K$^+$ ⊂ 2.2.2]OH$^-$ dissolved in 500 μL of anhydrous acetonitrile. Before labelling, 30 μmol of oxalic acid in anhydrous acetonitrile (1 M, 30 μL) were added. This mixture was used as a whole or aliquot for fluorination of 10-25 nmol of PSMA-SiFA (1 mM in anhydrous DMSO). The resulting reaction mixture was incubated for 5 minutes at room temperature. For purification of the tracer, a Sep-Pak C18 light cartridge, preconditioned with 10 mL EtOH, followed by 10 mL of H$_2$O was used. The labeling mixture was diluted with 9 mL PBS (pH 3) and passed through the cartridge followed by 10 mL of H$_2$O. The peptide was eluted with 500 μL of a 4:1 mixture (v/v) of EtOH in water. Radiochemical purity of the labelled compound was determined by radio RP-HPLC and radio-TLC (Silica gel 60 RP-18 F$_{254}$s, mobile phase: 3:2 mixture (v/v) of MeCN in H$_2$O supplemented with 10% of 2 M aqueous NaOAc and 1% of TFA).

[3]Wangler, C.; Niedermoser, S.; Chin, J.; Orchowski, K.; Schirrmacher, E.; Jurkschat, K.; Iovkova-Berends, L.; Kostikov, A. P.; Schirrmacher, R.; Wangler, B., One-step (18)F-labeling of peptides for positron emission tomography imaging using the SiFA methodology. Nat Protoc 2012, 7 (11), 1946-55.

6) $^{125}$I-Labeling

The reference ligand for in vitro studies ([$^{125}$I]I-BA)KuE was prepared according to a previously published procedure[1]. Briefly, 0.1 mg of the stannylated precursor (SnBu$_3$-BA)(OtBu)KuE(OtBu)$_2$ was dissolved in a solution containing 20 μL peracetic acid, 5.0 μL (21 MBq) [$^{125}$I]NaI (74 TBq/mmol, 3.1 GBq/mL, 40 mM NaOH, Hartmann Analytic, Braunschweig, Germany), 20 μL MeCN and 10 μL acetic acid. The reaction solution was incubated for 10 min at RT, loaded on a cartridge and rinsed with 10 mL water (C18 Sep Pak Plus cartridge, preconditioned with 10 mL MeOH and 10 mL water). After elution with 2.0 mL of a 1:1 mix (v/v) of EtOH/MeCN, the radioactive solution was evaporated to dryness under a gentle nitrogen stream and treated with 200 μL TFA for 30 min with subsequent evaporation of TFA. The crude product of ([$^{125}$I]I-BA)KuE was purified by RP-HPLC (20% to 40% B in 20 min): $t_R$=13.0 min.

In Vitro Experiments

1) Determination of IC$_{50}$

The PSMA-posivite LNCaP cells were grown in Dublecco modified Eagle medium/Nutrition Mixture F-12 with Glutamax-I (1:1) (Invitrigon), supplemented with 10% fetal calf serum and maintained at 37° C. in a humidified 5% CO$_2$ atmosphere. For determination of the PSMA affinity (IC$_{50}$), cells were harvested 24±2 hours before the experiment and seeded in 24-well plates (1.5×10$^5$ cells in 1 mL/well). After removal of the culture medium, the cells were treated once with 500 μL of HBSS (Hank's balanced salt solution, Biochrom, Berlin, Germany, with addition of 1% bovine serum albumin (BSA)) and left 15 min on ice for equilibration in 200 μL HBSS (1% BSA). Next, 25 μL per well of solutions, containing either HBSS (1% BSA, control) or the respective ligand in increasing concentration (10$^{-10}$-10$^{-4}$ M in HBSS), were added with subsequent addition of 25 μL of ([$^{125}$I]I-BA)KuE (2.0 nM) in HBSS (1% BSA). All experiments were performed at least three times for each concentration. After 60 min incubation on ice, the experiment was terminated by removal of the medium and consecutive rinsing with 200 μL of HBSS. The media of both steps were combined in one fraction and represent the amount of free radioligand. Afterwards, the cells were lysed with 250 μL of 1 M NaOH and united with the 200 μL HBSS of the following wash step. Quantification of bound and free radioligand was accomplished in a γ-counter.

2) Internalization

For internalization studies, LNCaP cells were harvested 24±2 hours before the experiment and seeded in 24-well plates (1.25×10$^5$ cells in 1 mL/well). Subsequent to the removal of the culture medium, the cells were washed once with 500 μL DMEM-F12 (5% BSA) and left to equilibrate for at least 15 min at 37° C. in 200 μL DMEM-F12 (5% BSA). Each well was treated with either 25 μL of either DMEM-F12 (5% BSA) or a 100 μM PMPA solution for blockade. Next, 25 μL of the $^{68}$Ga/$^{18}$F-labeled PSMA inhibitor (5.0 nM) was added and the cells incubated at 37° C. for 60 min. The experiment was terminated by placing the 24-well plate on ice for 3 min and consecutive removal of the medium. Each well was rinsed with 250 μL HBSS and the fractions from these first two steps combined, representing the amount of free radioligand. Removal of surface bound activity was accomplished by incubation of the cells with 250 μL of ice-cold PMPA (10 μM in PBS) solution for 5 min and rinsed again with another 250 μL of ice-cold PBS. The internalized activity was determined by incubation of the cells in 250 μL 1 M NaOH and the combination with the fraction of a subsequent wash step with 250 μL 1.0 M NaOH. Each experiment (control and bloackde) was performed in triplicate. Free, surface bound and internalized activity was quantified in a γ-counter. All internalization studies were accompanied by reference studies using ([$^{125}$I]I-BA)KuE (c=0.2 nM), which were performed analogously. Data were corrected for non-specific internalization and normalized to the specific-internalization observed for the radioiodinated reference compound.

3) Octanol-Water Partition Coefficient

Approximately 1 MBq of the labeled tracer was dissolved in 1 mL of a 1:1 mixture (by volumes) of phosphate buffered saline (PBS, pH 7.4) and n-octanol in an Eppendorf tube. After vigorous mixing of the suspension for 3 minutes at room temperature, the vial was centrifuged at 15000 g for 3 minutes (Biofuge 15, Heraus Sepatech, Osterode, Germany) and 100 μL aliquots of both layers were measured in a gamma counter. The experiment was repeated at least six times.

4) HSA Binding

For the determination of HSA binding, a Chiralpak HSA column (50×3 mm, 5 μm, H13H-2433) was used at a constant flow rate of 0.5 mL/min. The mobile phase (A: NH$_4$OAc, 50 mM in water, pH 7 and B: isopropanol) was freshly prepared for each experiment and only used for one day. The column was kept at room temperature and each run was stopped after detection of the signal to reduce the acquisition time. All substances were dissolved in a 0.5 mg/ml concentration in 50% 2-propanol and 50% 50 mM pH 6.9 ammonium acetate buffer. The chosen reference substances display a range of HSA binding from 13% to 99% since a broad variety of albumin binding regarding the peptides was assumed. All nine reference substances were injected consecutively to establish a non-linear regression with Origin Pro 2016G.

TABLE 1

Reference substances[4] used for the calibration of the HSA-column.

| Reference | $t_R$ | Log $t_R$ | Lit. HSA % | Log K HSA |
|---|---|---|---|---|
| p-benzylalcohol | 2.40 | 0.38 | 13.15 | −0.82 |
| Aniline | 2.72 | 0.43 | 14.06 | −0.79 |
| Phenol | 3.28 | 0.52 | 20.69 | −0.59 |
| Benzoic Acid | 4.08 | 0.61 | 34.27 | −0.29 |
| Carbamazepine | 4.15 | 0.62 | 75.00 | 0.46 |
| p-nitrophenol | 5.62 | 0.75 | 77.65 | 0.52 |
| Estradiol | 8.15 | 0.91 | 94.81 | 1.19 |
| Probenecid | 8.84 | 0.95 | 95.00 | 1.20 |
| Glibenclamide | 29.18 | 1.47 | 99.00 | 1.69 |

The retention time is shown exemplary for a conducted experiment; $t_R$ retention time; Lit. HSA literature value of human serum albumin binding in [%]; Log K HAS logarithmic K of human serum albumin binding.
[4]Yamazaki, K.; Kanaoka, M., Computational prediction of the plasma protein-binding percent of diverse pharmaceutical compounds. *Journal of pharmaceutical sciences* 2004, 93 (6), 1480-94.

In Vivo Experiments

All animal experiments were conducted in accordance with general animal welfare regulations in Germany and the institutional guidelines for the care and use of animals. To establish tumor xenografts, LNCaP cells ($10^7$ cells/200 μL) were suspended in a 1:1 mixture (v/v) of Dulbecco modified Eagle medium/Nutrition Mixture F-12 with Glutamax-I (1:1) and Matrigel (BD Biosciences, Germany), and inoculated subcutaneously onto the right shoulder of 6-8 weeks old CB17-SCID mice (Charles River, Sulzfeld, Germany). Mice were used for when tumors had grown to a diameter of 5-8 mm (3-4 weeks after inoculation).

1) Biodistribution

Approximately 1-2 MBq (<0.2 nmol) of the $^{18}$F-labeled PSMA inhibitor was injected into the tail vein of LNCaP tumor-bearing male CB-17 SCID mice and sacrificed after 1 h post injection (n=4-5). Selected organs were removed, weighted and measured in a γ-counter 2) Metabolism Studies a) Analytical Set-Up Analytical reversed-phase high pressure chromatography (RP-HPLC) were performed using Shimadzu gradient systems (Shimadzu Deutschland GmbH, Neufahrn, Germany), equipped with a SPD-20A UV/Vis detector (220 nm, 254 nm). A Multospher 100 RP18 (125×4.6 mm, 5 μm particle size) column (CS GmbH, Langerwehe, Germany) was used for analytical measurements at a flow rate of 1 mL/min. Eluents for all HPLC operations were water (solvent A) and acetonitrile (solvent B), both containing 0.1% trifluoroacetic acid. Radioactivity was detected through connection of the outlet of the UV-photometer to a HERM LB 500 detector (Berthold Technologies GmbH, Bad Wildbad, Germany). The gradient for all HPLC operations was: 5% B isocratic 0-3 min, 25-35% B 3-43 min, 95-95% B 43-48 min.

For radio-thin-layer chromatography, aluminum sheets coated with silica gel 60 RP-18 $F_{254}$s were used with a mobile phase consisting of a 3:2 mixture (v/v) of MeCN in $H_2O$ supplemented with 10% of 2 M aqueous NaOAc and 1% of TFA. Analysis was performed using either a Scan-RAM radio-TLC detector (LabLogic Systems Ltd., Sheffield, United Kingdom) or a CR 35 BIO phosphorimager (Duerr Medical GmbH, Bietigheim-Bissingen, Germany).

b) Determination of Metabolic Stability of rhPSMA-7.1-7.4

For in vivo μmetabolism studies, 8-12 MBq (<0.6 nmol) of the respective $^{18}$F-labeled ligand (rhPSMA-7.1-7.4) was injected into the tail vein of female healthy CB17-SCID mice (n=4). Mice were left under anesthesia for 30 min and the urine was collected using a bladder catheter. Urine samples were pooled and centrifuged for 5 min at 9000 rpm to remove suspended solids. The supernatant was directly used for radio-HPLC analysis with the above mentioned conditions. In order to demonstrate that isotopic exchange of $^{19}$F with peptide-bound $^{18}$F is taking place in urine, each compound was incubated for certain time intervals with urine samples of female healthy CB-17-SCID mice, which where analysed by radio-HPLC and/or radio-TLC. Additionally, this experiment was carried out with the addition of excess $Na^{19}F$ (0.5 μmol) and incubation for 2 h with $^{18}$F-labeled rhPSMA-7.3.

c) Determination of In Vivo Distribution of rhPSMA-7.1-7.4

In order to quantify the relative uptake of each isomer (rhPSMA-7.1-7.4), a tumor-bearing male CB-17-SCID mouse was injected with the racemic mixture of rhPSMA-7 (180-280 MBq, $S_A$=247-349 GBq/μmol, produced at the Klinikum rechts der Isar in a fully automated procedure). The animal was left under anesthesia for 30 min and sacrificed. Urine, blood, liver, kidneys and tumor were collected and processed to the hereafter described procedures. The urine sample was centrifuged for 5 min at 9000 rpm to yield a clear solution and directly subjected to radio-HPLC analysis. Blood was diluted to 1 mL with $H_2O$ and centrifuged twice at 13000 g for 5 min. The supernatant was collected and loaded on a Strata X cartridge (33 μm Polymeric Reversed Phase 500 mg, pre-conditioned with 5 mL MeOH, followed by 5 mL $H_2O$). After washing with 5 mL $H_2O$, the cartridge was eluted with a 6:4 mixture (v/v) of MeCN in $H_2O$, supplemented with 1% TFA. The eluate was diluted with water and analysed by radio-HPLC. Tumour, kidneys and liver were homogenised using either a Potter-Elvehjem tissue grinder (Kontes Glass Co, Vineland, USA) or a MM-400 ball mill (Retsch GmbH, Haan, Germany).

I) Potter-Elvehjem Tissue Grinder

Tumour and kidneys were separately homogenised in the tissue homogeniser with 1 mL of extraction buffer (850 μL 1 M HEPES pH7.4, 100 μL20 mM PMPA and 100 μL 1M NaCl) for 30 min. The resulting homogenate was collected and centrifuged at 13000 g for 5 min. Subsequently the supernatant was collected, centrifuged again (13000 g, 5 min) and loaded on a Strata X cartridge (33 μm Polymeric Reversed Phase 500 mg, pre-conditioned with 5 mL MeOH, followed by 5 mL $H_2O$). After washing with 5 mL $H_2O$, the cartridge was eluted with a 6:4 mixture (v/v) of MeCN in $H_2O$, supplemented with 1% TFA. The eluate of each organ was diluted with water and analysed by radio-HPLC.

II) MM-400 Ball Mill

The organs (tumour, kidney, liver) were separately homogenised in a 2 mL tube together with 3 grinding balls (3 mm diameter) and 1 mL of extraction buffer (850 μL 1 M HEPES pH7.4, 100 μL 20 mM PMPA and 100 μL 1M NaCl) for 10 min at 30 Hz. The homogenate was centrifuged at 13000 g for 5 min and the supernatant was collected. Subsequently, the pellet was suspended in 1 mL of extraction buffer and homogenized again with the ball mill for 10 min at 30 Hz. After centrifugation (13000 g, 5 min), both supernatants were combined and loaded on a Strata X cartridge (33 μm Polymeric Reversed Phase 500 mg, pre-conditioned with 5 mL MeOH, followed by 5 mL $H_2O$). After washing with 5 mL $H_2O$, the cartridge was eluted with a 6:4 mixture (v/v) of MeCN in $H_2O$, supplemented with 1% TFA. The eluate of each organ was diluted with water and analysed by radio-HPLC. In order to demonstrate that the breakthrough during cartridge loading, is not a result of unbound F-18, the supernatant was also examined by radio-TLC after centrifugation. Finally the ratios of the individual isomers were determined from the HPLC profiles of the extracted samples and compared to the ratios of the isomers from the quality control of the racemic mixture of rhPSMA-7. The decay corrected extraction- and cartridge loading-efficiency, as well as the overall extracted activity of the examined samples are given in table 2. The cartridge elution-efficiency was >99% for all experiments.

Example 2

Results

Chromatographic Peak Assignment

The chromatographic peak assignment was carried out by comparison of the UV profiles of
a) the rhPSMA7-rac micture with
b) the rhPSMA7-rac micture coninjected with each enantiopure rhPSMA7 compound.
The following names are used for the different isomers:
rhPSMA-rac: [$^{19}$F][$^{nat}$Ga]D/L-Dap-R/S-DOTAGA-rhPSMA7
rhPSMA-7-1: [$^{19}$F][$^{nat}$Ga]D-Dap-R-DOTAGA-rhPSMA7
rhPSMA-7-2: [$^{19}$F][$^{nat}$Ga]L-Dap-R-DOTAGA-rhPSMA7
rhPSMA-7-3: [$^{19}$F][$^{nat}$Ga]D-Dap-S-DOTAGA-rhPSMA7
rhPSMA-7-4: [$^{19}$F][$^{nat}$Ga]L-Dap-S-DOTAGA-rhPSMA7

TABLE 2

Assignment of the different isomers, names, typical retention times (HPLC conditions are given in FIG. 2a-4b, and percentage of each isomer on a typical rhPSAM7-rac mixture. The exact amount can vary for each isomer.

| ligand | Name | $t_R$ [min] | typical percentage of whole mixture |
|---|---|---|---|
| [$^{19}$F][$^{nat}$Ga]D-Dap-R-DOTAGA-rhPSMA7 | rhPSMA-7-1 | 31.6 | 21 |
| [$^{19}$F][$^{nat}$Ga]L-Dap-R-DOTAGA-rhPSMA7 | rhPSMA-7-2 | 28.3 | 22 |
| [$^{19}$F][$^{nat}$Ga]D-Dap-S-DOTAGA-rhPSMA7 | rhPSMA-7-3 | 28.9 | 37 |
| [$^{19}$F][$^{nat}$Ga]L-Dap-S-DOTAGA-rhPSMA7 | rhPSMA-7-4 | 30.1 | 20 |

Binding Affinities

The first set of values (rhPSMA-7.1 and rhPSMA-7.2; FIG. 6a) were determined by using for the dilution series a solution directly obtained after $^{nat}$Ga-complexation of the respective ligand. In the second data set (FIG. 6b), the complexed ligands were purified by RP-HPLC in order to separate uncomplexed $^{nat}$Ga-salts. Since there were no significant differences observed, both series were merged and used for the calculation of the mean values (±SD).

TABLE 3

Depiction of the individual IC$_{50}$ [nM] measurements (as shown in FIG. 6a and 6b). Conditions as described in the legend to FIG. 6a.

| No | rhPSMA7.1 | rhPSMA7.2 | rhPSMA7.3 | rhPSMA7.4 |
|---|---|---|---|---|
| 1 | 8.74 | 3.17 | nd | nd |
| 2 | 6.91 | 2.97 | nd | nd |
| 3 | 7.27 | 3.36 | nd | nd |
| 4 | 5.04 | 2.64 | 3.17 | 3.4 |
| 5 | ~~1.21 (*)~~ | 2.76 | 2.91 | 3.56 |
| 6 | 7.11 | 3.94 | 5.35 | 2.79 |
| 7 | 8.31 | 5.8 | 5.74 | 4.57 |
| 8 | 4.97 | 4.31 | 4.59 | 3.78 |
| 9 | 6.44 | 4.32 | 4.45 | nd |
| Mean | 6.85 | 3.70 | 4.37 | 3.62 |
| SD | 1.36 | 1.01 | 1.14 | 0.65 |

*Value no 5 of the rhPSMA7.1 series was deleted (statistical outlier).

TABLE 4

Binding affinities (IC$_{50}$ [nM]) of other selected PSMA inhibitors (*).

| No | Inhibitor | IC$_{50}$ [nM] |
|---|---|---|
| 1 | (I-BA)KuE | 7.1 ± 2.4 nM |
| 2 | DCFPyL | 12.3 ± 1.2 nM |
| 3 | DKFZ1007 | 4.2 ± 0.5 nM |

* carried out in our lab using the identical binding assay (Robu et al. EJNMMI Research 2018; 8:30).

Internalization Studies

TABLE 5

Depiction of the individual internalization rates [% of [$^{125}$I]IB-KuE].

| | rhPSMA7.1 | rhPSMA7.2 | rhPSMA7.3 | rhPSMA7.4 |
|---|---|---|---|---|
| 1 | 61.8 | 188.7 | 156.6 | 209.6 |
| 1 | 70.6 | 182.7 | 156.0 | 202.6 |
| 1 | 68.0 | 169.5 | 171.7 | 209.8 |
| 1 | 67.9 | 205.3 | — | — |
| 1 | 71.5 | 212.6 | — | — |
| 1 | 77.5 | 192.3 | — | — |
| Mean | 69.55 | 191.83 | 161.41 | 207.33 |
| SD | 5.19 | 15.54 | 8.88 | 4.06 |

TABLE 6

Internalization values [% of [$^{125}$I][IB-KuE] of other selected PSMA inhibitors (*).

| No | Inhibitor | internalization [%] |
|---|---|---|
| 1 | PSMA-1007 | 118 ± 4 |
| 2 | DCFPyL | 118 ± 5 |

* carried out in our lab using the identical binding assay (Robu et al. EJNMMI Research 2018; 8:30).

Lipophilicities (Octanol-Water Partition Coefficient)

Determianation of the logP values was carried out in phosphate buffered saline (PBS, pH 7.4) and n-octanol (=logP$_{oct/PBS}$).

TABLE 7

Individual log P measurements for rhPSMA7-isomers 7.1-7.4 isomers, determined in octanol/PBS$_{7.4}$ mixtures.

| | rhPSMA7.1 | rhPSMA7.2 | rhPSMA7.3 | rhPSMA7.4 | rhPSMA7-rac |
|---|---|---|---|---|---|
| 1 | −2.79 | −3.00 | −3.03 | −3.09 | −3.23 |
| 2 | −2.82 | −3.01 | −3.08 | −3.12 | −3.15 |
| 3 | −2.80 | −3.00 | −3.07 | −3.06 | −3.17 |
| 4 | −2.84 | −3.00 | −3.02 | −3.07 | −3.10 |
| 5 | −2.88 | −3.03 | −3.06 | −3.10 | −3.17 |
| 6 | −2.90 | −2.96 | −3.07 | −3.04 | −3.24 |
| 7 | −2.85 | −2.94 | −3.06 | −2.99 | −3.80 |
| 8 | −2.86 | −2.89 | −2.86 | −2.97 | −3.60 |
| 9 | −3.14 | −3.02 | −3.39 | −3.37 | −3.87 |
| 10 | −3.29 | −3.02 | −3.33 | −3.43 | −3.61 |
| 11 | −3.26 | −3.06 | −3.34 | −3.29 | −3.76 |
| 12 | −3.02 | −3.02 | −3.34 | −3.48 | −3.65 |
| 13 | −3.15 | −2.99 | −3.20 | −3.52 | −3.67 |
| 14 | −3.57 | −3.02 | −3.39 | −3.50 | — |
| 15 | −3.40 | −3.06 | −3.40 | −3.44 | — |
| 16 | −3.32 | −3.14 | −3.41 | −3.41 | — |
| 17 | −3.64 | −3.40 | −3.48 | −3.56 | — |
| 18 | −3.92 | −3.50 | −3.49 | −3.61 | — |
| 19 | — | −3.45 | −3.32 | −3.58 | — |
| 20 | — | −3.45 | −3.45 | −3.54 | — |
| 21 | — | −3.53 | −3.53 | −3.42 | — |
| 22 | — | −3.48 | −3.43 | −3.57 | — |
| 23 | — | — | −3.56 | −3.67 | — |
| Mean | −3.14 | −3.13 | −3.26 | −3.33 | −3.46 |
| SD | 0.34 | 0.22 | 0.19 | 0.22 | 0.29 |

TABLE 8 log P values of PSMA-1007, DCFPYL, rhPSMA7-rac and rhPSAM7.1-7.4 isomers; (n = 6), octanol/PBS$_{7.4}$.

| Inhibitor | log P |
|---|---|
| PSMA-1007 | −1.6 |
| DCFPyL | −3.4 |
| $^{nat}$Ga-$^{18}$F-rhPSMA7-rac, $^{68}$Ga-$^{nat}$F-rhPSMA7-rac | −3.46 ± 0.29 |
| $^{nat}$Ga-$^{18}$F-rhPSMA7.1 | −3.14 ± 0.34 |
| $^{nat}$Ga-$^{18}$F-rhPSMA7.2 | −3.13 ± 0.22 |
| $^{nat}$Ga-$^{18}$F-rhPSMA7.3 | −3.26 ± 0-19 |
| $^{nat}$Ga-$^{18}$F-rhPSMA7.4 | −3.33 ± 0.22 |

Binding of PSMA Inhibitors to Human Plasma Protein

TABLE 9

HSA binding of of PSMA-1007, DCFPYL, rhPSMA7-rac and rhPSAM7.1-7.4 isomers; (n = 6). Determined on a Chiralpak HSA column (50 × 3 mm, 5 μm, H13H-2433).

| Inhibitor | HSA Binding [%] |
|---|---|
| PSMA-1007 | 97.8 |
| DCFPyL | 14.3 |
| $^{68}$Ga-$^{nat}$F-rhPSMA7-rac | 96.7 |
| $^{nat}$Ga-$^{18}$F-rhPSMA7.1 | 97.7 |
| $^{nat}$Ga-$^{18}$F-rhPSMA7.2 | 97.8 |
| $^{nat}$Ga-$^{18}$F-rhPSMA.3 | 96.9 |
| $^{nat}$Ga-$^{18}$F-rhPSMA7.4 | 96.6 |

Biodistribution of [$^{18}$F][$^{nat}$Ga]rhPSMA7.1-7.4 at 1 h pi

TABLE 10

Biodistribution (in % ID/g) of $^{18}$F-rhPSMAs at 1 h p.i in LNCaP tumor-bearing SCID mice. Data are expressed as mean ± SD (n = 4 for rhPSMA7.1, n = 5 for 7.2, n = 4 for 7.3, n = 5 for 7.4 and n = 3 for 7-rac).

|  | [$^{18}$F][$^{nat}$Ga]-rhPSMA-7-1 | [$^{18}$F][$^{nat}$Ga]-rhPSMA-7-2 | [$^{18}$F][$^{nat}$Ga]-rhPSMA-7-3 | [$^{18}$F][$^{nat}$Ga]-rhPSMA-7-4 | [$^{18}$F][$^{nat}$Ga]-rhPSMA-rac |
|---|---|---|---|---|---|
| blood | 0.53 ± 0.13 | 0.56 ± 0.20 | 0.96 ± 0.24 | 1.15 ± 0.30 | 1.1 ± 0.03 |
| heart | 0.53 ± 0.03 | 0.32 ± 0.13 | 0.87 ± 0.17 | 0.71 ± 0.26 | 0.69 ± 0.07 |
| lung | 1.1 ± 0.21 | 0.89 ± 0.38 | 2.2 ± 0.35 | 1.59 ± 0.61 | 1.4 ± 0.17 |
| liver | 0.75 ± 0.62 | 0.35 ± 0.08 | 0.69 ± 0.13 | 0.69 ± 0.20 | 0.67 ± 0.07 |
| spleen | 20.0 ± 4.2 | 10.1 ± 6.3 | 16.6 ± 2.6 | 18.4 ± 9.77 | 11.1 ± 2.3 |
| pancreas | 0.45 ± 0.12 | 0.21 ± 0.08 | 0.63 ± 0.44 | 0.50 ± 0.30 | 0.60 ± 0.10 |
| stomach | 0.28 ± 0.17 | 0.19 ± 0.08 | 0.44 ± 0.23 | 0.25 ± 0.06 | 0.49 ± 0.07 |
| intestine | 0.30 ± 0.16 | 0.18 ± 0.07 | 0.35 ± 0.07 | 0.37 ± 0.09 | 0.60 ± 0.27 |
| kidneys | 220 ± 24.8 | 87.6 ± 28.8 | 292 ± 45.1 | 153 ± 80.3 | 71.3 ± 13.3 |
| adrenals | 2.0 ± 0.25 | 1.3 ± 0.8 | 2.2 ± 0.83 | 3.57 ± 2.38 | 3.0 ± 0.45 |
| muscle | 0.32 ± 0.30 | 0.13 ± 0.07 | 0.33 ± 0.15 | 0.31 ± 0.08 | 0.36 ± 0.06 |
| bone | 0.50 ± 0.31 | 0.31 ± 0.24 | 0.38 ± 0.32 | 0.62 ± 0.30 | 0.91 ± 0.11 |
| tumor | 14.1 ± 4.1 | 6.5 ± 2.3 | 18.3 ± 7.2 | 18.9 ± 3.27 | 10.4 ± 0.67 |

Biodistribution of [$^{18}$F][$^{nat}$Ga]rhPSMA7.1-7.4 at 1 h pi with Competition

TABLE 11

Biodistribution [% ID/g] of $^{18}$F-labeled rhPSMA tracers co-injected with PMPA (8 mg/kg) at 1 h p.i in LNCaP tumor-bearing SCID mice. Data are expressed as mean ± SD (n = 3).

|  | [$^{18}$F][$^{nat}$Ga]-rhPSMA-7-1 | [$^{18}$F][$^{nat}$Ga]-rhPSMA-7-2 | [$^{18}$F][$^{nat}$Ga]-rhPSMA-7-3 | [$^{18}$F][$^{nat}$Ga]-rhPSMA-7-4 |
|---|---|---|---|---|
| blood | 0.86 ± 0.40 | 1.1 ± 0.31 | 0.55 ± 0.14 | 0.82 ± 0.17 |
| heart | 0.37 ± 0.16 | 0.47 ± 0.09 | 0.26 ± 0.04 | 0.37 ± 0.05 |
| lung | 0.85 ± 0.29 | 1.1 ± 0.32 | 0.69 ± 0.10 | 0.74 ± 0.14 |
| liver | 0.43 ± 0.07 | 0.46 ± 0.07 | 0.46 ± 0.14 | 0.48 ± 0.14 |
| spleen | 0.21 ± 0.08 | 0.26 ± 0.07 | 0.35 ± 0.02 | 0.28 ± 0.15 |
| pancreas | 0.16 ± 0.10 | 0.12 ± 0.05 | 0.11 ± 0.02 | 0.18 ± 0.09 |
| stomach | 0.97 ± 0.81 | 0.21 ± 0.06 | 0.76 ± 0.74 | 0.20 ± 0.07 |
| intestine | 0.66 ± 0.32 | 0.33 ± 0.10 | 0.94 ± 0.97 | 0.36 ± 0.08 |
| kidneys | 10.9 ± 2.5 | 10.9 ± 1.0 | 15.5 ± 2.2 | 7.2 ± 2.4 |
| adrenals | 0.003 ± 0.004 | 0.07 ± 0.10 | 0.07 ± 0.09 | 0.03 ± 0.04 |
| muscle | 0.17 ± 0.15 | 0.09 ± 0.03 | 0.09 ± 0.02 | 0.20 ± 0.05 |
| bone | 0.33 ± 0.24 | 0.57 ± 0.39 | 0.34 ± 0.22 | 1.0 ± 0.8 |
| tumor | 0.94 ± 0.22 | 1.0 ± 0.13 | 1.5 ± 0.4 | 0.99 ± 0.19 |

Quantification of Relative Changes of the Amount of Each rhPSMA7.x Isomer in Blood, Kindey, Liver, Urine and Tumor After Application of [$^{18}$F]rhPSMA7-rac With the aim to quantify the relative changes of each rhPSMA7 isomer in blood, liver, kidney, urine and tumor 30 min after injection of [$^{18}$F]rhPSMA7-rac into a LNCaP tumor bearing mouse, two different homogenization methods (a potter and a ball mill) were used to extract the tracer from kidney, liver and tumor tissue (see Materials and Methods).

Table 12 summarizes the observed efficiencies for both homogenization methods and the efficacy of the subsequent solid phase extraction procedure (to separate the tracer from the protein fraction).

TABLE 12

Determination of the decay corrected extracted activities from the examined tissue samples via the Potter-Elvehjem tissue grinder (n = 1) and the MM-400 ball mill (n = 3).

Potter-Elvehjem tissue grinder (n = 1):

| | EFFICIENCY [%] | | |
|---|---|---|---|
| | Sample extraction | SPE cartridge-loading | overall |
| blood | 93 | 93 | 86 |
| kidney | 91 | 66 | 60 |
| tumor | 90 | 59 | 53 |

MM-400 ball mill (n = 3):

| | EFFICIENCY [%] | | |
|---|---|---|---|
| blood | 98 ± 2 | 94 ± 2 | 92 ± 3 |
| liver | 97 | 89 ± 2 | 86 ± 2 |
| kidney | 63 ± 5 | 68 ± 8 | 43 ± 8 |
| tumor | 64 ± 18 | 65 ± 3 | 42 ± 14 |

Whereas the extraction of activity from the samples using the potter was quite efficient, the use of the ball mill was disappointing. Nevertheless, even with the ball mill >60% extraction efficiency was reached.

Taking into account the possible species that could be formed by metabolic cleavage of amide bonds of rhPSMA7, only a) species with significantly increase lipophilicity of b) F18-fluoride seem probable. Thus in principle it seem possible that "iL" species depicted in FIG. 12 are not extracted from tissue sample (aqueous extraction) and thus do not appear in the final analysis. However, it should be noted that such species would appear in vivo in the liver and intestine (hepatobiliary excretion of lipophilic compounds) or should be bound to plasma proteins (resulting in high activity levels for the blood, which on the other hand showed excellent extraction efficiency).

For quantification of each isomer in the racemic mixture and especially for the poorly separated first and second peak (rhPSMA 7.2 and rhPSMA7.3) a graphical approximation was initially used. This approach was based on the assumption that a) each isomer is eluted from the HPLC column with an identical peak shape and b) the different peak heights can be used as first approximation to calculate by means of linear factors less separated peaks (i.e. rhPSMA 7.2 and rhPSMA7.3).

Based on these assumptions, the first analysis was performed by using one LNCaP tumor bearing mice coinfected with [$^{18}$F][$^{nat}$Ga]rhPSMA7-rac. With the aim to validate these experiments by means of three additional experiments and to improve the graphical analyses by a more valid procedure, the Systat softare package 'PeakFit' was used. PeakFit allows for automated nonlinear separation, analysis and quantification of HPLC elution profiles by deconvolution procedures that uses a Gaussian response function with a Fourier deconvolution/filtering algorithm (https://systat-software.com/products/peakfit/).

A comparison of the graphical analysis of the first experiments revealed that the graphical analysis overestimated the second peak (rhPSMA7.3), whereas the first peak was underestimated. Consequently, all data sets were reanalyzed and quantified by means of PeakFit.

HPLC-Analyses of 4 Independent Experiments in Tumor Bearing Mice 30 min p.i.

1. Evaluation of Peak 3 and 4 (rhPSMA7.4 and rhPSMA 7.1) by Radio-HPLC

It was first examined, whether the deconvolution technique shows similar data for the last two peaks (rhPSMA7.4 and 7.1) that have a good separation (although they are not baseline separated).

2. Evaluation of All Peaks (rhPSMA7.1, 7.2, 7.3 and 7.4) by Radio-HPLC

FIGS. 14a and 14b summarise the percentage change of each rhPSAM7.n isomer in a given sample with respect to its percentage in the injected solution ([$^{18}$F][$^{nat}$Ga]rhPSMA7-rac); the results for the individual experiment are shown in FIG. 14. The proportion of each isomer was quantified by analysis of the HPLC elution profile by Systat 'PeakFit'. Subsequently, the percentage change of each isomer in a given sample with repect to its percentage in the injected solution was calculated.

3. Discussion of the HPLC Data

The radio-HPLC analyses of the radioactivity extracted from the homogenized (kidney, liver, tumor) or diluted (blood) tissues and subsequently immobilized on and eluted from the solid phase extraction cartridge did show no signs of metabolic instability. Thus, no lipophilic metabolic fragments were observed. It should be noted that F-18-fluoride cannot be accurately detected by HPLC under the conditions used for sample preparation (see TLC analysis).

Although there is a clear trend towards the D-Dap-derivative rhPSMA7.1 and 7.3, the overall changes are low (max 15%). It is also important to stress in this context, that FIGS. 15 and 16 show "relative changes" without taking the absolute uptake values into account.

Although rhPSMA7.1 has the weakest affinity and internalization of all rhPSMA7 compounds, it shows the largest positive percentage change in blood liver, kidney and tumor.

Although the reason for this result is unclear, one can speculate that homogenization of the tissue samples, even with the ball mill, did not resulted in a quantitative cell disruption. Thus, the rhPSMA7 tracers with the highest internalization (rhPSMA7.2: 191.83%±15.54%, rhPSMA7.4: 207.33±4.06% and rhPSMA7.3: 161.41%±8.88%) might have been extracted in a less efficient manner, whereas rhPSMA7.1 with its low internalization of only 69.55%±5.29% was efficiently extracted and is consequently overestimated in the HPLC analysis.

In addition, it seems that the rhPSMA compounds 7.2 and 7.4 are somewhat more rapidly excreted (see values for urine). These compounds show generally negative changes in solid tissues and blood, although both compounds exhibit higher affinities and internalization rates when compared with rhPSMA7.1. Whether this might be caused by metabolic degradation of 7.2 and 7.4 (both are L-Dap derivative) is unclear, since no metabolites, i.e. lyophilic metabolites have been detected. It might however be possible, that such metabolites (see FIG. 11), due to their high logP value, are not extractable in aqueous buffer solutions. In this case, they should appear in the liver (see biodistribution) and perhaps in blood samples (high probability for high serum protein binding). Since no elevated activity accumulation has been observed for liver tissue in the course of the biodistribution studies and the activity extraction from blood was highly efficient (see table 3), we assume that no significant degradation for rhPSMA7.2 and 7.4 occurred. This assumption is supported by unsuspicious SUV-values for liver tissue (gall bladder, intestine) in the context of the clinical use of [$^{18}$F]rhpsma-rac in humans.

TLC-Analysis in Tumor Bearing Mice 30 min p.i.

Radio-TLC Analysis was carried out a) on urine samples by directly subjecting a small volume onto a TLC strip, b) by analysis of a small volume of the non-immobilized activity during the SPE process (the 'breakthrough fraction'), and c) by analysis of a small volume of the cartridge eluates.

the urine sample obtained on Jul. 30, 2018 (17.49% free fluoride), the liver sample obtained on Aug. 2, 2018 (25.85% free fluoride).

Whereas the analysis of the urine by TLC is regarded as valid result (see Profile in the FIG. 20), the result obtained with the liver sample is caused by extensive tailing of the peak representing the intact tracer (see FIG. 18). In addition it can be concluded that the above mentioned max. 6% free fluoride represent an overestimation, since peak tailing, even obtained during the QK and release of [F-18]rhPSMA7-rac in PBS (FIG. 18) for clinical application show a tailing of the product peak. As demonstrated by the phosphoimages, this tailing is observed in almost every TLC analysis and contributes to the integrated area of F-18-fluoride.

It need to be noted that neither the biodistribution studies, nor the clinical PET scans in humans (status July 2018:

TABLE 13

TLC analysis of blood, organ and urine samples

| Date | Sample | TLC Scanner | | Phosphoimager | | Comment * TLC signal |
|---|---|---|---|---|---|---|
| | | Intact tracer [%] | $^{18}$F-Fluoride [%] | Intact tracer [%] | $^{18}$F-Fluoride [%] | intensity [cts] (overall very low-low) |
| Jul. 30, 2018 | QK | | | | | |
| | Blood | ~~85,96~~ | ~~14,04~~ | | | ~~57~~ |
| | Liver | ~~80,99~~ | ~~19,01~~ | | | ~~142~~ |
| | Kidney | 94.04 | 5.96 | Methodological problems | | 369 |
| | Urine | 82.51 | 17.49 | | | 726 |
| | Tumor | ~~94,19~~ | ~~5,81~~ | | | ~~172~~ |
| Aug. 1, 2018 | QK | 94.27 | 5.73 | 96.02 | 3.98 | 384 |
| | Blood | ~~90,24~~ | ~~9,76~~ | | | ~~41~~ |
| | Liver | ~~92,49~~ | ~~7,51~~ | 93.92# | 6.084# | ~~173~~ |
| | Kidney | 94.58 | 5.42 | | | 572 |
| | Urine | 96.2 | 3.80 | 98.55 | 1.55 | 395 |
| | Tumor | ~~90,53~~ | ~~9,47~~ | | | ~~190~~ |
| Aug. 2, 2016 | QK | Activity level too low for TLC | | 97.43 | 2.57 | |
| | Blood | | | 96.80 | 3.20 | |
| | Liver | | | 74.15# | 25.85# | |
| | Kidney | | | 96.48 | 3.52 | |
| | Urine | | | 95.85 | 4.15 | |
| | Tumor | | | 96.47 | 4.15 | |

(*) due to the low activity level, the TLC measurements with signal intensity < 200 cts have been deleted.

Discussion of the TLC Data

Since it is very difficult to detect n.c.a. $^{18}$F-fluoride by means of RP-18 chromatography (due to free Si—OH groups of the matrix that interact with nca fluoride), thin layer chromatography was performed to investigate to quantify F-18-Fluoride in the extracted solutions.

Since none of the reagents and salts normally used for protein precipitation are tested for cold fluoride and to avoid possible liberation of F-18-fluoride from the tracer by isotopic exchange, protein precipitation was not implemented in the sample preparation process—although such protein load often result in limited peak separation, peak tailing and activity that sticks at the start line. The solutions obtained after tissue extraction (or blood centrifugation) were directly used for TLC analysis.

Although the activity available for analysis was quite low in all samples, the TLC results reveal that the overall content of F-18-fluride was below approx. 6% in the tissue investigated, except:

approx 1400 scans with [F-18]rhPSMA7-rac) resulted in any suspicious or identifiable F-18-acculuation in bone by liberated F-18-fluoride.

To further investigate the liberation of F-18 fluoride from [F-18]rhPSMA7-rac (as observed in one urine sample) we investigated the occurrence of F-18-Fluoride in further urine samples (normal mice) by means of RP-18 HPLC (new RP-18 end-capped column) and TLC analyses.

Radio-TLC-Analysis of the Formation of F-18-Fluoride in Normal Mice 30 min p.i.

For this purpose normal mice were used. Urine samples were collected by means of a catheter over a period of 30 min. The urine was centrifuged and directly subjected to HPLC and TLC.

As shown in FIG. 21, left column, free F-18-fluoride was found in urine samples of all isomers and is also formed when fresh urine is "incubated with [F-18]rhPSMA7.4. (right column). Identification of F-18-fluoride was performed by demonstrating that a) this species is retained on QMA cartridges (data not shown), b) is eluted in the dead volume of RP-18 columns and c) can not be retained or mobilized on RP-18 columns or RP-18 TLC plates, respectively, irrespective of the mobile phases used.

Due to the fact that such high amounts of F-18 fluoride were not detected in the HPLC analyses of blood or organs, such as kidneys, tumor, liver etc., that no elevated activity uptake in bone was observed in the biodistribution studies in mice and no elevated activity uptake in bone was observed during the clinical PET scans with the [F-18]rhPSMA7-rac compound since [F-18]rhPSMA7-rac has been established for clinical scanning end of 2017 at the TUM (status end July, 2018: approx. 1400 PET scans in patients with prostate cancer) we concluded that [F-18]fluoride might be formed downstream from glomerular filtration of the tracer, resulting in the formation and subsequent excretion of [F-18] fluoride WITHOUT detectable uptake of F-18-fluoride in blood, organs or bones.

This assumption is supported by the literature on the toxicology of fluoride that describes relevant amounts of fluoride in KIDNEYS AND URINE. Normal urinary fluoride levels of 0.3 ppm were observed in mice (Bouaziz H et al., Fluoride 2005; 38(1):23-31). In another publication, the average fluoride concentration in the urine of normal mice was determined to be 0.13-0.14 µg/mL (Poesina N D et al. Rom J Morphol Embryol 2014, 55(2):343-349), and Inkielewicz I. et al. found that the fluoride content in the serum of rats is about 5% of the concentration of fluoride in the kidneys (serum: 0.051 µg/mL, kidneys: 0.942 µg/mL) (Fluoride; 36 (4); 263-266). Taken into account that most of the tracer is specifically taken up into and also physiologically cleared by the kidneys, an elevated fluoride level in the kidney, combined with a body temperature of 36.6° C., might result in a continuous elimination of F-18-fluoride from the rhPSMA-compounds in kidneys.

Figure 22:
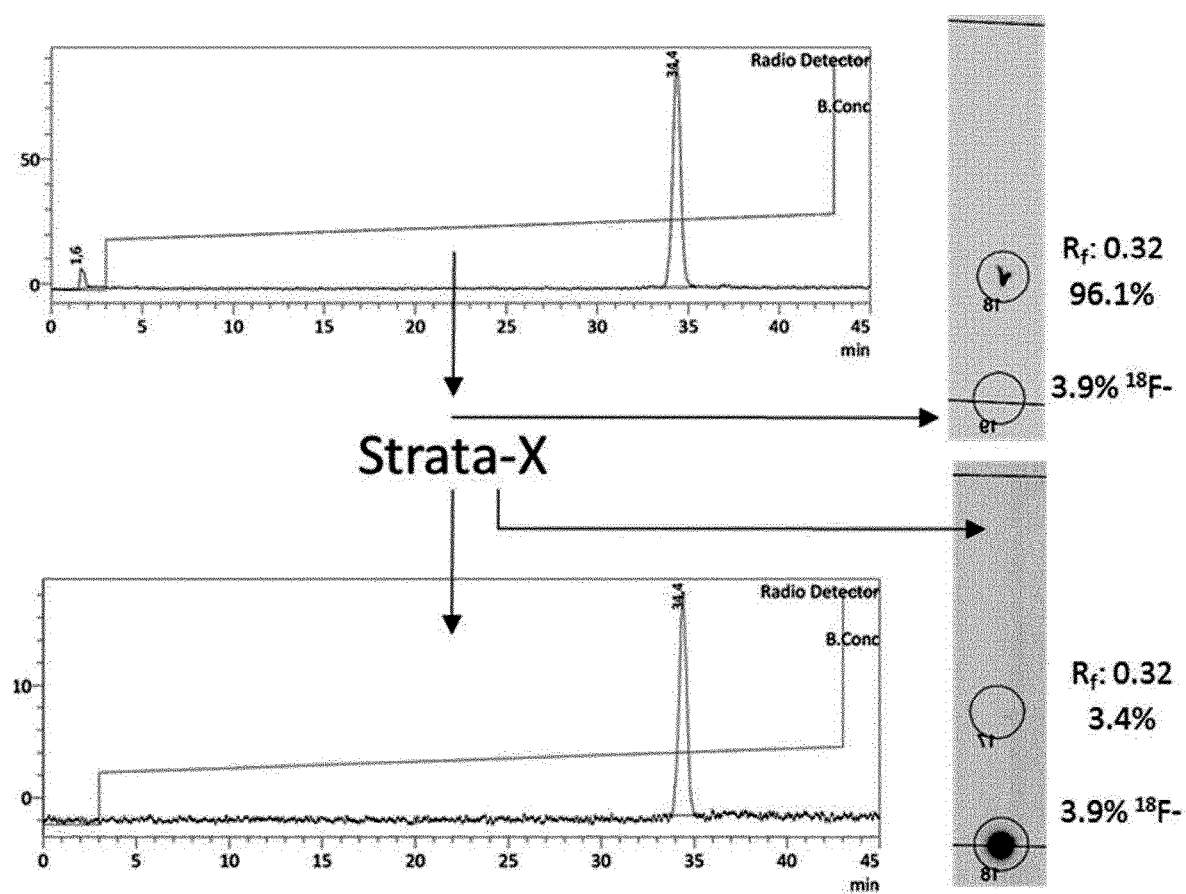

Consequently, fresh and nonradioactive urine samples collected from normal mice were incubated with [F-18] rhPSMA7.x for various time periods (see legend to FIG. 21). FIG. 22, right column, clearly demonstrate that incubation of urine with [F-18]rhPSMA7.x EX VIVO result in the formation of free [F-18]fluoride to various degrees, promoted by the different concentrations of cold F-19-Fluoride in the urine samples and increasing over time.

To further support the hypothesis, 500 nmol cold F-19-fluoride was added to fresh and nonradioactive urine of mice, followed by the addition of [F-18]rhPSMA7.3 and incubation for 2 h. According to the hypothesis, the high concentration of [F-19]fluoride should result in the formation of a significant amount of [F-18]fluoride. FIG. 23 shows that under these conditions 98.5% of the radioactivity is exchanged and forms [F-18]fluoride within 2 h (FIG. 23).

Since isotopic exchange rates are depending on the concentration of the four relevant species in the equilibrium ([F-18]Fluoride, [F-19]fluoride, [F-18]rhPSMA7.3 and [F-19]rhPSMA7.3), it was also investigated, whether the addition of [F-18]fluoride to fresh and radioactive urine (20.6% [F-18]Fluoride, 79.4% [F-18]rhpsma7.3) followed by the addition of cold [F-19]rhPSMA7.3 tracer also result in the labeling of the radiopharmaceutical [F-18]rhPSMA7-3. Unexpectedly, even a small amount of 5 nmol [F-19] rhPSMA7.3 to the urine above resulted in an increase of [F-18]rhPSMA7.3 from 79.4% to 85.8% ([F-18]Fluoride decreased from 20.6% to 14.2%) at room temperature.

The results obtained by isotopic exchange in urine are considered representative for all tracers conjugated with the 4-(di-tert-butyl[(18)F]fluorosilyl)-benzyl)oxy moiety and thus for all rhPSAM7 isomers.

Preclinical Dosimetry, Human Biodistribution and Uptake in Tumor Lesions

Please note that in the following 18F-rhPSMA-7 refers to $^{nat}$Ga-$^{18}$F-rhPSMA7-rac and 18F-rhPSMA-7.3 to $^{nat}$Ga-$^{18}$F-rhPSMA7.3

A) Preclinical Dosimetry of 18F-rhPSMA-7 and 18F-rhPSMA-7.3 in Mice

Aim was to assess the distribution and excretion of $^{18}$F-rhPSMA-7 and $^{18}$F-rhPSMA-7.3 at different time-points up to 300 minutes following a single intravenous administration in mice and to perform calculations for internal dosimetry.

Methods 3-5 mice were injected per timepoint with a mean 25.6±3.6 MBq of 18F-rhPSMA-7 and 28.5±4.8 MBq of 18F-rhPSMA-7.3, respectively. Mice, severe combined immunodeficiency (SCID) were used for the experiments. All animal experiments were conducted in accordance with general animal welfare regulations in Germany and the institutional guidelines for the care and use of animals.

Mice were sacrificed at the following timepoints:

$^{18}$F-rhPSMA-7: 10, 20, 40, 60, 120 and 180 minutes after administration.

$^{18}$F-rhPSMA-7.3: 10, 60, 120, 180 and 300 minutes after administration.

Please note that based on initial experiments exhibiting prolonged renal kidney uptake for $^{18}$F-rhPSMA-7.3 a late timepoint (300 min) was used for the final experiments.

The following tissues/fluids were harvested:

Urine, blood, heart, lung, spleen, pancreas, liver, stomach (emptied), small intestine (emptied), large intestine (emptied), kidneys, bladder, testis, fat, muscle (partial, femoral), femur, tail and brain. Urine was collected with a pipette in the $CO_2$ gas chamber. In case of missing urination in the chamber the bladder was aspirated with an insulin syringe. Blood was withdrawn instantly after sacrifice with an insulin syringe from the heart. All other tissues and organs were dissected and transferred directly in plastic containers.

The weights of the samples in the plastic containers were measured using an electronic balance. The weights of the empty and pre-labeled plastic containers for the dedicated samples were measured beforehand. The tare weight of the plastic containers was subtracted from the weight of the measurement sample with the plastic container. The thus-calculated weight was designated as the weight of the measurement sample.

The plastic containers containing the measurement samples were placed in specific racks of an automatic gamma counter (PerkinElmer-Wallac, Waltham, USA) for measuring the counting rate over 60 seconds (counts per minute=cpm). In addition, a 1% (v/v) standard (n=5) with a known amount of radioactivity was measured together with the samples to convert the counting rate of the organ samples into activity.

Data Analysis

The counting rates of measurement samples were automatically corrected for decay. The radioactivity distribution ratios (unit: percentage of the injected dose (% ID) in the measurement samples were determined using the equation below. The sum of the counting rates from all measurement samples obtained from one mouse was designated as the counting rate for administrated radioactivity.

$$\text{Percentage of injected dose}(\%\ ID) = \frac{\text{counting rate for measurement sample}}{\text{sum of counting rates for all measurement samples from one mouse}} * 100$$

The radioactivity distribution ratio per unit weight of the measurement sample (unit: % ID/g) excluding urine and feces samples was determined by using the equation below. The weight of the measurement sample was determined by subtraction of the empty measurement container from the container including the sample.

$$\text{Percentage of injected dose}(\%\ ID/g) = \frac{\text{Percentage of injected dose}(\%\ ID)}{\text{weight of measurement sample}(g)}$$

Dosimetry Analysis

For consistency of statistical calculations for each radiotracer the same number of time-points for $^{18}$F-rhPSMA-7 and $^{18}$F-rhPSMA-7.3 was used. Therefore, for $^{18}$F-rhPSMA-7 the 10 min and 20 min time points were combined creating a 15 min endpoint.

The time-integral of activity for the accumulation in the significant source organs (AUCs) were generated both with numerical integration and physical decay according to J Juan et al., Journal of Pharmaceutical Sciences, 1993, 82:762-763.

Kirshner et al. established a method that uses linear scaling of the percent injected dose in the animal by the ratio of the organ weights and total body weights of phantoms in both species.

Kirschner A S, Ice R D, Beierwaltes W H. Radiation Dosimetry of 131I-19-Iodocholesterol. J Nucl Med. 1973 Sep. 1; 14(9):713-7.

Kirschner A, Ice R, Beierwaltes W. Letters to the editor. J Nucl Med. (1975):248-9.

In brief, to calculate a human dosimetry from the biodistribution in the mice, an extrapolation was necessary to account for the differences between the animals and humans. Normal-organ radiation doses were estimated for the 70-kg Standard Adult anatomic model using time-depending organ activity concentrations (in percent of the injected dose per gram, % ID/g) and total-body activities measured in the biodistribution studies in mice.

Tissue activity concentrations in mice were converted to tissue fractional activities in the 70-kg Standard Adult using the relative fractional organ masses in the Standard Adult and the "standard" 25-gramm mouse. Time-dependent total-body activity was fit to an exponential function and the difference between the injected activity and the total-body activity was assumed to be excreted to the urine because activity concentrations in the liver and GI tracer were low at all time points studied.

Organ residence time was calculated by numerical integration using the trapezoidal rule and the rest-of-body $^{18}$F residence times was calculated as the difference between the total-body residence time and the sum of the organ and urine residence times. The bladder contents residence time was estimated using the dynamic voiding model in the OLINDA/EXM 1.0 dosimetry software. Finally, the Standard Adult mean organ dose equivalents (in mSv/MBq) and effective dose (also in mSv/MBq) were then calculated using OLINDA/EXM 1.0.

Final calculation of radiation absorbed dose and dosimetry from biodistribution in mice: The tissues or organs in which a significant accumulation of radioactivity occurs (i.e., source organ) were kidney, spleen, lung, liver and heart. With respect to activity accumulation and clearance, a rapid clearance from blood and clearance to urine but relatively slow build-up in kidney was found.

Results

TABLE 14

Dosimetry results for $^{18}$F-rhPSMA-7 using a 3.5 h bladder voiding interval.

| Target Organ | Alpha | Beta | Photon | Total | EDE Cont. | ED Cont. |
|---|---|---|---|---|---|---|
| Adrenals | 0.00E000 | 1.95E−03 | 5.85E−03 | 7.80E−03 | 0.00E000 | 3.90E−05 |
| Brain | 0.00E000 | 1.95E−03 | 2.54E−03 | 4.49E−03 | 0.00E000 | 2.24E−05 |
| Breasts | 0.00E000 | 1.95E−03 | 2.29E−03 | 4.24E−03 | 6.36E−04 | 2.12E−04 |
| Gallbladder Wall | 0.00E000 | 1.95E−03 | 5.54E−03 | 7.49E−03 | 0.00E000 | 0.00E000 |
| LLI Wall | 0.00E000 | 1.95E−03 | 1.41E−02 | 1.61E−02 | 9.66E−04 | 1.93E−03 |
| Small Intestine | 0.00E000 | 1.95E−03 | 8.40E−03 | 1.04E−02 | 0.00E000 | 5.18E−05 |
| Stomach Wall | 0.00E000 | 1.95E−03 | 5.05E−03 | 7.00E−03 | 0.00E000 | 8.40E−04 |
| ULI Wall | 0.00E000 | 1.95E−03 | 7.31E−03 | 9.26E−03 | 0.00E000 | 4.63E−05 |
| Heart Wall | 0.00E000 | 8.82E−04 | 3.54E−03 | 4.42E−03 | 0.00E000 | 0.00E000 |
| Kidneys | 0.00E000 | 4.70E−02 | 1.80E−02 | 6.51E−02 | 3.91E−03 | 3.25E−04 |
| Liver | 0.00E000 | 6.35E−04 | 3.63E−03 | 4.27E−03 | 0.00E000 | 2.13E−04 |
| Lungs | 0.00E000 | 1.25E−03 | 3.04E−03 | 4.30E−03 | 5.16E−04 | 5.16E−04 |
| Muscle | 0.00E000 | 1.95E−03 | 5.73E−03 | 7.68E−03 | 0.00E000 | 3.84E−05 |
| Ovaries | 0.00E000 | 1.95E−03 | 1.35E−02 | 1.55E−02 | 3.87E−03 | 3.09E−03 |
| Pancreas | 0.00E000 | 1.95E−03 | 6.13E−03 | 8.08E−03 | 0.00E000 | 4.04E−05 |
| Red Marrow | 0.00E000 | 1.39E−03 | 5.41E−03 | 6.80E−03 | 8.16E−04 | 8.16E−04 |
| Osteogenic Cells | 0.00E000 | 4.18E−03 | 4.75E−03 | 8.93E−03 | 2.68E−04 | 8.93E−05 |
| Skin | 0.00E000 | 1.95E−03 | 2.98E−03 | 4.93E−03 | 0.00E000 | 4.93E−05 |
| Spleen | 0.00E000 | 1.59E−02 | 1.01E−02 | 2.61E−02 | 1.56E−03 | 1.30E−04 |
| Testes | 0.00E000 | 1.95E−03 | 9.69E−03 | 1.16E−02 | 0.00E000 | 0.00E000 |
| Thymus | 0.00E000 | 1.95E−03 | 3.24E−03 | 5.18E−03 | 0.00E000 | 2.59E−05 |
| Thyroid | 0.00E000 | 1.95E−03 | 3.23E−03 | 5.18E−03 | 1.55E−04 | 2.59E−04 |
| Urinary Bladder Wall | 0.00E000 | 2.45E−01 | 1.08E−01 | 3.54E−01 | 2.12E−02 | 1.77E−02 |

TABLE 14-continued

Dosimetry results for $^{18}$F-rhPSMA-7 using a 3.5 h bladder voiding interval.

| Target Organ | Alpha | Beta | Photon | Total | EDE Cont. | ED Cont. |
|---|---|---|---|---|---|---|
| Uterus | 0.00E000 | 1.95E−03 | 2.61E−02 | 2.80E−02 | 1.68E−03 | 1.40E−04 |
| Total Body | 0.00E000 | 2.37E−03 | 5.39E−03 | 7.77E−03 | 0.00E000 | 0.00E000 |
| Effective Dose Equivalent (mSv/MBq) | | | | | | 3.56E−02 |
| Effective Dose (mSv/MBq) | | | | | | 2.66E−02 |

TABLE 15

Dosimetry results for $^{18}$F-rhPSMA-7 using a 1.0 h bladder voiding interval.

| Target Organ | Alpha | Beta | Photon | Total | EDE Cont. | ED Cont. |
|---|---|---|---|---|---|---|
| Adrenals | 0.00E000 | 1.95E−03 | 5.64E−03 | 7.59E−03 | 0.00E000 | 3.79E−05 |
| Brain | 0.00E000 | 1.95E−03 | 2.54E−03 | 4.49E−03 | 0.00E000 | 2.24E−05 |
| Breasts | 0.00E000 | 1.95E−03 | 2.25E−03 | 4.20E−03 | 6.30E−04 | 2.10E−04 |
| Gallbladder Wall | 0.00E000 | 1.95E−03 | 4.96E−03 | 6.91E−03 | 0.00E000 | 0.00E000 |
| LLI Wall | 0.00E000 | 1.95E−03 | 7.25E−03 | 9.20E−03 | 5.52E−04 | 1.10E−03 |
| Small Intestine | 0.00E000 | 1.95E−03 | 5.79E−03 | 7.73E−03 | 0.00E000 | 3.87E−05 |
| Stomach Wall | 0.00E000 | 1.95E−03 | 4.70E−03 | 6.65E−03 | 0.00E000 | 7.98E−04 |
| ULI Wall | 0.00E000 | 1.95E−03 | 5.33E−03 | 7.27E−03 | 0.00E000 | 3.64E−05 |
| Heart Wall | 0.00E000 | 8.82E−04 | 3.48E−03 | 4.36E−03 | 0.00E000 | 0.00E000 |
| Kidneys | 0.00E000 | 4.70E−02 | 1.76E−02 | 6.47E−02 | 3.88E−03 | 3.23E−04 |
| Liver | 0.00E000 | 6.35E−04 | 3.39E−03 | 4.02E−03 | 0.00E000 | 2.01E−04 |
| Lungs | 0.00E000 | 1.25E−03 | 3.01E−03 | 4.26E−03 | 5.11E−04 | 5.11E−04 |
| Muscle | 0.00E000 | 1.95E−03 | 4.01E−03 | 5.96E−03 | 0.00E000 | 2.98E−05 |
| Ovaries | 0.00E000 | 1.95E−03 | 7.21E−03 | 9.16E−03 | 2.29E−03 | 1.83E−03 |
| Pancreas | 0.00E000 | 1.95E−03 | 5.86E−03 | 7.80E−03 | 0.00E000 | 3.90E−05 |
| Red Marrow | 0.00E000 | 1.39E−03 | 4.29E−03 | 5.68E−03 | 6.82E−04 | 6.82E−04 |
| Osteogenic Cells | 0.00E000 | 4.18E−03 | 4.09E−03 | 8.27E−03 | 2.48E−04 | 8.27E−05 |
| Skin | 0.00E000 | 1.95E−03 | 2.38E−03 | 4.32E−03 | 0.00E000 | 4.32E−05 |
| Spleen | 0.00E000 | 1.59E−02 | 9.90E−03 | 2.58E−02 | 1.55E−03 | 1.29E−04 |
| Testes | 0.00E000 | 1.95E−03 | 5.09E−03 | 7.03E−03 | 0.00E000 | 0.00E000 |
| Thymus | 0.00E000 | 1.95E−03 | 3.20E−03 | 5.15E−03 | 0.00E000 | 2.57E−05 |
| Thyroid | 0.00E000 | 1.95E−03 | 3.23E−03 | 5.17E−03 | 1.55E−04 | 2.59E−04 |
| Urinary Bladder Wall | 0.00E000 | 7.87E−02 | 3.66E−02 | 1.15 E−01 | 6.92E−03 | 5.76E−03 |
| Uterus | 0.00E000 | 1.95E−03 | 1.12E−02 | 1.31E−02 | 7.87E−04 | 6.56E−05 |
| Total Body | 0.00E000 | 2.27E−03 | 3.93E−03 | 6.19E−03 | 0.00E000 | 0.00E000 |
| Effective Dose Equivalent (mSv/MBq) | | | | | | 1.82E−02 |
| Effective Dose (mSv/MBq) | | | | | | 1.22E−02 |

TABLE 16

Dosimetry results for $^{18}$F-rhPSMA-7.3 using a 3.5 h bladder voiding interval.

| Target Organ | Alpha | Beta | Photon | Total | EDE Cont. | ED Cont. |
|---|---|---|---|---|---|---|
| Adrenals | 0.00E000 | 3.12E−03 | 7.93E−03 | 1.10E−02 | 0.00E000 | 5.52E−05 |
| Brain | 0.00E000 | 3.12E−03 | 4.07E−03 | 7.19E−03 | 0.00E000 | 3.59E−05 |
| Breasts | 0.00E000 | 3.12E−03 | 3.55E−03 | 6.67E−03 | 1.00E−03 | 3.34E−04 |
| Gallbladder Wall | 0.00E000 | 3.12E−03 | 7.46E−03 | 1.06E−02 | 0.00E000 | 0.00E000 |
| LLI Wall | 0.00E000 | 3.12E−03 | 1.28E−02 | 1.59E−02 | 9.53E−04 | 1.91E−03 |
| Small Intestine | 0.00E000 | 3.12E−03 | 9.42E−03 | 1.25E−02 | 0.00E000 | 6.27E−05 |
| Stomach Wall | 0.00E000 | 3.12E−03 | 7.02E−03 | 1.01E−02 | 0.00E000 | 1.22E−03 |
| ULI Wall | 0.00E000 | 3.12E−03 | 8.57E−03 | 1.17E−02 | 0.00E000 | 5.85E−05 |
| Heart Wall | 0.00E000 | 1.32E−03 | 5.39E−03 | 6.71E−03 | 0.00E000 | 0.00E000 |
| Kidneys | 0.00E000 | 5.11E−02 | 2.07E−02 | 7.18E−02 | 4.31E−03 | 3.59E−04 |
| Liver | 0.00E000 | 9.70E−04 | 5.02E−03 | 5.99E−03 | 0.00E000 | 3.00E−04 |
| Lungs | 0.00E000 | 1.95E−03 | 4.66E−03 | 6.61E−03 | 7.93E−04 | 7.93E−04 |
| Muscle | 0.00E000 | 3.12E−03 | 6.55E−03 | 9.67E−03 | 0.00E000 | 4.83E−05 |
| Ovaries | 0.00E000 | 3.12E−03 | 1.26E−02 | 1.57E−02 | 3.92E−03 | 3.14E−03 |
| Pancreas | 0.00E000 | 3.12E−03 | 8.29E−03 | 1.14E−02 | 0.00E000 | 5.70E−05 |
| Red Marrow | 0.00E000 | 2.22E−03 | 6.79E−03 | 9.01E−03 | 1.08E−03 | 1.08E−03 |
| Osteogenic Cells | 0.00E000 | 6.70E−03 | 6.52E−03 | 1.32E−02 | 3.97E−04 | 1.32E−04 |
| Skin | 0.00E000 | 3.12E−03 | 3.83E−03 | 6.95E−03 | 0.00E000 | 6.95E−05 |
| Spleen | 0.00E000 | 1.52E−02 | 1.15E−02 | 2.67E−02 | 1.60E−03 | 1.34E−04 |
| Testes | 0.00E000 | 3.12E−03 | 8.96E−03 | 1.21E−02 | 0.00E000 | 0.00E000 |
| Thymus | 0.00E000 | 3.12E−03 | 5.08E−03 | 8.20E−03 | 0.00E000 | 4.10E−05 |
| Thyroid | 0.00E000 | 3.12E−03 | 5.15E−03 | 8.27E−03 | 2.48E−04 | 4.14E−04 |

TABLE 16-continued

Dosimetry results for $^{18}$F-rhPSMA-7.3 using a 3.5 h bladder voiding interval.

| Target Organ | Alpha | Beta | Photon | Total | EDE Cont. | ED Cont. |
|---|---|---|---|---|---|---|
| Urinary Bladder Wall | 0.00E000 | 1.56E-01 | 7.14E-02 | 2.27E-01 | 1.36E-02 | 1.14E-02 |
| Uterus | 0.00E000 | 3.12E-03 | 2.04E-02 | 2.36E-02 | 1.41E-03 | 1.18E-04 |
| Total Body | 0.00E000 | 3.52E-03 | 6.33E-03 | 9.86E-03 | 0.00E000 | 0.00E000 |
| Effective Dose Equivalent (mSv/MBq) | | | | | | 2.94E-02 |
| Effective Dose (mSv/MBq) | | | | | | 2.17E-02 |

TABLE 17

Dosimetry results for $^{18}$F-rhPSMA-7.3 using a 1.0 h bladder voiding interval.

| Target Organ | Alpha | Beta | Photon | Total | EDE Cont. | ED Cont. |
|---|---|---|---|---|---|---|
| Adrenals | 0.00E000 | 3.12E-03 | 7.79E-03 | 1.09E-02 | 0.00E000 | 5.46E-05 |
| Brain | 0.00E000 | 3.12E-03 | 4.06E-03 | 7.18E-03 | 0.00E000 | 3.59E-05 |
| Breasts | 0.00E000 | 3.12E-03 | 3.53E-03 | 6.65E-03 | 9.97E-04 | 3.32E-04 |
| Gallbladder Wall | 0.00E000 | 3.12E-03 | 7.11E-03 | 1.02E-02 | 0.00E000 | 0.00E000 |
| LLI Wall | 0.00E000 | 3.12E-03 | 8.45E-03 | 1.16E-02 | 6.94E-04 | 1.39E-03 |
| Small Intestine | 0.00E000 | 3.12E-03 | 7.78E-03 | 1.09E-02 | 0.00E000 | 5.45E-05 |
| Stomach Wall | 0.00E000 | 3.12E-03 | 6.80E-03 | 9.92E-03 | 0.00E000 | 1.19E-03 |
| ULI Wall | 0.00E000 | 3.12E-03 | 7.33E-03 | 1.05E-02 | 0.00E000 | 5.23E-05 |
| Heart Wall | 0.00E000 | 1.32E-03 | 5.36E-03 | 6.68E-03 | 0.00E000 | 0.00E000 |
| Kidneys | 0.00E000 | 5.11E-02 | 2.04E-02 | 7.16E-02 | 4.29E-03 | 3.58E-04 |
| Liver | 0.00E000 | 9.70E-04 | 4.87E-03 | 5.84E-03 | 0.00E000 | 2.92E-04 |
| Lungs | 0.00E000 | 1.95E-03 | 4.63E-03 | 6.58E-03 | 7.90E-04 | 7.90E-04 |
| Muscle | 0.00E000 | 3.12E-03 | 5.47E-03 | 8.59E-03 | 0.00E000 | 4.30E-05 |
| Ovaries | 0.00E000 | 3.12E-03 | 8.61E-03 | 1.17E-02 | 2.93E-03 | 2.35E-03 |
| Pancreas | 0.00E000 | 3.12E-03 | 8.12E-03 | 1.12E-02 | 0.00E000 | 5.62E-05 |
| Red Marrow | 0.00E000 | 2.22E-03 | 6.09E-03 | 8.31E-03 | 9.97E-04 | 9.97E-04 |
| Osteogenic Cells | 0.00E000 | 6.70E-03 | 6.11E-03 | 1.28E-02 | 3.84E-04 | 1.28E-04 |
| Skin | 0.00E000 | 3.12E-03 | 3.45E-03 | 6.57E-03 | 0.00E000 | 6.57E-05 |
| Spleen | 0.00E000 | 1.52E-02 | 1.14E-02 | 2.66E-02 | 1.59E-03 | 1.33E-04 |
| Testes | 0.00E000 | 3.12E-03 | 6.08E-03 | 9.20E-03 | 0.00E000 | 0.00E000 |
| Thymus | 0.00E000 | 3.12E-03 | 5.06E-03 | 8.18E-03 | 0.00E000 | 4.09E-05 |
| Thyroid | 0.00E000 | 3.12E-03 | 5.15E-03 | 8.27E-03 | 2.48E-04 | 4.13E-04 |
| Urinary Bladder Wall | 0.00E000 | 5.18E-02 | 2.66E-02 | 7.84E-02 | 4.70E-03 | 3.92E-03 |
| Uterus | 0.00E000 | 3.12E-03 | 1.11E-02 | 1.43E-02 | 8.55E-04 | 7.13E-05 |
| Total Body | 0.00E000 | 3.45E-03 | 5.42E-03 | 8.87E-03 | 0.00E000 | 0.00E000 |
| Effective Dose Equivalent (mSv/MBq) | | | | | | 1.85E-02 |
| Effective Dose (mSv/MBq) | | | | | | 1.28E-02 |

CONCLUSION

The radioactivity distribution ratios were highest in kidneys after administration of both $^{18}$F-rhPSMA-7 and $^{18}$F-rhPSMA-7.3 at all examined time points in mice. Moreover, it was high in the spleen and in the bladder for both radiotracers compared to all other assessed tissues, where activity ratios were lower than 8% ID/g.

Since the majority of $^{18}$F-rhPSMA-7/$^{18}$F-rhPSMA-7.3 activity augment in the kidneys and the excretion via bladder reveal high activities, the main excretion route is defined via kidneys and the urinary system.

Using a 3.5 h and 1.0 h bladder voiding interval the extrapolated total effective doses were 2.66E-02 and 1.22E-02 mSv/MBq for $^{18}$F-rhPSMA-7 and 2.17E-02 and 1.28E-02 mSv/MBq for $^{18}$F-rhPSMA-7.3, respectively. An injection of up to 370 MBq (10 mCi) for a clinical scan would result in a favorable radiation exposure of less than 5 mSv for both agents assuming a 1h voiding interval.

Differences worth to mention between both radiotracers are only evident regarding kidney uptake as $^{18}$F-rhPSMA-7.3 tends to accumulate more gradual with longer retention. Yet radiation exposure is comparable between both agents.
B) Human Biodistribution and Uptake in Tumor Lesions of 18F-rhPSMA-7 and 18F-rhPSMA-7.3

The following sections describe biodistribution of 18F-rhPSMA-7 and 18F-rhPSMA-7.3. Proof-of-concept evaluation was conducted under compassionate use. The agent was applied in compliance with The German Medicinal Products Act, AMG § 13 2b, and in accordance with the responsible regulatory body (Government of Oberbayern).

All subjects were examined on a Biograph mCT scanner (Siemens Medical Solutions, Erlangen, Germany). All PET scans were acquired in 3D-mode with an acquisition time of 2-4 min per bed position. Emission data were corrected for randoms, dead time, scatter, and attenuation and were reconstructed iteratively by an ordered-subsets expectation maximization algorithm (four iterations, eight subsets) followed by a postreconstruction smoothing Gaussian filter (5-mm full width at one-half maximum).
Methods Human biodistribution was estimated by analysing clinical $^{18}$F-rhPSMA-7- and $^{18}$F-rhPSMA-7.3-PET/CT exams in 47 and 32 patients, respectively. Mean injected activities were 324 (range 236-424) MBq vs. 345 (range 235-420) MBq and uptake times were 84 (range 42-166) min and vs. 76 (range 59-122) min for $^{18}$F-rhPSMA-7 vs. $^{18}$F-rhPSMA-7.3, respectively.

The mean and maximum standardized uptake values (SUVmean/SUVmax) were determined for background (gluteal muscle), normal organs (salivary glands, blood pool, lung, liver, spleen, pancreas, duodenum, kidney, bladder, bone) and three representative tumor lesions. Tumor uptake was analyzed in 89 lesions (26 primary tumors/local recurrences, 23 bone, 38 lymph node and 2 visceral metastases) and 63 lesions (14 primary tumors/local recurrences, 30 bone, 18 lymph node and 1 visceral metastases) for $^{18}$F-rhPSMA-7 and $^{18}$F-rhPSMA-7.3, respectively.

For calculation of the SUV, circular regions of interest were drawn around areas with focally increased uptake in transaxial slices and automatically adapted to a three-dimensional volume of interest (VOI) at a 50% isocontour. Organ-background and Tumor-background ratios were calculated.

Results

Human biodistribution of $^{18}$F-rhPSMA-7 and $^{18}$F-rhPSMA-7.3 showed the typical pattern known from other PSMA-ligands. Uptake parameters for $^{18}$F-rhPSMA-7 and $^{18}$F-rhPSMA-7.3 were very similar with a lower activity retention in the bladder and higher uptake in tumor lesions for $^{18}$F-rhPSMA-7.3: SUVmean for $^{18}$F-rhPSMA-7 vs. $^{18}$F-rhPSMA-7.3 were 16.9 vs. 16.0 (parotid gland), 19.6 vs. 19.6 (submandibular gland), 2.0 vs. 1.9 (blood pool), 0.7 vs. 0.7 (lungs), 7.0 vs. 7.3 (liver), 9.1 vs. 8.5 (spleen), 32.4 vs. 35.5 (kidney), 2.5 vs. 2.8 (pancreas), 10.9 vs. 11.0 (duodenum), 1.1 vs. 1.3 (non-diseased bone) and 10.2 vs. 2.0 (bladder) for $^{18}$F-rhPSMA-7 vs. $^{18}$F-rhPSMA-7.3, respectively. In particular, uptake values of $^{18}$F-rhPSMA-7.3 vs. $^{18}$F-rhPSMA-7 were significantly lower for retention in the bladder (2.0±0.8 vs. 6.3±21.2, p<0.05) and significantly higher for tumor lesions (32.5±42.7 vs. 20.0±20.2, p<0.05).

TABLE 18

SUVmax and SUVmean of normal organs and tumor lesions using $^{18}$F-rhPSMA-7. Data are shown as mean, minimum and maximum.

| | SUVmax | | | SUVmean | | |
|---|---|---|---|---|---|---|
| | mean | min | max | mean | min | max |
| background | 1.0 | 0.6 | 1.8 | 0.6 | 0.4 | 1.2 |
| parotic gland | 23.8 | 8.2 | 42.3 | 16.9 | 5.5 | 32.7 |
| submandibular gland | 27.0 | 10.1 | 43.8 | 19.6 | 7.0 | 29.7 |
| bloodpool | 2.4 | 1.6 | 3.9 | 2.0 | 1.1 | 17.0 |
| lungs | 1.1 | 0.5 | 3.1 | 0.7 | 0.3 | 2.0 |
| liver | 9.5 | 4.5 | 25.2 | 7.0 | 3.2 | 17.7 |
| spleen | 11.8 | 4.7 | 21.0 | 9.1 | 3.4 | 17.1 |
| kidney | 44.8 | 19.1 | 75.2 | 32.4 | 13.2 | 54.7 |
| pancreas | 3.7 | 1.8 | 7.9 | 2.5 | 1.3 | 5.5 |
| duodenum | 14.8 | 2.8 | 32.7 | 10.9 | 1.9 | 23.9 |
| bone | 1.7 | 0.8 | 3.1 | 1.1 | 0.6 | 2.1 |
| bladder | 8.5 | 0.5 | 112.0 | 6.3 | 0.3 | 85.7 |
| tumor | 27.6 | 3.1 | 167.2 | 20.0 | 2.1 | 115.7 |

TABLE 19

SUVmax and SUVmean of normal organs and tumor lesions using $^{18}$F-rhPSMA-7.3. Data are shown as mean, minimum and maximum.

| | SUVmax | | | SUVmean | | |
|---|---|---|---|---|---|---|
| | mean | min | max | mean | min | max |
| background | 1.0 | 0.6 | 1.7 | 0.7 | 0.4 | 1.1 |
| parotid gland | 24.6 | 11.2 | 38.3 | 16.0 | 8.2 | 25.0 |
| submandibular gland | 28.4 | 14.6 | 47.4 | 19.6 | 10.4 | 33.4 |
| bloodpool | 2.8 | 1.9 | 3.9 | 1.8 | 1.3 | 2.5 |
| lungs | 1.1 | 0.7 | 1.9 | 0.7 | 0.4 | 1.1 |
| liver | 9.7 | 4.6 | 15.4 | 7.3 | 3.2 | 12.3 |
| spleen | 11.4 | 5.0 | 22.5 | 8.5 | 3.7 | 17.9 |
| kidney | 51.9 | 30.9 | 99.9 | 35.5 | 20.7 | 70.6 |

TABLE 19-continued

SUVmax and SUVmean of normal organs and tumor lesions using $^{18}$F-rhPSMA-7.3. Data are shown as mean, minimum and maximum.

| | SUVmax | | | SUVmean | | |
|---|---|---|---|---|---|---|
| | mean | min | max | mean | min | max |
| pancreas | 4.2 | 2.4 | 7.8 | 2.8 | 1.6 | 5.2 |
| duodenum | 16.4 | 6.1 | 32.2 | 11.0 | 3.0 | 23.0 |
| bone | 2.1 | 1.1 | 3.4 | 1.3 | 0.7 | 2.2 |
| bladder | 3.1 | 1.1 | 6.0 | 2.0 | 0.7 | 4.1 |
| tumor | 44.0 | 2.4 | 316.0 | 32.5 | 1.6 | 224.1 |

TABLE 20

Ratio SUVmax and SUVmean to background of normal organs and tumor lesions using $^{18}$F-rhPSMA-7. Data are shown as mean, minimum and maximum.

| | ratio SUVmax | | | ratio SUVmean | | |
|---|---|---|---|---|---|---|
| | mean | min | max | mean | min | max |
| parotid gland | 25.2 | 8.2 | 45.3 | 28.3 | 9.2 | 54.5 |
| submandibular gland | 28.7 | 10.1 | 54.7 | 33.3 | 11.7 | 61.8 |
| bloodpool | 2.5 | 1.3 | 4.8 | 3.2 | 1.6 | 21.3 |
| lungs | 1.1 | 0.4 | 3.3 | 1.1 | 0.4 | 4.0 |
| liver | 10.4 | 4.7 | 42.0 | 11.9 | 4.6 | 44.3 |
| spleen | 12.5 | 4.7 | 35.0 | 15.1 | 5.7 | 39.5 |
| kidney | 48.1 | 18.2 | 98.7 | 55.2 | 19.8 | 109.3 |
| pancreas | 3.9 | 1.5 | 11.3 | 4.3 | 1.9 | 10.8 |
| duodenum | 15.7 | 2.8 | 31.3 | 18.4 | 3.2 | 35.3 |
| bone | 1.7 | 0.9 | 2.9 | 1.8 | 1.0 | 3.2 |
| bladder | 8.7 | 0.6 | 112.0 | 10.2 | 0.5 | 142.8 |
| tumor | 32.0 | 3.1 | 278.6 | 36.0 | 3.5 | 289.3 |

TABLE 21

Ratio SUVmax and SUVmean to background of normal organs and tumor lesions using $^{18}$F-rhPSMA-7.3. Data are shown as mean, minimum and maximum.

| | ratio SUVmax | | | ratio SUVmean | | |
|---|---|---|---|---|---|---|
| | mean | min | max | mean | min | max |
| parotid gland | 24.7 | 11.9 | 46.2 | 25.2 | 12.4 | 44.6 |
| submandibular gland | 28.2 | 14.0 | 62.1 | 30.6 | 15.7 | 62.3 |
| bloodpool | 2.8 | 1.5 | 5.2 | 2.9 | 1.7 | 4.9 |
| lungs | 1.0 | 0.6 | 1.8 | 1.0 | 0.6 | 1.8 |
| liver | 9.7 | 4.0 | 19.0 | 11.4 | 4.1 | 20.7 |
| spleen | 11.4 | 3.6 | 22.4 | 13.3 | 3.9 | 28.6 |
| kidney | 51.8 | 25.7 | 93.0 | 55.6 | 27.6 | 95.5 |
| pancreas | 4.1 | 2.2 | 6.9 | 4.4 | 2.3 | 7.8 |
| duodenum | 16.2 | 6.9 | 34.3 | 17.1 | 4.7 | 39.4 |
| bone | 2.0 | 1.1 | 3.2 | 2.1 | 1.0 | 3.6 |
| bladder | 3.1 | 0.9 | 5.5 | 3.1 | 0.9 | 6.8 |
| tumor | 43.6 | 1.7 | 321.2 | 50.8 | 1.8 | 356.4 |

CONCLUSION

Human biodistribution is similar between $^{18}$F-rhPSMA-7 and $^{18}$F-rhPSMA-7.3 for most normal organs. However, tracer retention in the bladder is significantly lower and uptake in tumor lesions significantly higher for $^{18}$F-rhPSMA-7.3 posing a clear advantage for clinical imaging. Imaging examples with favorable human biodistribution and high uptake of tumor lesions of $^{18}$F-rhPSMA-7.3 are shown in FIG. 28.

The invention claimed is:
1. A compound having a chemical structure:

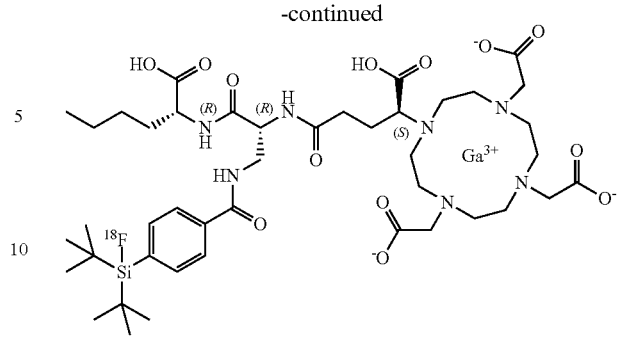

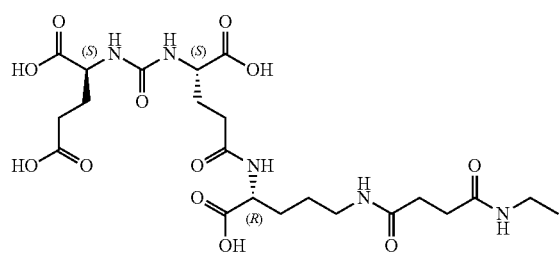

or a pharmaceutically acceptable salt thereof.

2. A pharmaceutical or diagnostic composition comprising or consisting of one or more conjugates in accordance with claim 1.

3. A method of imaging and/or diagnosing cancer comprising administering a conjugate according to claim 1 to a patient in need thereof.

4. A method of treating cancer comprising administering a conjugate according to claim 1 to a patient in need thereof.

5. A method of reducing neoangiogenesis/angiogenesis comprising administering a conjugate according to claim 1 to a patient in need thereof.

6. A method according to claim 4 wherein the cancer is prostate, breast, lung, colorectal or renal cell carcinoma.

* * * * *